US010675050B2

(12) United States Patent
Staunton et al.

(10) Patent No.: US 10,675,050 B2
(45) Date of Patent: Jun. 9, 2020

(54) END EFFECTOR WITH LIQUID DELIVERY SYSTEM

(71) Applicant: Stryker Corporation, Kalamazoo, MI (US)

(72) Inventors: Douglas Alan Staunton, Kalamazoo, MI (US); James Flatt, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 457 days.

(21) Appl. No.: 15/404,416

(22) Filed: Jan. 12, 2017

(65) Prior Publication Data

US 2017/0119421 A1 May 4, 2017

Related U.S. Application Data

(63) Continuation of application No. 14/214,703, filed on Mar. 15, 2014, now Pat. No. 9,566,121.
(Continued)

(51) Int. Cl.
*A61B 17/32* (2006.01)
*A61B 17/16* (2006.01)
(Continued)

(52) U.S. Cl.
CPC ........ *A61B 17/32002* (2013.01); *A61B 34/30* (2016.02); *A61B 34/76* (2016.02); *A61B 50/13* (2016.02); *F16D 1/0817* (2013.01); *F16D 1/116* (2013.01); *F16D 15/00* (2013.01); *F16J 15/3256* (2013.01); *A61B 17/162* (2013.01); *A61B 17/1615* (2013.01); *A61B 17/1624* (2013.01); *A61B 90/98* (2016.02);
(Continued)

(58) Field of Classification Search
CPC .. A61B 17/32002; A61B 2017/320032; A61B 10/0266; A61B 10/0275; A61B 17/320758
See application file for complete search history.

(56) References Cited

U.S. PATENT DOCUMENTS 2,679,101 A    5/1954   Werner Steuer et al.
3,400,459 A    9/1968   Stemler
(Continued)

FOREIGN PATENT DOCUMENTS

CN    1216454 A     5/1999
DE    29716551 U1   2/1998
(Continued)

OTHER PUBLICATIONS

International Search Report of PCT/US2014/029909; dated Feb. 6, 2015; 20 pages.
(Continued)

*Primary Examiner* — Wade Miles
(74) *Attorney, Agent, or Firm* — Howard & Howard Attorneys PLLC

(57) ABSTRACT

An end effector includes a drive system to rotatably drive a removeable cutting accessory. The cutting accessory defines a bore. The drive system includes a drive member that defines a lumen. A cartridge is provided to deliver liquid from a liquid source, through the lumen of the drive member, through the bore of the cutting accessory, and to a surgical site.

12 Claims, 60 Drawing Sheets

Related U.S. Application Data

(60) Provisional application No. 61/798,729, filed on Mar. 15, 2013.

(51) Int. Cl.

| | | |
|---|---|---|
| *A61B 17/00* | (2006.01) | |
| *F16D 1/08* | (2006.01) | |
| *F16D 1/116* | (2006.01) | |
| *A61B 50/13* | (2016.01) | |
| *A61B 34/00* | (2016.01) | |
| *A61B 34/30* | (2016.01) | |
| *F16D 15/00* | (2006.01) | |
| *F16J 15/3256* | (2016.01) | |
| *F16D 1/10* | (2006.01) | |
| *A61B 90/00* | (2016.01) | |
| *A61B 90/98* | (2016.01) | |

(52) U.S. Cl.
CPC .......... *A61B 2017/00477* (2013.01); *A61B 2017/1651* (2013.01); *A61B 2090/0801* (2016.02); *A61B 2090/0811* (2016.02); *A61B 2217/007* (2013.01); *F16D 2001/103* (2013.01)

(56) References Cited

U.S. PATENT DOCUMENTS

| | | |
|---|---|---|
| 3,475,817 A | 11/1969 | Loge |
| 3,791,660 A | 2/1974 | Bostley |
| 3,835,858 A | 9/1974 | Hagen |
| 3,847,154 A | 11/1974 | Nordin |
| 3,867,943 A | 2/1975 | Nordin |
| 3,905,609 A | 9/1975 | Sussman |
| 4,030,617 A | 6/1977 | Richter |
| 4,071,029 A | 1/1978 | Richmond et al. |
| 4,283,764 A | 8/1981 | Crum et al. |
| 4,298,308 A | 11/1981 | Richter |
| 4,517,977 A | 5/1985 | Frost |
| 4,589,810 A | 5/1986 | Heindl et al. |
| 4,648,783 A | 3/1987 | Tan et al. |
| 4,867,618 A | 9/1989 | Brohammer |
| 4,895,146 A | 1/1990 | Draenert |
| 4,922,069 A | 5/1990 | Huizenga |
| 4,944,642 A | 7/1990 | Andersson |
| 5,022,857 A | 6/1991 | Matsutani et al. |
| 5,040,979 A | 8/1991 | Kuhn |
| 5,055,044 A | 10/1991 | Kuhn |
| 5,096,421 A | 3/1992 | Seney |
| 5,212,433 A | 5/1993 | Yasuyuki |
| 5,363,474 A | 11/1994 | Sarugaku et al. |
| 5,490,683 A | 2/1996 | Mickel et al. |
| 5,490,860 A | 2/1996 | Middle |
| 5,649,956 A | 7/1997 | Jensen et al. |
| 5,665,945 A | 9/1997 | Oshima |
| 5,682,886 A | 11/1997 | Delp et al. |
| 5,741,084 A | 4/1998 | Del Rio et al. |
| 5,741,263 A | 4/1998 | Umber et al. |
| 5,748,854 A | 5/1998 | Watanabe et al. |
| 5,762,458 A | 6/1998 | Wang et al. |
| 5,783,922 A | 7/1998 | Hashimoto et al. |
| 5,807,378 A | 9/1998 | Jensen et al. |
| 5,814,038 A | 9/1998 | Jensen et al. |
| 5,816,803 A | 10/1998 | Nakanishi |
| 5,855,583 A | 1/1999 | Wang et al. |
| 5,915,673 A | 6/1999 | Kazerooni |
| 6,007,550 A | 12/1999 | Wang et al. |
| 6,012,922 A | 1/2000 | Novak |
| 6,033,415 A | 3/2000 | Mittelstadt et al. |
| 6,045,564 A | 4/2000 | Walen |
| 6,062,575 A | 5/2000 | Mickel et al. |
| 6,063,095 A | 5/2000 | Wang et al. |
| 6,080,181 A | 6/2000 | Jensen et al. |
| 6,102,850 A | 8/2000 | Wang et al. |
| 6,132,448 A | 10/2000 | Perez et al. |
| 6,151,789 A | 11/2000 | Raab et al. |
| 6,160,324 A | 12/2000 | Terada et al. |
| 6,212,443 B1 | 4/2001 | Nagata et al. |
| 6,222,338 B1 | 4/2001 | Villaret |
| 6,325,808 B1 | 12/2001 | Bernard et al. |
| 6,331,181 B1 | 12/2001 | Tierney et al. |
| 6,352,532 B1 | 3/2002 | Kramer et al. |
| 6,385,508 B1 | 5/2002 | McGee et al. |
| 6,386,513 B1 | 5/2002 | Kazerooni |
| 6,396,232 B2 | 5/2002 | Haanpaa et al. |
| 6,413,264 B1 | 7/2002 | Jensen et al. |
| 6,436,107 B1 | 8/2002 | Wang et al. |
| 6,438,455 B2 | 8/2002 | Matsumoto |
| 6,491,701 B2 | 12/2002 | Tierney et al. |
| 6,494,892 B1 | 12/2002 | Ireland et al. |
| 6,587,750 B2 | 7/2003 | Gerbi et al. |
| 6,620,174 B2 | 9/2003 | Jensen et al. |
| 6,699,177 B1 | 3/2004 | Wang et al. |
| 6,733,218 B2 | 5/2004 | Del Rio et al. |
| 6,780,189 B2 | 8/2004 | Tidwell et al. |
| 6,821,120 B2 | 11/2004 | Suzuki et al. |
| 6,866,671 B2 | 3/2005 | Tierney et al. |
| 6,994,703 B2 | 2/2006 | Wang et al. |
| 7,025,064 B2 | 4/2006 | Wang et al. |
| 7,025,761 B2 | 4/2006 | Wang et al. |
| 7,048,745 B2 | 5/2006 | Tierney et al. |
| 7,074,179 B2 | 7/2006 | Wang et al. |
| 7,090,448 B2 | 8/2006 | Stoll et al. |
| 7,118,582 B1 | 10/2006 | Wang et al. |
| 7,125,403 B2 | 10/2006 | Julian et al. |
| 7,176,399 B2 | 2/2007 | Graiger et al. |
| 7,249,602 B1 | 7/2007 | Emanuel |
| 7,331,967 B2 | 2/2008 | Lee et al. |
| 7,379,790 B2 | 5/2008 | Toth et al. |
| 7,524,320 B2 | 4/2009 | Tierney et al. |
| 7,549,992 B2 | 6/2009 | Shores et al. |
| 7,559,927 B2 | 7/2009 | Shores et al. |
| 7,658,740 B2 | 2/2010 | Shores et al. |
| 7,695,481 B2 | 4/2010 | Wang et al. |
| 7,747,311 B2 | 6/2010 | Quaid, III |
| 7,783,384 B2 | 8/2010 | Kraft |
| 7,865,266 B2 | 1/2011 | Moll et al. |
| 7,879,037 B2 | 2/2011 | Brunnett et al. |
| 7,947,050 B2 | 5/2011 | Lee et al. |
| 7,947,051 B2 | 5/2011 | Lee et al. |
| 7,953,509 B2 | 5/2011 | Murayama |
| 7,955,322 B2 | 6/2011 | Devengenzo et al. |
| 7,963,913 B2 | 6/2011 | Devengenzo et al. |
| 8,010,180 B2 | 8/2011 | Quaid et al. |
| 8,010,234 B2 | 8/2011 | Henne |
| 8,095,200 B2 | 1/2012 | Quaid, III |
| 8,123,740 B2 | 2/2012 | Madhani et al. |
| 8,142,447 B2 | 3/2012 | Cooper et al. |
| 8,170,717 B2 | 5/2012 | Sutherland et al. |
| 8,182,470 B2 | 5/2012 | Devengenzo et al. |
| 8,201,341 B2 | 6/2012 | Ferrari |
| 8,211,116 B2 | 7/2012 | Oostman, Jr. et al. |
| 8,226,072 B2 | 7/2012 | Murayama |
| 8,226,664 B2 | 7/2012 | Drews et al. |
| 8,277,474 B2 | 10/2012 | Norman et al. |
| 8,287,522 B2 | 10/2012 | Moses et al. |
| 8,288,670 B2 | 10/2012 | Nguyen |
| 8,333,588 B2 | 12/2012 | Putz et al. |
| 8,800,939 B2 | 8/2014 | Karsak et al. |
| 9,119,655 B2 | 9/2015 | Bowling et al. |
| 9,566,121 B2 | 2/2017 | Staunton et al. |
| 2002/0165549 A1 | 11/2002 | Owusu-Akyaw et al. |
| 2003/0181934 A1* | 9/2003 | Johnston .......... A61B 17/162 606/167 |
| 2004/0161723 A1 | 8/2004 | Helfenbein |
| 2004/0236352 A1 | 11/2004 | Wang et al. |
| 2005/0011740 A1 | 1/2005 | Graiger et al. |
| 2005/0149003 A1 | 7/2005 | Tierney et al. |
| 2005/0222714 A1 | 10/2005 | Nihei et al. |
| 2005/0228365 A1 | 10/2005 | Wang et al. |
| 2005/0234433 A1 | 10/2005 | Wang et al. |
| 2006/0011457 A1 | 1/2006 | Robertson |
| 2006/0053974 A1 | 3/2006 | Blust et al. |
| 2006/0178775 A1 | 8/2006 | Zhang et al. |
| 2007/0012135 A1 | 1/2007 | Tierney et al. |

(56) References Cited

U.S. PATENT DOCUMENTS

| | | |
|---|---|---|
| 2007/0021766 A1 | 1/2007 | Belagali et al. |
| 2007/0265653 A1 | 11/2007 | Suzuki |
| 2008/0208195 A1 | 8/2008 | Shores et al. |
| 2008/0211634 A1 | 9/2008 | Hopkins et al. |
| 2008/0228196 A1 | 9/2008 | Wang et al. |
| 2008/0262654 A1 | 10/2008 | Omori et al. |
| 2008/0281343 A1 | 11/2008 | Dewey et al. |
| 2009/0000626 A1 | 1/2009 | Quaid et al. |
| 2009/0000627 A1 | 1/2009 | Quaid et al. |
| 2009/0012531 A1 | 1/2009 | Quaid et al. |
| 2009/0012532 A1 | 1/2009 | Quaid et al. |
| 2009/0024142 A1 | 1/2009 | Ruiz Morales |
| 2009/0099520 A1 | 4/2009 | Millman et al. |
| 2009/0259412 A1 | 10/2009 | Brogardh |
| 2010/0041991 A1 | 2/2010 | Roundhill |
| 2010/0152533 A1 | 6/2010 | Mark |
| 2010/0152614 A1 | 6/2010 | Mark |
| 2010/0152615 A1 | 6/2010 | Mark et al. |
| 2010/0152756 A1 | 6/2010 | Mark |
| 2010/0152758 A1 | 6/2010 | Mark et al. |
| 2010/0152760 A1 | 6/2010 | Mark |
| 2010/0152761 A1 | 6/2010 | Mark |
| 2010/0152792 A1 | 6/2010 | Ralph et al. |
| 2010/0152795 A1 | 6/2010 | Mark |
| 2010/0168723 A1 | 7/2010 | Suarez et al. |
| 2010/0176925 A1 | 7/2010 | Tethrake et al. |
| 2010/0204713 A1 | 8/2010 | Ruiz Morales |
| 2010/0249817 A1 | 9/2010 | Mark |
| 2010/0331859 A1 | 12/2010 | Omori |
| 2011/0010012 A1 | 1/2011 | Murayama et al. |
| 2011/0015649 A1 | 1/2011 | Anvari et al. |
| 2011/0034930 A1 | 2/2011 | Buschmann et al. |
| 2011/0066161 A1 | 3/2011 | Cooper |
| 2011/0082462 A1 | 4/2011 | Suarez et al. |
| 2011/0087238 A1 | 4/2011 | Wang et al. |
| 2011/0160910 A1 | 6/2011 | Preisinger et al. |
| 2011/0213383 A1 | 9/2011 | Lee et al. |
| 2011/0218551 A1 | 9/2011 | Devengenzo et al. |
| 2012/0029354 A1 | 2/2012 | Mark et al. |
| 2012/0053606 A1 | 3/2012 | Schmitz et al. |
| 2012/0078279 A1 | 3/2012 | Mark |
| 2012/0089154 A1 | 4/2012 | Green et al. |
| 2012/0109150 A1 | 5/2012 | Quaid et al. |
| 2012/0109172 A1 | 5/2012 | Schmitz et al. |
| 2012/0130375 A1 | 5/2012 | Gillard et al. |
| 2012/0157879 A1 | 6/2012 | Mark et al. |
| 2012/0197182 A1 | 8/2012 | Millman et al. |
| 2012/0209314 A1 | 8/2012 | Weir et al. |
| 2012/0234126 A1 | 9/2012 | Gosselin et al. |
| 2012/0277663 A1 | 11/2012 | Millman et al. |
| 2012/0283706 A1 | 11/2012 | Blust |
| 2012/0296203 A1 | 11/2012 | Hartmann et al. |
| 2013/0060278 A1 | 3/2013 | Bozung et al. |
| 2013/0172903 A1 | 7/2013 | Suarez et al. |
| 2013/0268120 A1 | 10/2013 | Grygorowicz et al. |

FOREIGN PATENT DOCUMENTS

| | | |
|---|---|---|
| DE | 29716551 U1 | 4/1998 |
| DE | 10130897 C1 | 1/2003 |
| DE | 10130898 A1 | 1/2003 |
| DE | 10311455 B3 | 9/2004 |
| DE | 202007006801 U1 | 7/2007 |
| DE | 10200739384 A1 | 2/2009 |
| DE | 102010064389 A1 | 7/2012 |
| EP | 0456470 A1 | 11/1991 |
| EP | 0788865 A1 | 8/1997 |
| EP | 1605837 B1 | 4/2010 |
| FR | 871222 A | 4/1942 |
| FR | 2853272 A1 | 10/2004 |
| JP | H03114461 A | 5/1991 |
| JP | 2000515782 A | 11/2000 |
| JP | 2003275223 A | 9/2003 |
| WO | 2007002230 A1 | 1/2007 |
| WO | WO2007002230 A1 | 1/2007 |
| WO | 2011151544 A1 | 12/2011 |
| WO | 2013033566 A1 | 3/2013 |
| WO | WO2013033566 A1 | 3/2013 |

OTHER PUBLICATIONS

English language translation of DE29716551, downloaded from espacenet.com on Apr. 11, 2017. 12 pages.

English language abstract of DE10130897, downloaded from espacenet.com on Apr. 11, 2017. 18 pages.

English language abstract of DE10311455, downloaded from espacenet.com on Apr. 11, 2017. 23 pages.

English language abstract of DE102010064389, downloaded from espacenet.com on Apr. 11, 2017. 18 pages.

English language abstract for DE 101 30 897 extracted from www.espacenet.com on Sep. 17, 2014; 11 pages.

English language abstract and machine-assisted translation for DE10200739384 extracted from the espacenet.com database on Mar. 24, 2014, 18 pages.

English language abstract and machine-assisted translation for EP1605837 extracted from the espacenet.com database on Apr. 8, 2014, 32 pages.

English language abstract and machine-assisted translation for FR2853272 extracted from the espacenet.com database on Mar. 25, 2014, 24 pages.

International Congress and Symposium Series 223, Computer-assisted and Robotics Surgery by Brian Davies, New Horizons in Technology Medicine, edited by D. Ashton, 1997, 12 pages.

Machine-assisted English translation for FR 871 222 extracted from espacenet.com database on Apr. 11, 2018, 4 pages.

English language abstract for JP 2000-515782 extracted from espacenet.com database on Apr. 11, 2018, 1 page.

English language abstract and machine-assisted English translation for JP 2003-275223 extracted from espacenet.com database on Apr. 11, 2018, 23 pages.

Republic of China Office Action dated Apr. 26, 2017; 7 pages.

English language translation of CN1216454A, downloaded from espacenet.com on Jul. 26, 2017. 59 pages.

English language abstract and machine-assisted English translation for JPH 03-114461 extracted from espacenet.com database on Dec. 17, 2018, 10 pages.

English language abstract and machine-assisted English translation for DE 101 30 898 extracted from espacenet.com database on Jun. 10, 2019, 17 pages.

Machine-assisted English translation for DE 20 2007 006 801 extracted from espacenet.com database on Jun. 10, 2019, 14 pages.

\* cited by examiner

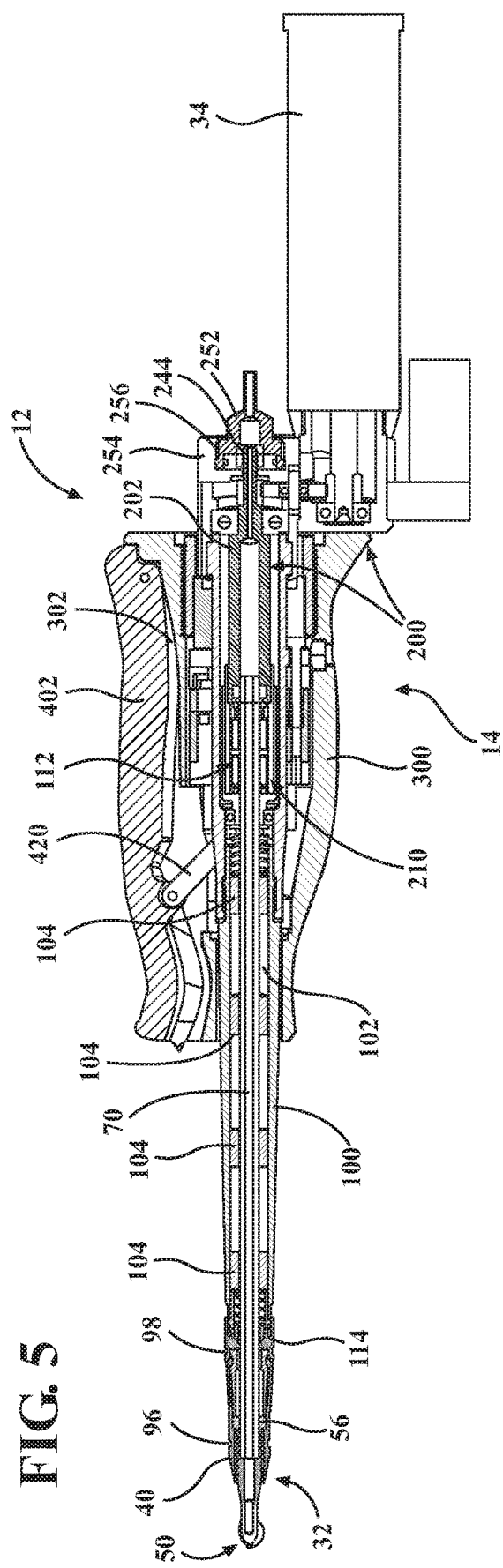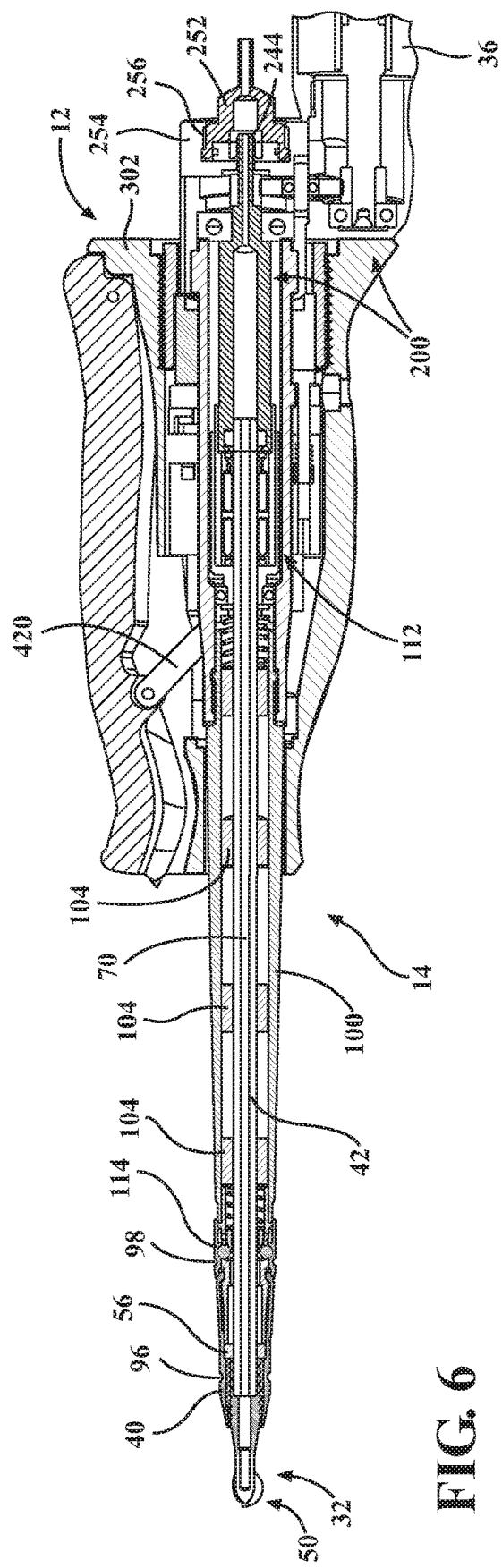

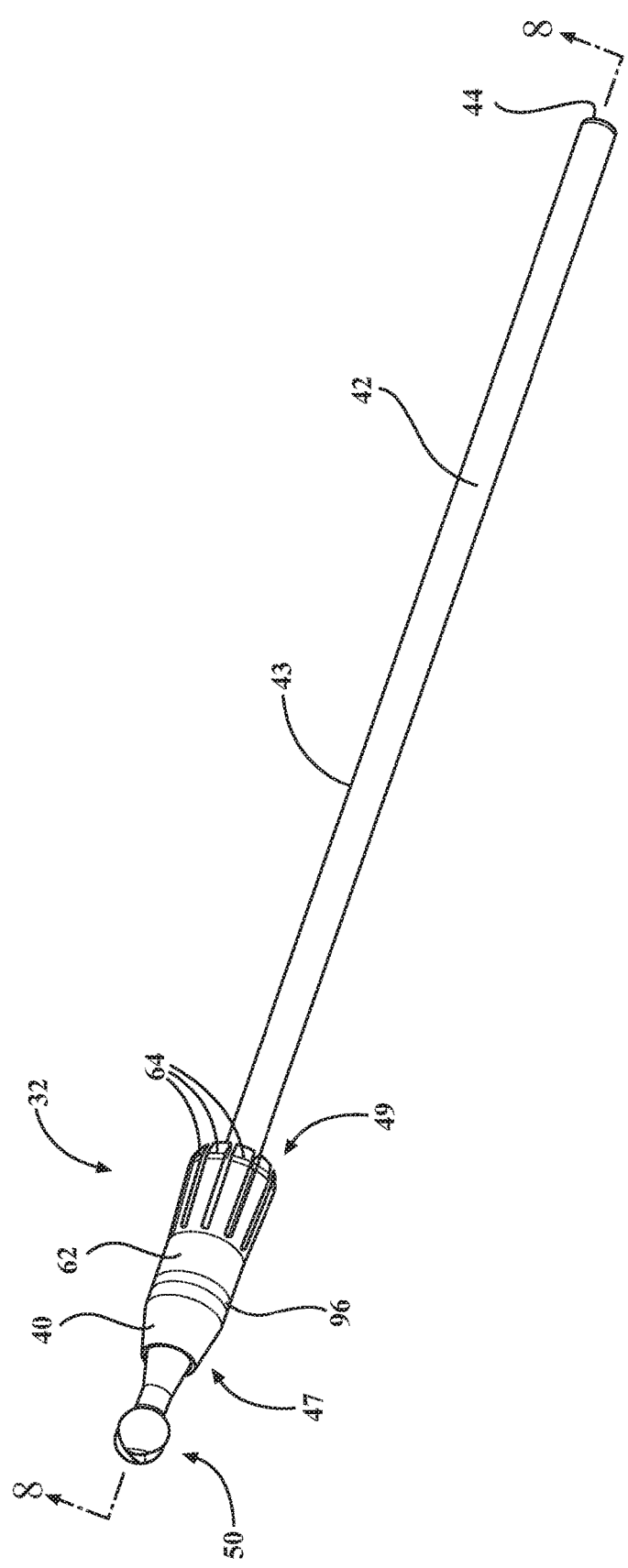
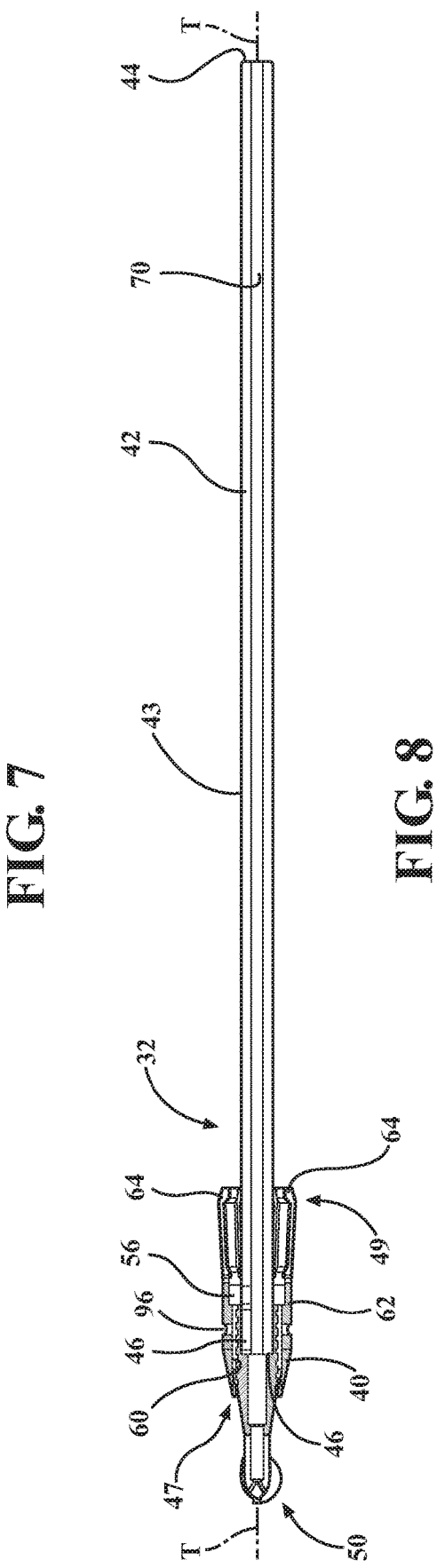
FIG. 7
FIG. 8

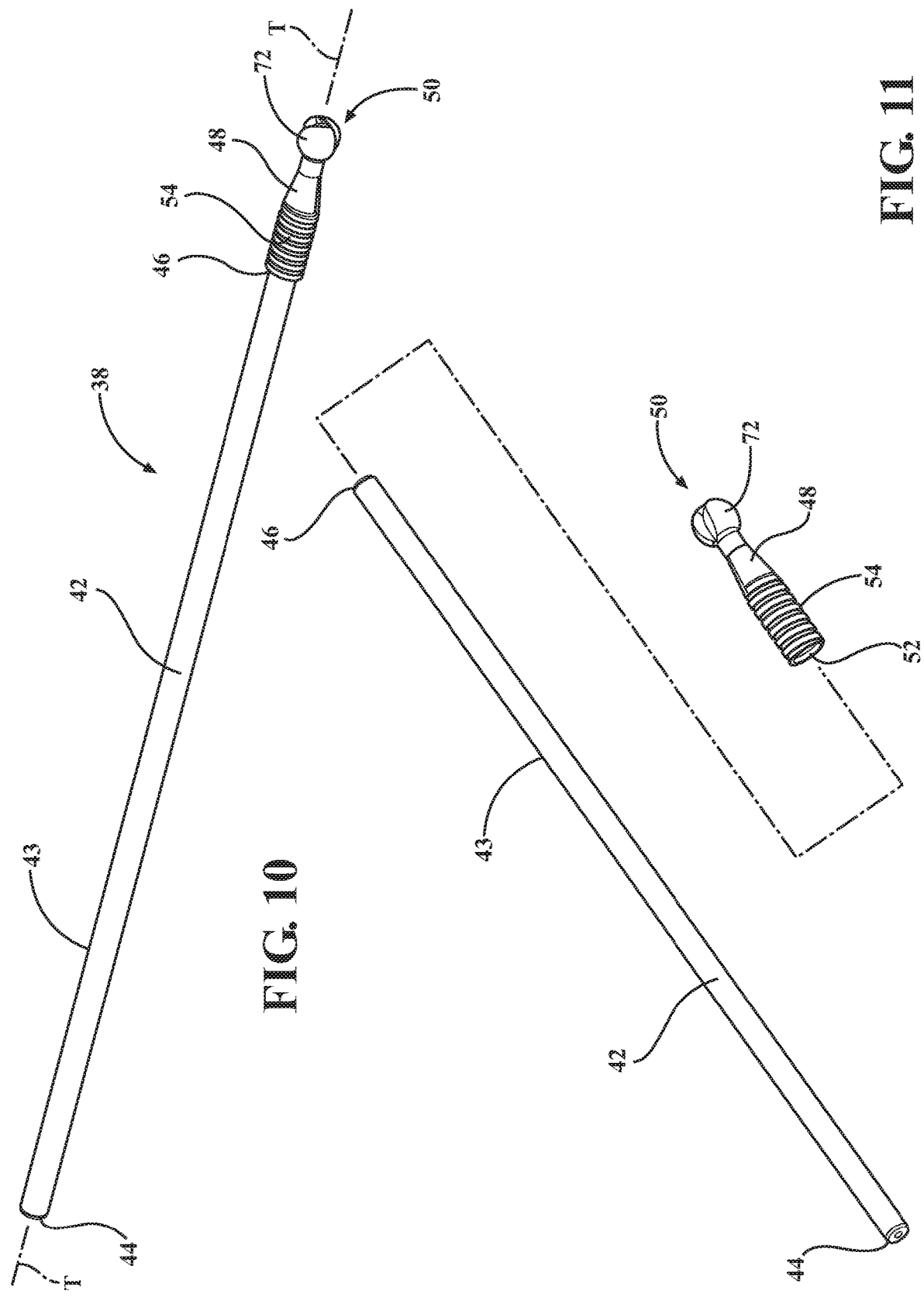

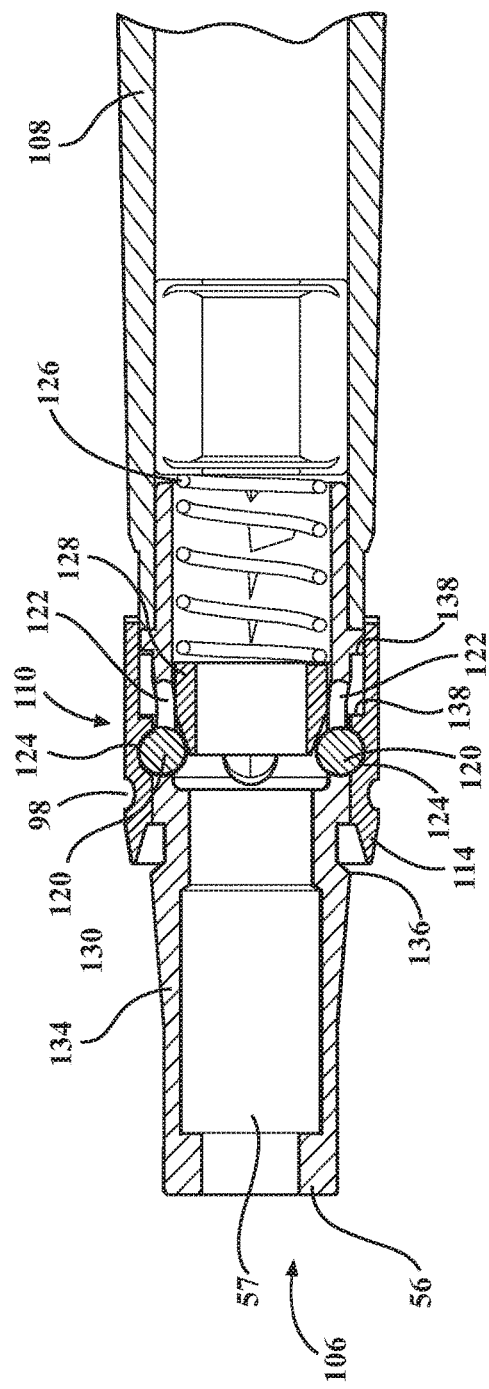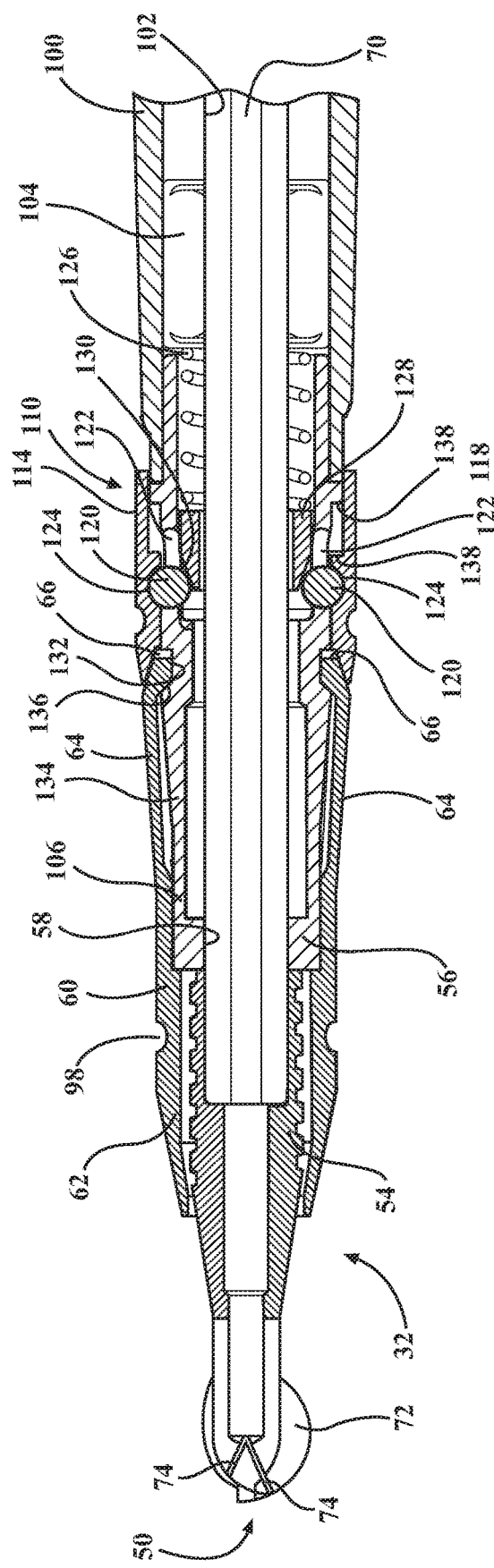

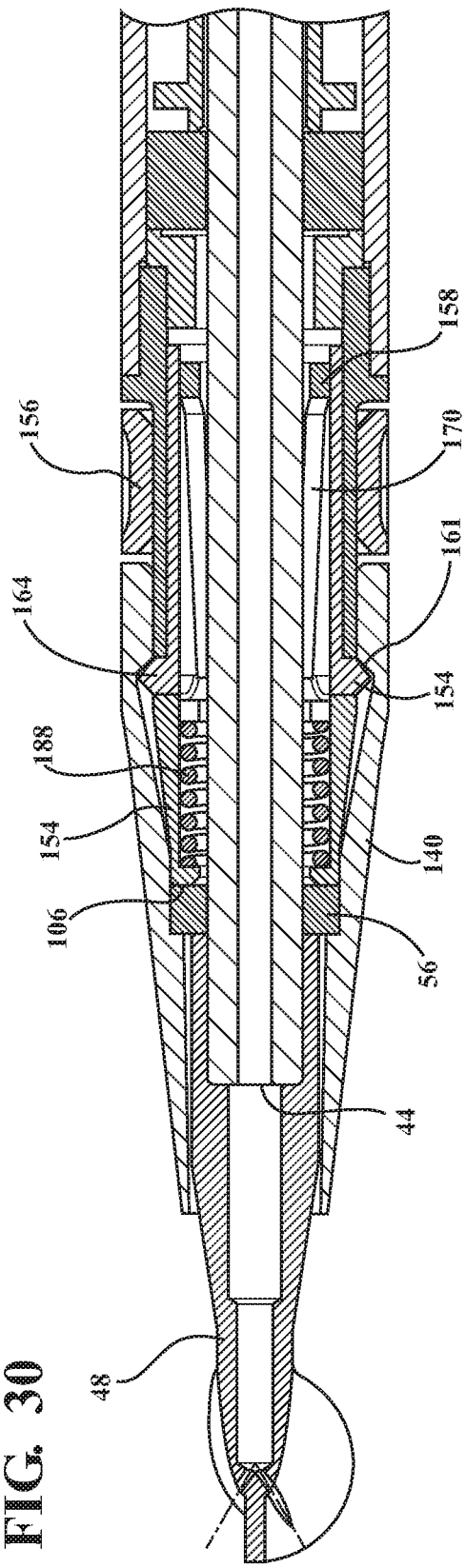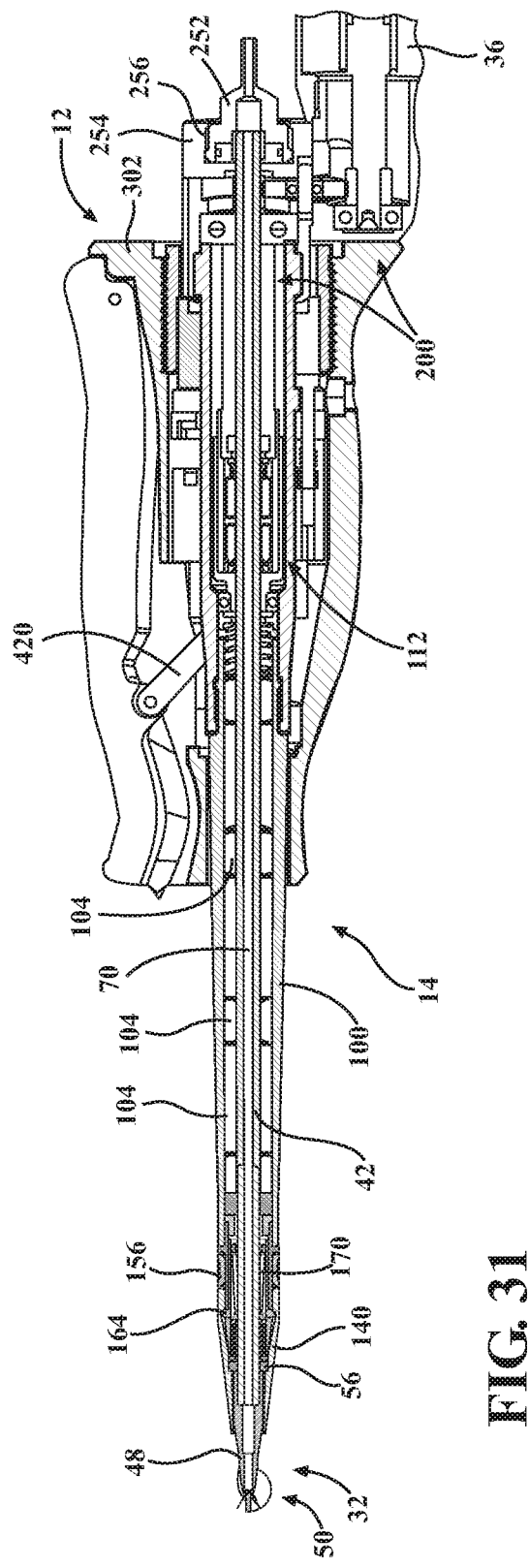
FIG. 30
FIG. 31

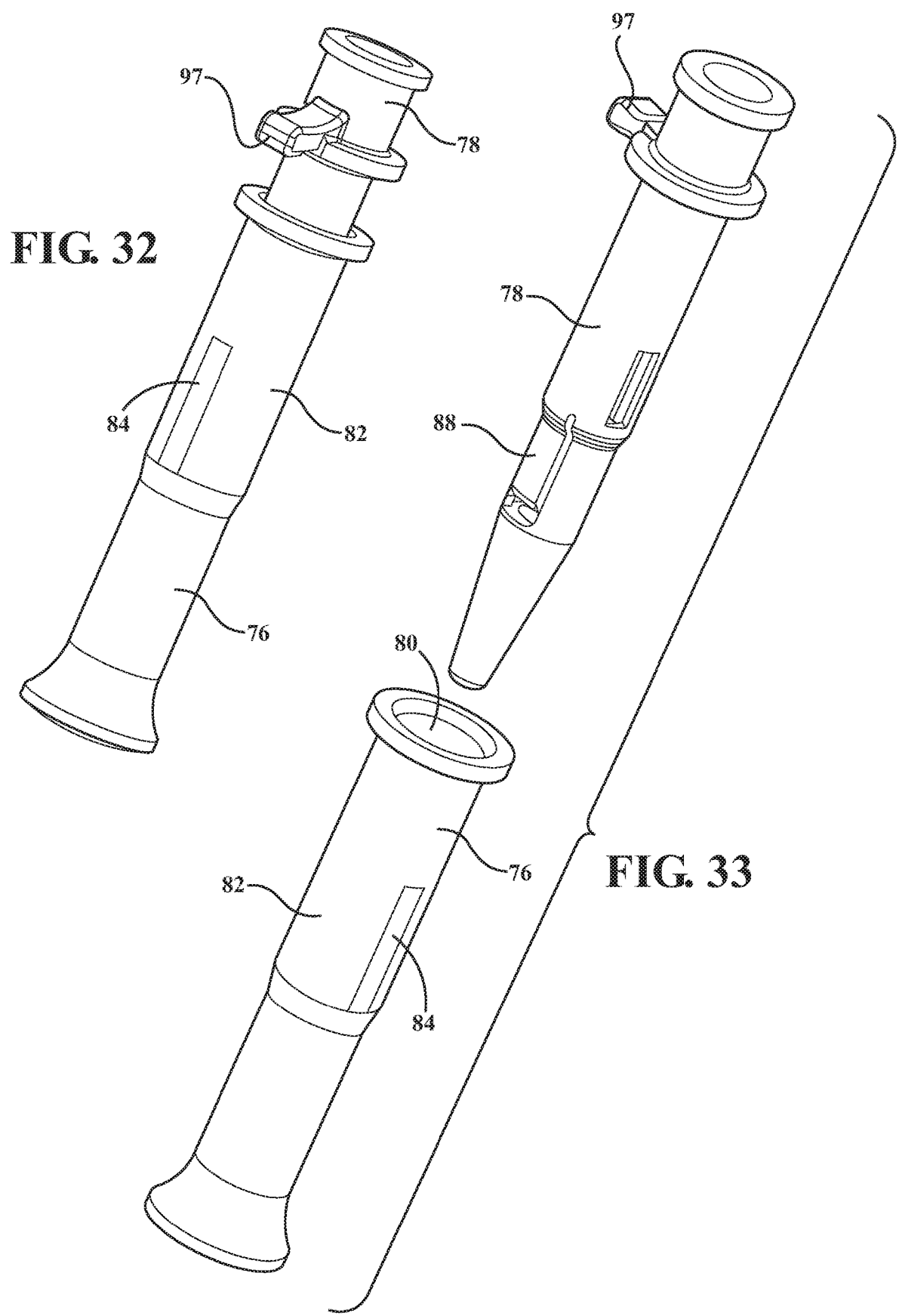

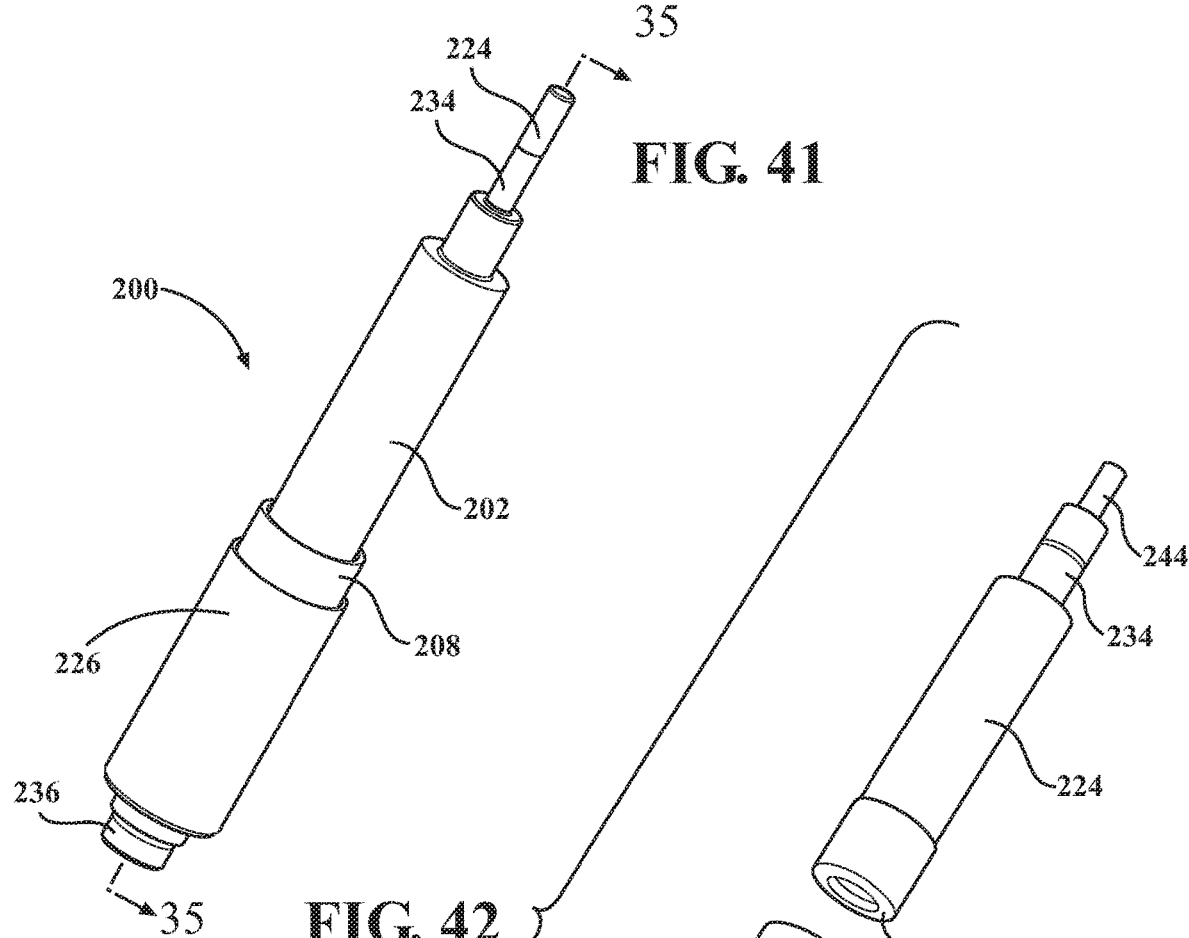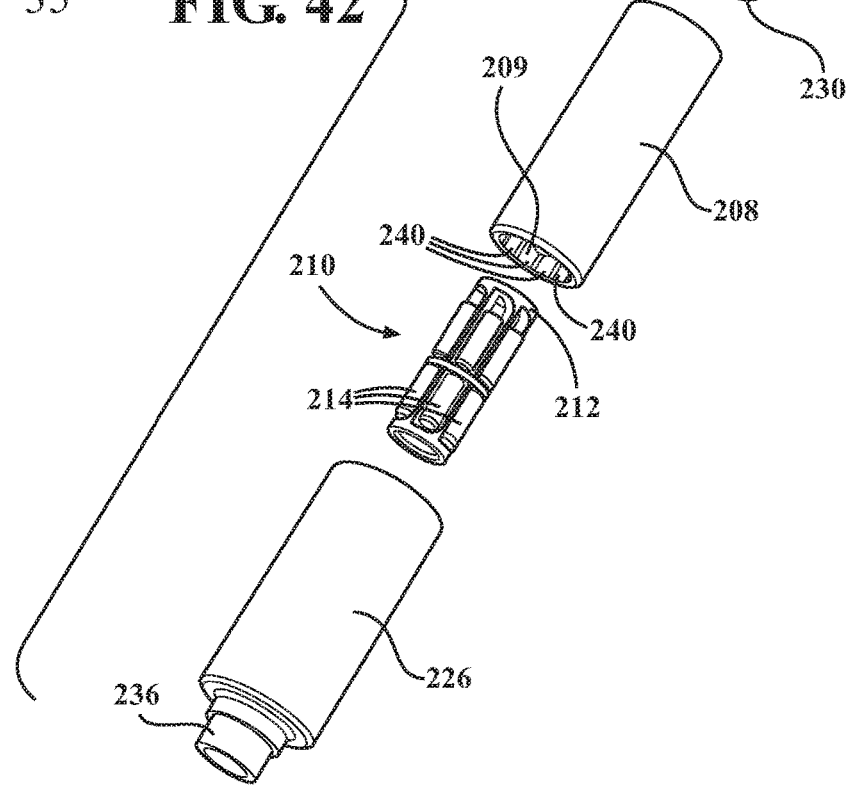

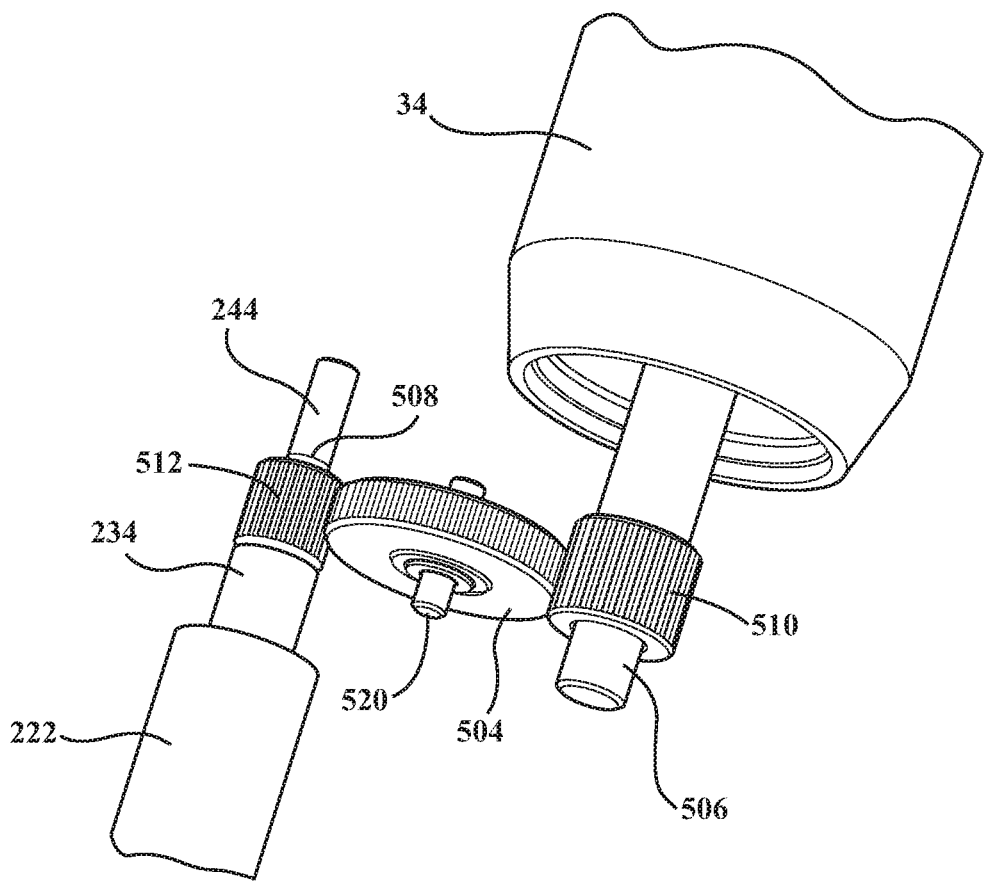
FIG. 81
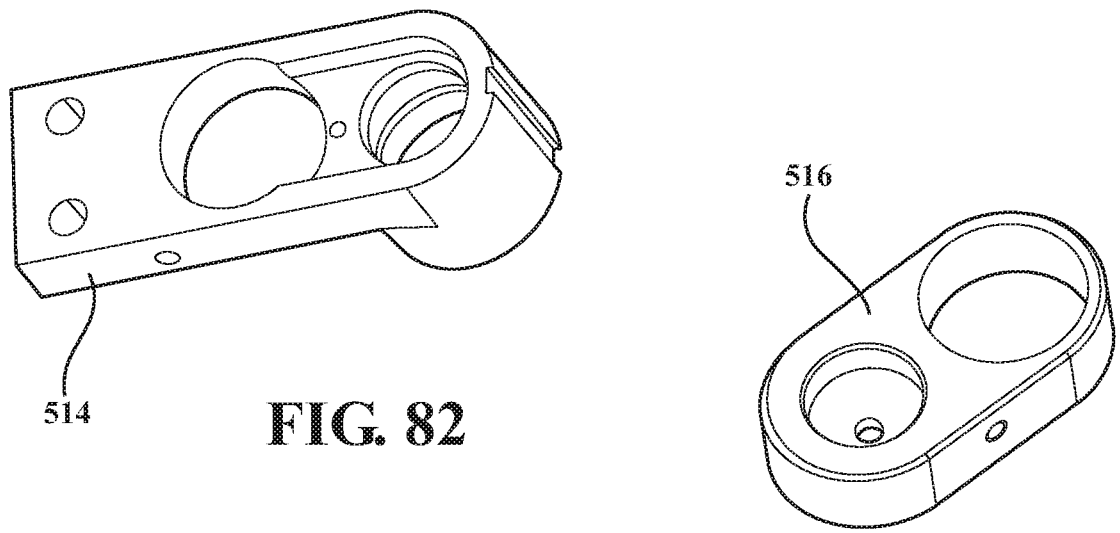
FIG. 82
FIG. 83

END EFFECTOR WITH LIQUID DELIVERY SYSTEM

CROSS-REFERENCE TO RELATED APPLICATIONS

This application is a continuation of U.S. patent application Ser. No. 14/214,703, filed on Mar. 15, 2014, which claims priority to and all the benefits of U.S. Provisional Patent Application No. 61/798,729 filed on Mar. 15, 2013, both of which are hereby incorporated herein by reference.

FIELD OF THE INVENTION

The present invention relates to an end effector and a liquid delivery system of the end effector for delivering liquid to a surgical site.

SUMMARY AND ADVANTAGES

The present invention provides an end effector that comprises a nose tube, a cutting accessory defining a bore, a drive system, and a cartridge. The drive system includes an actuator, a rotational drive member, and a drive connector. The rotational drive member is supported in the nose tube to be rotated relative to the nose tube by the actuator. The drive connector is coupled to the rotational drive member. The drive connector is configured to releasably engage the cutting accessory to rotate the cutting accessory. The rotational drive member defines a lumen to receive liquid from a liquid source. The lumen is configured to be in communication with the bore of the cutting accessory so that the bore is capable of delivering the liquid from the lumen to a surgical site. A first seal is configured to seal between the drive system and the cutting accessory. A cartridge is releasably coupled to the rotational drive member to deliver the liquid from the liquid source to the lumen of the rotational drive member. The cartridge includes a second seal configured to seal against the rotational drive member during rotation of the rotational drive member relative to the cartridge.

The present invention also provides an end effector that comprises a nose tube, a drive system, and a cartridge. The drive system includes an actuator, a rotational drive member, and a drive connector. The rotational drive member is supported in the nose tube to be rotated relative to the nose tube by the actuator. The drive connector is coupled to the rotational drive member. The drive connector is configured to releasably engage a cutting accessory to rotate the cutting accessory. The rotational drive member defines a lumen to receive liquid from a liquid source. The lumen is configured to be in communication with a bore of the cutting accessory so that the bore is capable of delivering the liquid from the lumen to a surgical site. A first seal is configured to seal between the drive system and the cutting accessory. A cartridge is releasably coupled to the rotational drive member to deliver the liquid from the liquid source to the lumen of the rotational drive member. The cartridge includes a second seal configured to seal against the rotational drive member during rotation of the rotational drive member relative to the cartridge.

The present invention also provides a liquid delivery system for an end effector to deliver liquid from a liquid source to a surgical site. The liquid delivery system comprises a cartridge configured to be releasably coupled to a housing of the end effector. The cartridge is also configured to receive the liquid from the liquid source. The cartridge includes a dynamic seal arranged to seal against a nipple of a rotational drive member when the cartridge is coupled to the housing and when the rotational drive member rotates relative to the cartridge such that the liquid is delivered from the liquid source, through the lumen of the rotational drive member, through a bore of a cutting accessory, and to the surgical site.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 5 is a cross-sectional view along line 5 in FIG. 3;

FIG. 6 is a magnified view of a portion of FIG. 5;

FIG. 7 is a perspective view of the cutting accessory;

FIG. 8 is a cross-sectional view along line 8 in FIG. 7;

FIG. 10 is a perspective view of a tool of the cutting accessory;

FIG. 11 is an exploded view of the tool including a shaft and an end piece;

FIG. 19 is a cross-sectional view along line 19 in FIG. 17;

FIG. 20 is a magnified view of a portion of FIG. 5;

FIG. 30 is a cross-sectional view of the cutting accessory assembled to a portion of the nose tube of FIG. 24;

FIG. 31 is a cross-sectional view of the cutting accessory assembled to the nose tube of FIG. 24;

FIG. 32 is a perspective view of a guard for the cutting accessory;

FIG. 33 is an exploded view of the guard;

FIG. 41 is a perspective view of a portion of the drive system;

FIG. 42 is an exploded view of a portion of the drive system including a drive connector;

FIG. 81 is a perspective view of the components in the gear box;

FIG. 82 is a perspective view of a base of the gear box;

FIG. 83 is a perspective view of a cover of the gear box;

DETAILED DESCRIPTION OF THE INVENTION

I. Overview

Figure 1:
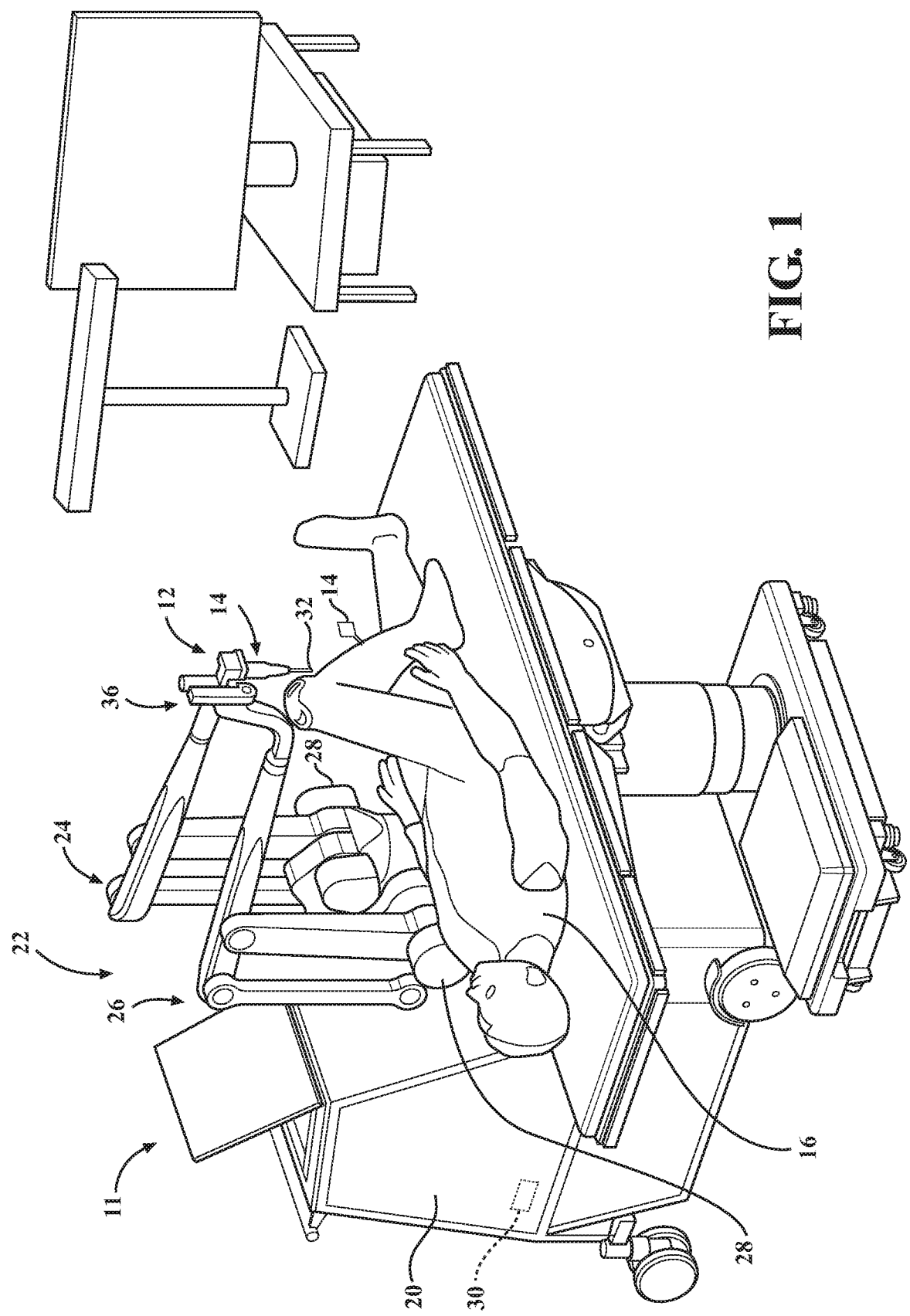
FIG. 1 is a perspective view of a robotic system including a manipulator having an end effector performing a surgical procedure on a patient.
Figure 2:
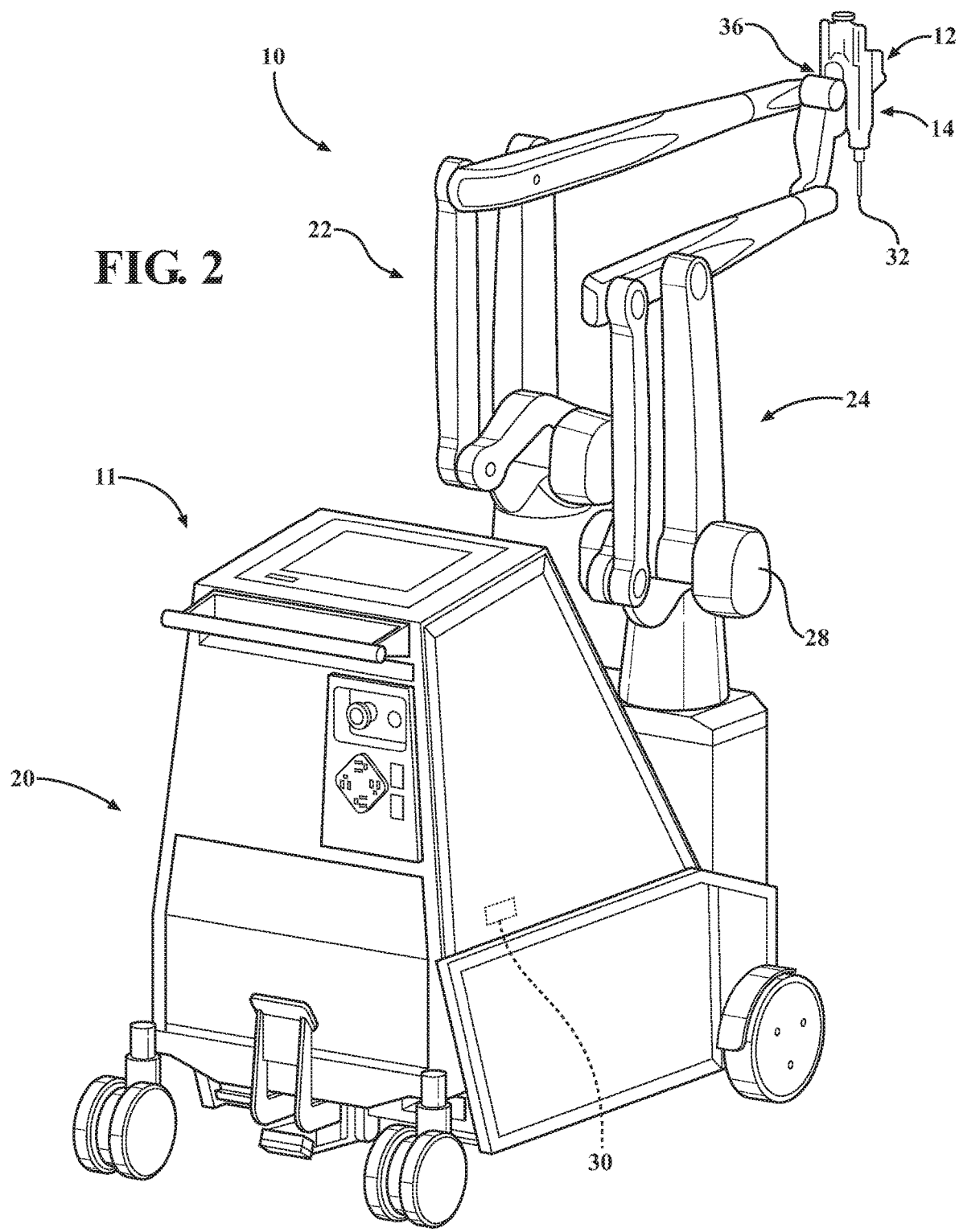
FIG. 2 is a perspective view of the manipulator.

With reference to FIGS. 1 and 2, a robotic surgical manipulator 10 includes an end effector 12. The manipulator 10 is part of a robotic system 11. The robotic system 11, for example, is a surgical robotic system as shown in FIGS. 1 and 2 and operates as set forth further below.

Figure 3:
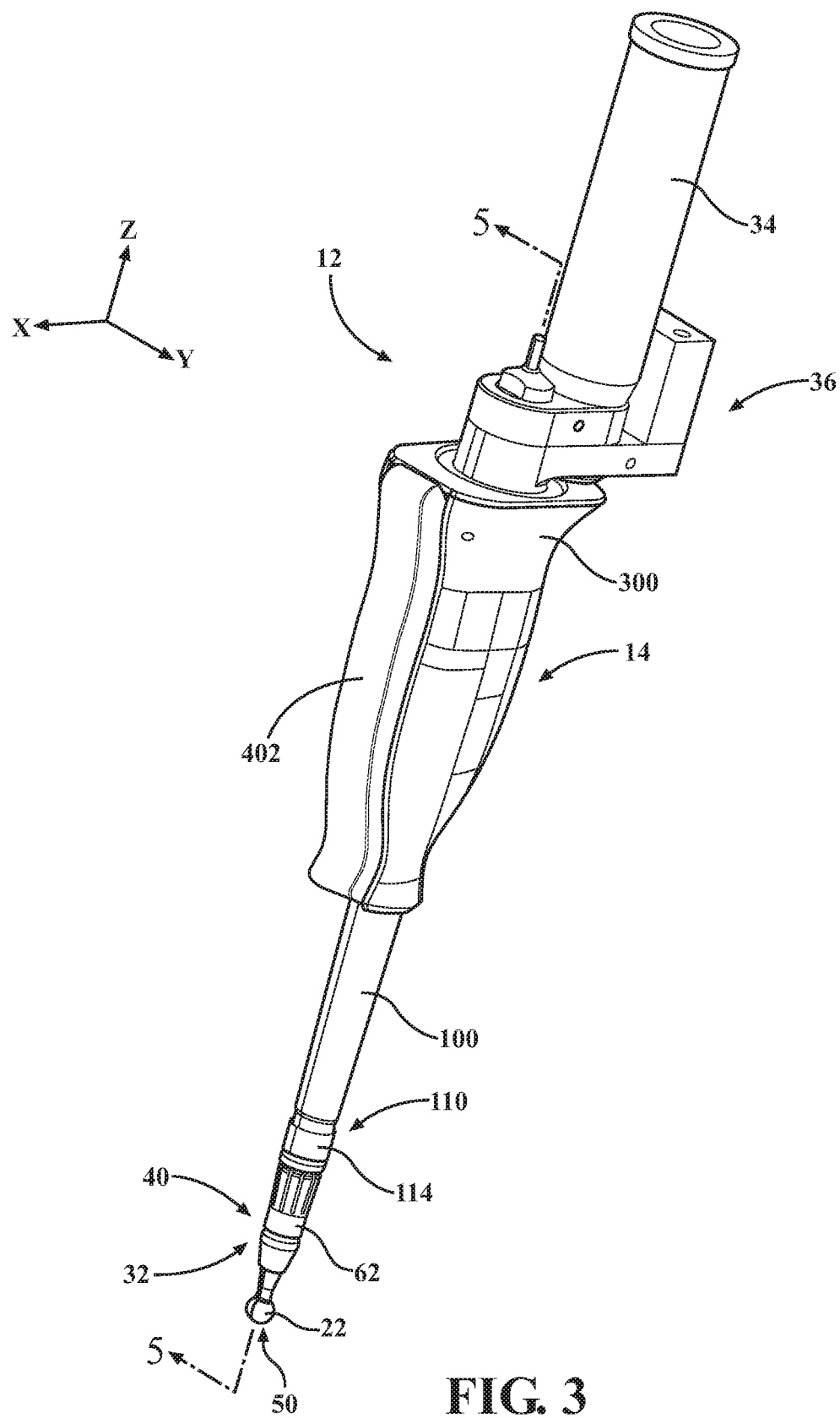
FIG. 3 is a perspective view of a portion of the end effector with a cutting accessory engaged with the end effector.
Figure 4:
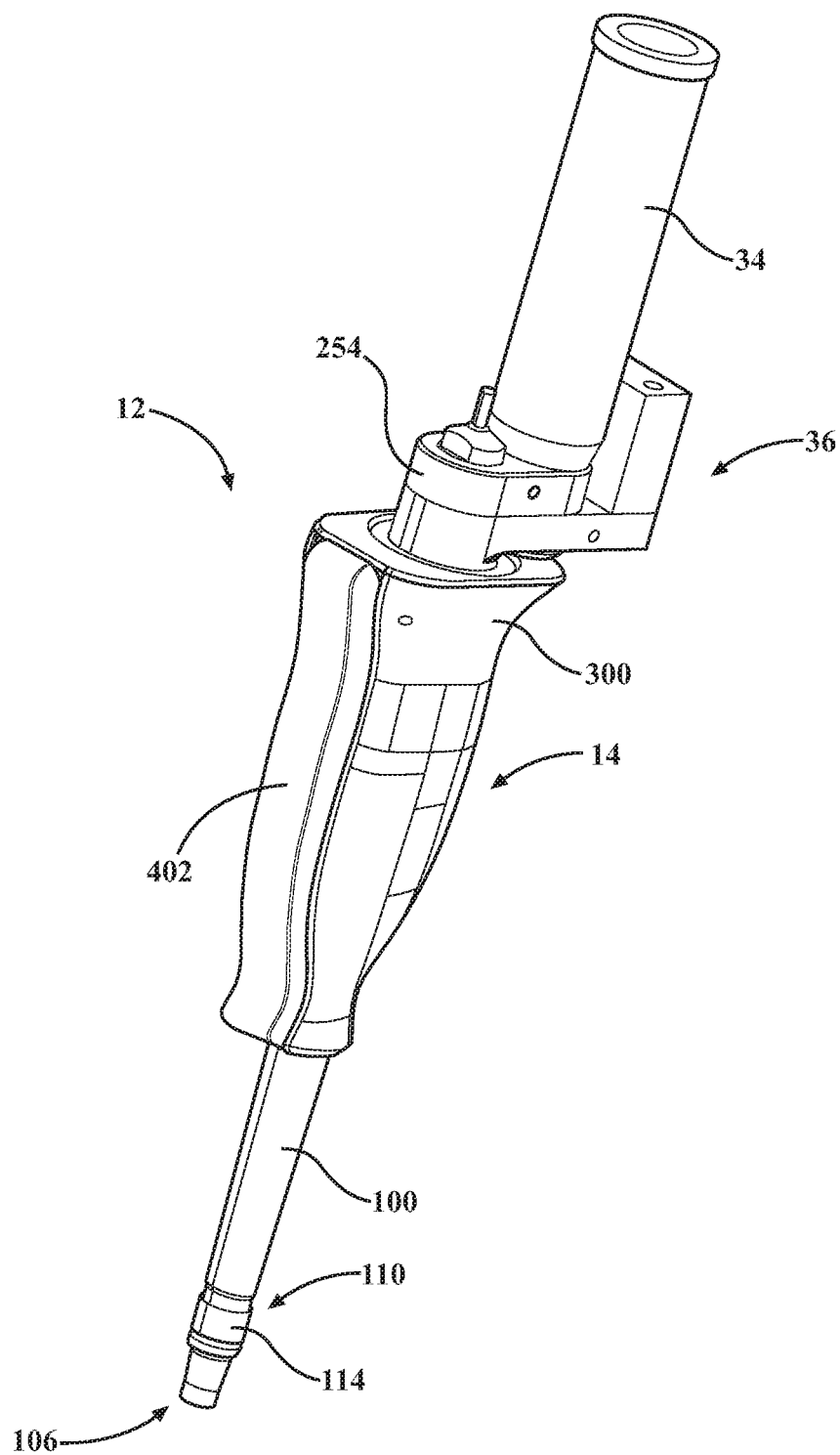
FIG. 4 is a perspective view of the end effector of FIG. 3 without the cutting accessory.

The end effector 12 is shown, for example, in FIGS. 3-5. The end effector 12 includes a surgical instrument 14. The manipulator 10 moves to apply the surgical instrument 14 to a patient 16. Specifically, the manipulator 10 moves to position and orient the surgical instrument 14 so that the surgical instrument 14 performs the intended medical/surgical procedure on the patient.

The robotic system 11 is used in conjunction with a surgical navigation system 18. The surgical navigation system 18 monitors the position of the end effector 12 and the patient 16. Based on this monitoring, the surgical navigation system 18 determines the position of the surgical instrument 14 relative to a site on the patient to which the instrument 14 is applied.

With continued reference to FIGS. 1 and 2, the robotic system 11 includes a mobile cart 20. The manipulator 10 includes a linkage assembly 22 that moveably connects the end effector 12 to the cart 20. Specifically, the end effector 12 includes a mounting fixture 36 connected to the linkage assembly 22.

The linkage assembly 22, for example, comprises a first parallel four bar link assembly 24 and a second parallel four bar link assembly 26. The position of each joint of each link assembly 24, 26 is set by an actuator 28. In FIG. 1, housings of the actuators 26 are identified. Each actuator 24, 26 is associated with a separate one of the link assemblies 24, 26.

A processor, referred to as manipulator controller 30, (partially shown as a phantom box in FIG. 1) is mounted to the cart 20. The manipulator controller 30 asserts the control signals that cause the actuators 28 to appropriately set the links of the link assemblies 24, 26. The manipulator controller 30 sets the positions of the links of the link assemblies 24, 26 based on a number of input signals. These signals include signals data from the surgical navigation system 18. These data provide information regarding the position of the instrument 14 relative to the surgical site to which the instrument 14 is applied.

The manipulator controller 30 selectively sets the position of the links of the link assemblies 24, 26 based on the forces and torques applied to the surgical instrument 14. These forces and torques are measured by a force/torque sensor (not numbered). The structure of the manipulator 10, including the manipulator controller 30, are set forth in more detail is U.S. Provisional Patent Application No. 61/679,258, entitled, "Surgical Manipulator Capable of Controlling a Surgical Instrument in either a Semi-Autonomous Mode or a Manual, Boundary Constrained Mode", the disclosure of which is hereby incorporated by reference.

The robotic system 11 can be operable in a manual mode. When the robotic system 11 operates in the manual mode, the robotic system 11 responds to force and torque that the operator asserts on the end effector 12 to position the instrument 14. In response to this force and torque, the linkage assembly 22 mechanically moves the instrument 14 in a manner that emulates the movement that would have occurred based on the force and torque applied by the operator. As the instrument 14 moves, the surgical robotic system 11 and surgical navigation system 18 cooperate to determine if the instrument is within a defined boundary. This boundary is within the patient and the navigation system 18 is configured to prevent the instrument 14 from operating outside of the defined boundary. Based on this data, the robotic system 11 selectively limits the movement of the linkage assembly 22, and thus the instrument 14. Specifically, the linkage assembly 22 constrains movement of the instrument 14 that would otherwise result in the application of the instrument 14 outside of the defined boundary. If the operator applies force and torque that would result in the advancement of the instrument 14 beyond the defined boundary, the linkage assembly 22 does not emulate this intended positioning of the instrument 14.

The robotic system 11 can be operable in a semi-autonomous mode. To operate the robotic system 11 in the semi-autonomous mode, a path of travel of the instrument 14 through tissue is generated. At least the basic version of this path is generated prior to the start of the procedure. The linkage assembly 22 advances the instrument 14 based on the generated path. When the instrument 14 is operated in the semi-autonomous mode, the linkage assembly does not advance the instrument 14 beyond the defined boundary.

The surgical instrument 14 is an instrument that the operator controls to perform the intended medical/surgical procedure. In some embodiments, the surgical instrument 14 includes a power generating unit that converts electrical signals into a form of energy that is applied to the patient. This energy may be mechanical, ultrasonic, thermal, RF, EM or photonic. When the surgical instrument 14 includes a power generating unit, the energy is applied to the surgical site through an energy applicator that extends from the surgical instrument 14. In the representative embodiment shown in the Figures, the surgical instrument 14 includes a cutting accessory 32 and an actuator 34 coupled to the cutting accessory 32 for driving the cutting accessory 32.

II. Cutting Accessory

The cutting accessory 32 is removably engaged with the rest of the end effector 12. FIGS. 3, 5, and 6, for example, show the cutting accessory 32 engaged with the rest of the end effector 12 and FIG. 4 shows the end effector 12 without the cutting accessory 32. The tool 38 is configured to remove tissue from target tissue of the patient. As shown in the Figures, the tool 38, for example, is a bur. In the alternative to a bur, the tool 38 can be any type of surgical tool for material cutting and/or material removal in the surgical site.

Figure 9:
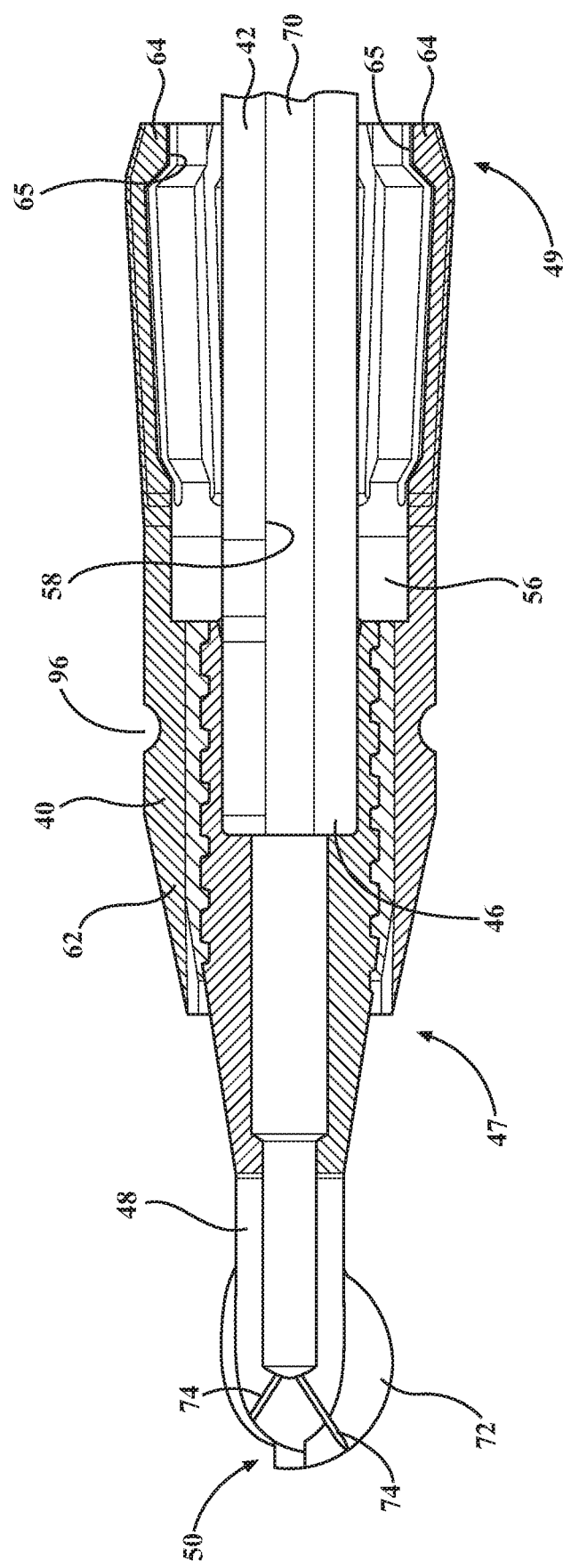
FIG. 9 is a magnified view of a portion of FIG. 8.
Figure 12:
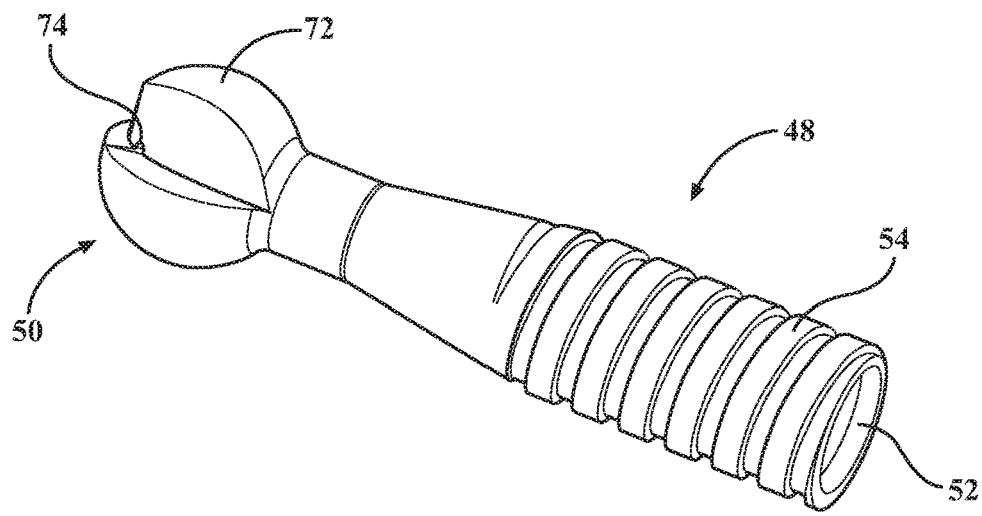
FIG. 12 is a perspective view of the end piece.
Figure 13:
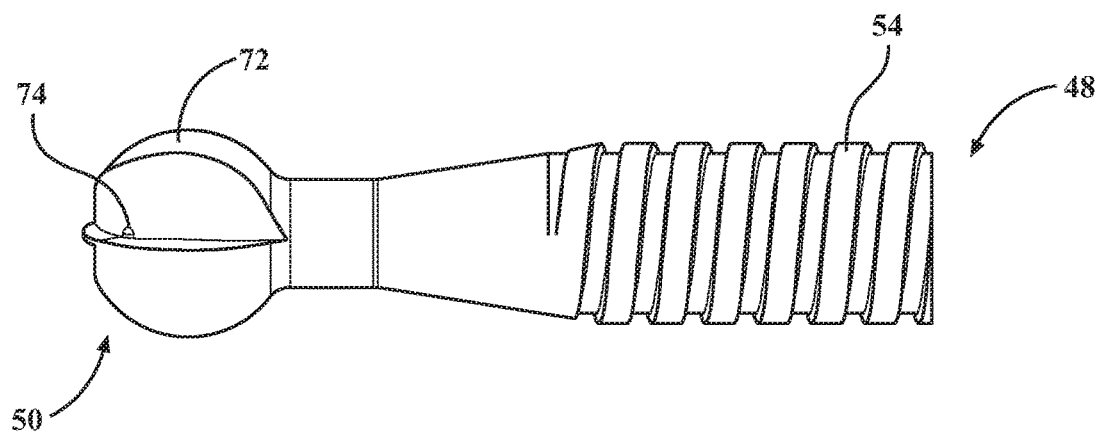
FIG. 13 is a side view of the end piece.
Figure 14:
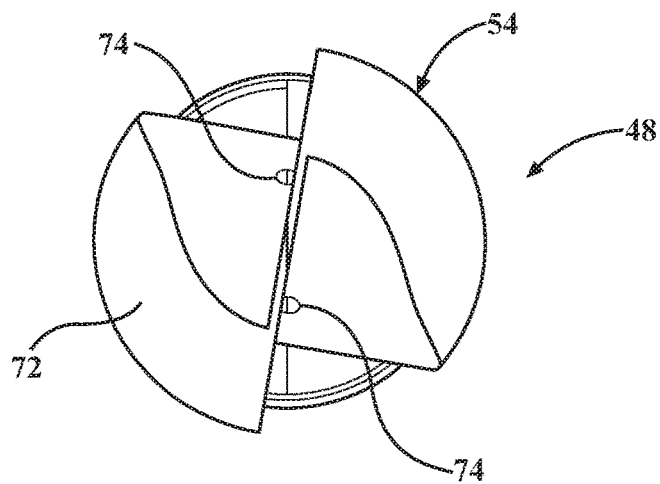
FIG. 14 is an end view of the end piece.
Figure 24:
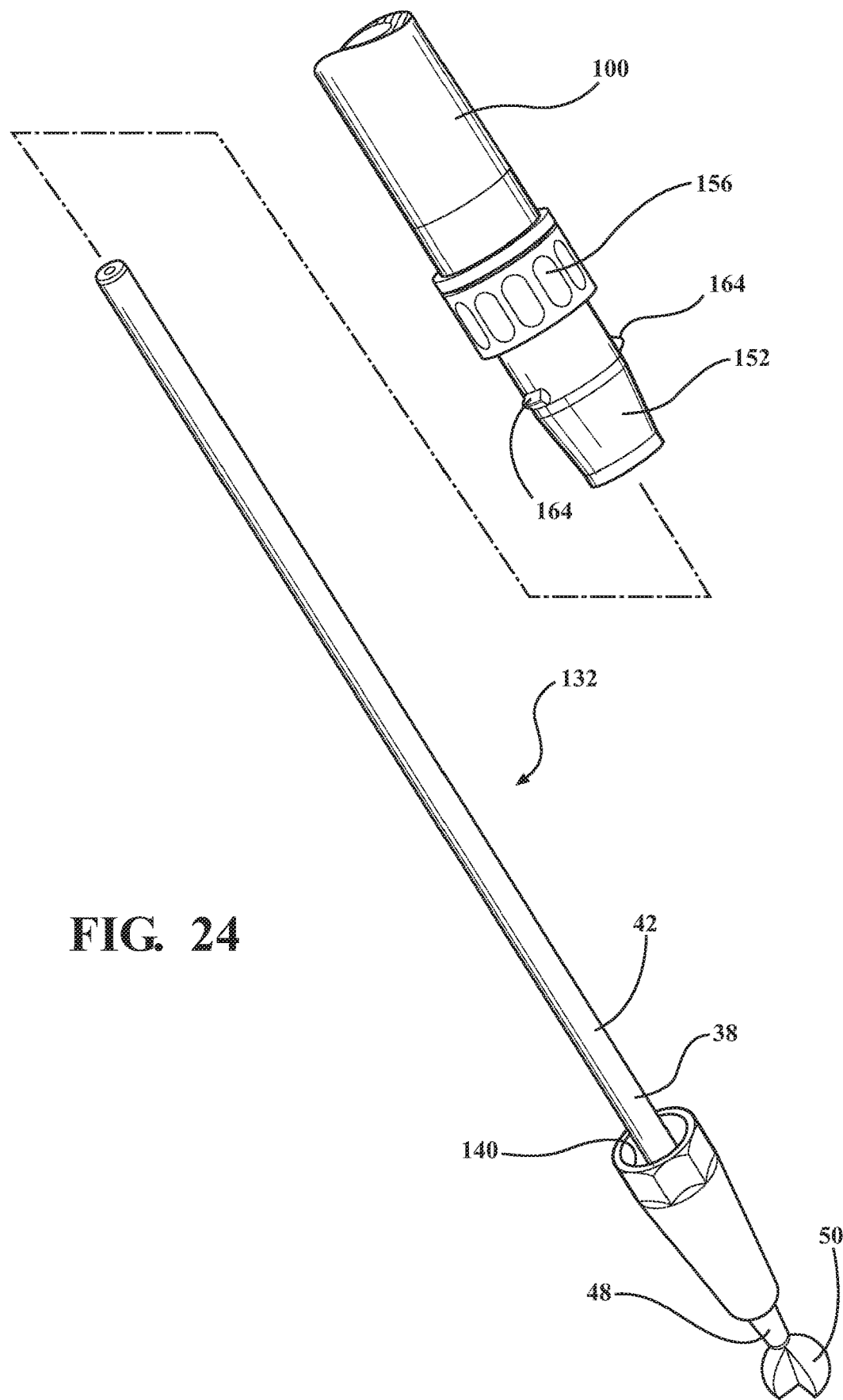
FIG. 24 is a perspective view of another embodiment of the cutting accessory and another embodiment of the axial connector supported on the nose tube.
Figure 25:
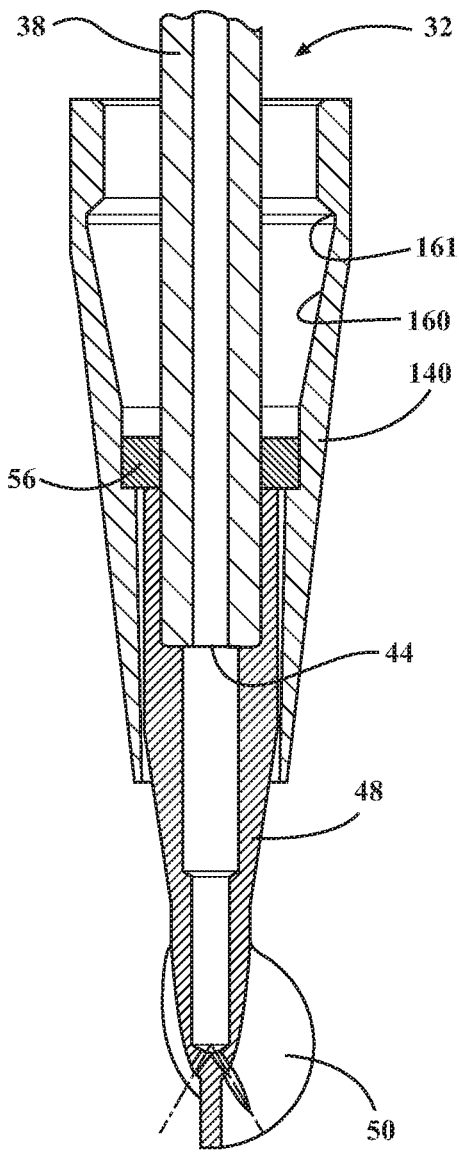
FIG. 25 is a cross-sectional view of a portion of the cutting accessory of FIG. 24.

With reference to FIGS. 7-9, the cutting accessory 32 includes a tool 38 and a shroud 40, 140 coupled to the tool 38. Specifically, the cutting accessory 32 including one embodiment of the shroud 40 is shown in FIGS. 7-9 and, alternatively, the cutting accessory 32 including another embodiment of the shroud 140 is shown in FIGS. 24-25.

With reference to FIGS. 10-14, the tool 38 includes a shaft 42, extending along a tool axis T between a proximal end 44, i.e., a free end 44, and a distal end 46, and an end piece 48 fixed to the distal end 46 of the shaft 42. The shroud 40, 140 is rotatably coupled to the shaft 42. The tool 38 is typically 50-200 mm long. For example, the tool 38 can be 160 mm long. The shaft 42 of the tool 38 is typically 2.5-6.0 mm in diameter. For example, the shaft 42 can be 4 mm in diameter.

The tool 38 includes a cutting tip 50 for cutting target tissue of the patient 16. Specifically, the end piece 48 presents the cutting tip 50.

The end piece 48, for example, defines a cavity 52 that receives the distal end 46 of the shaft 42. The end piece 48 can be fixed to the shaft 42 in any fashion such as, for example, friction fit, adhesive, snap-ring, welding, etc. Alternatively, for example, the end piece 48 is integrally formed with the shaft 42, i.e., the end piece 48 and the shaft 42 are formed together as a unitary part.

The end piece 48 defines threads 54 adjacent the tool 38. The threads 54, along with an end of the end effector 12, create an Archimedean screw for pushing debris, e.g., cut tissue, bodily liquid, and/or irrigation liquid, away from the end effector 12.

The tool 38 shown in the Figures is a bur, as set forth above, and the cutting tip 50 of the bur is a cutting head 72. The cutting head 72 can be of any size, shape, and configuration without departing from the nature of the present invention.

The shroud 40, 140 is rotatably engaged to the tool 38 and is axially fixed relative to the tool 38 along the tool axis T. The shroud 40 is rotatable about the tool axis T.

With reference to FIGS. 8 and 9, a bearing 56 is disposed between the tool 38 and the shroud 40, 140 and is fixed to the tool 38 and to the shroud 40, 140 along the tool axis T. Specifically, the bearing 56 defines a bore 58. The bearing 56 receives the shaft 42 in the bore 58 and is connected to the shaft 42 with a friction fit, i.e., an inner diameter of the bore 58 and the outer diameter of the shaft 42 are sized and shaped such that the bearing 56 is secured to the shaft 42 by friction between the inner diameter of the bearing 56 and the outer diameter of the shaft 42. The friction fit is typically accomplished by pressing the bearing 56 onto the shaft 42. The shroud 40, 140 receives the bearing 56 and is connected to the bearing 56 with a friction fit. Specifically, the shroud 40, 140 defines an inside surface 60 and an outside diameter of the bearing 56 is friction fit to the inside surface 60.

Figure 15:
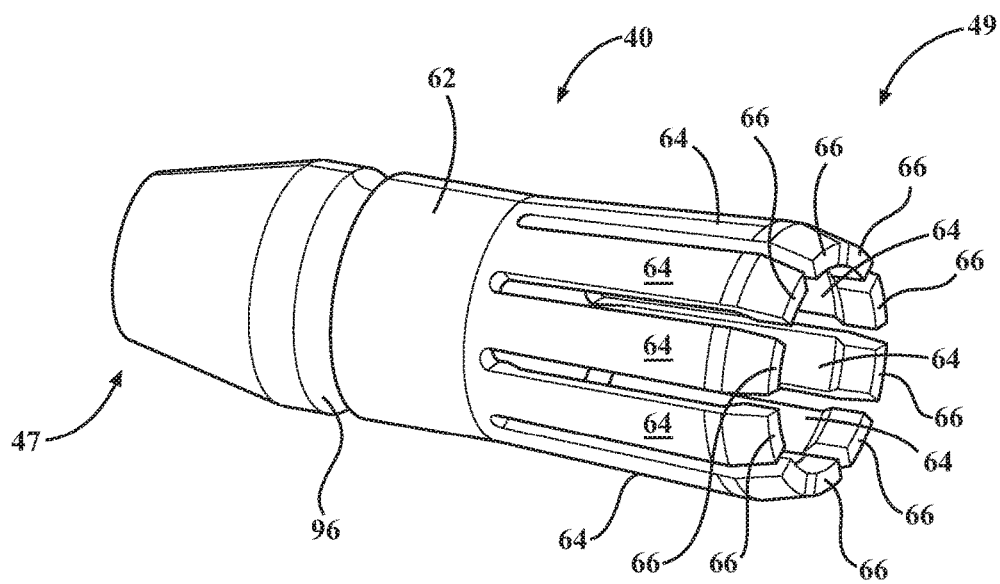
FIG. 15 is a perspective view of a shroud of the cutting accessory.
Figure 16:
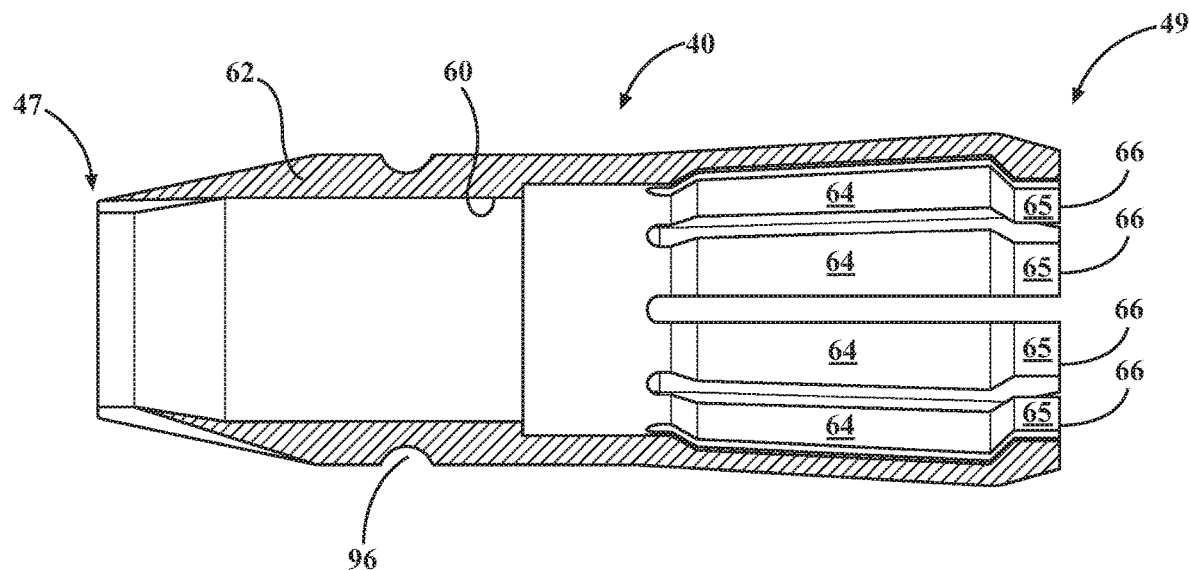
FIG. 16 is a cross-sectional view of the shroud.
Figure 17:
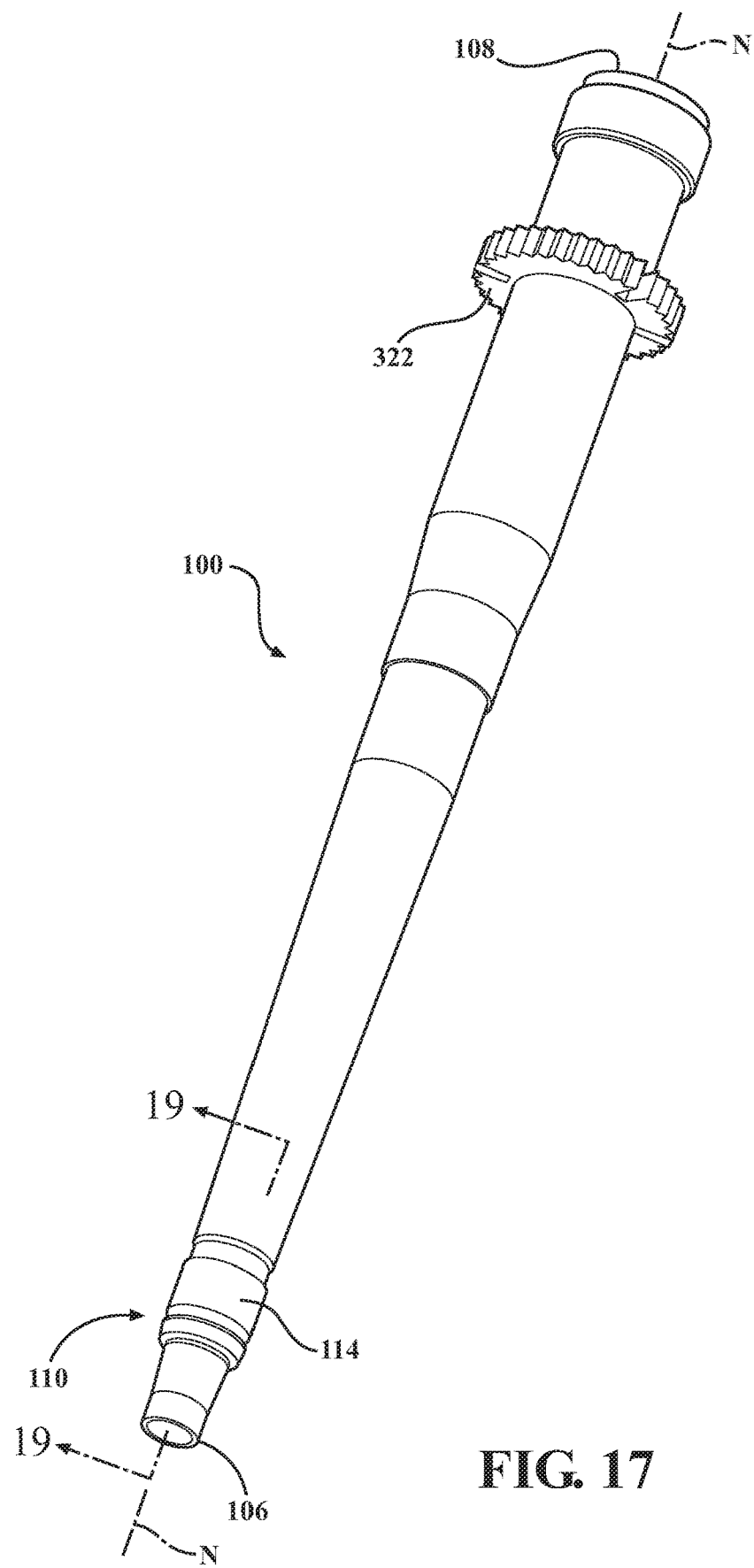
FIG. 17 is a perspective view of a nose tube of the end effector.
Figure 18:
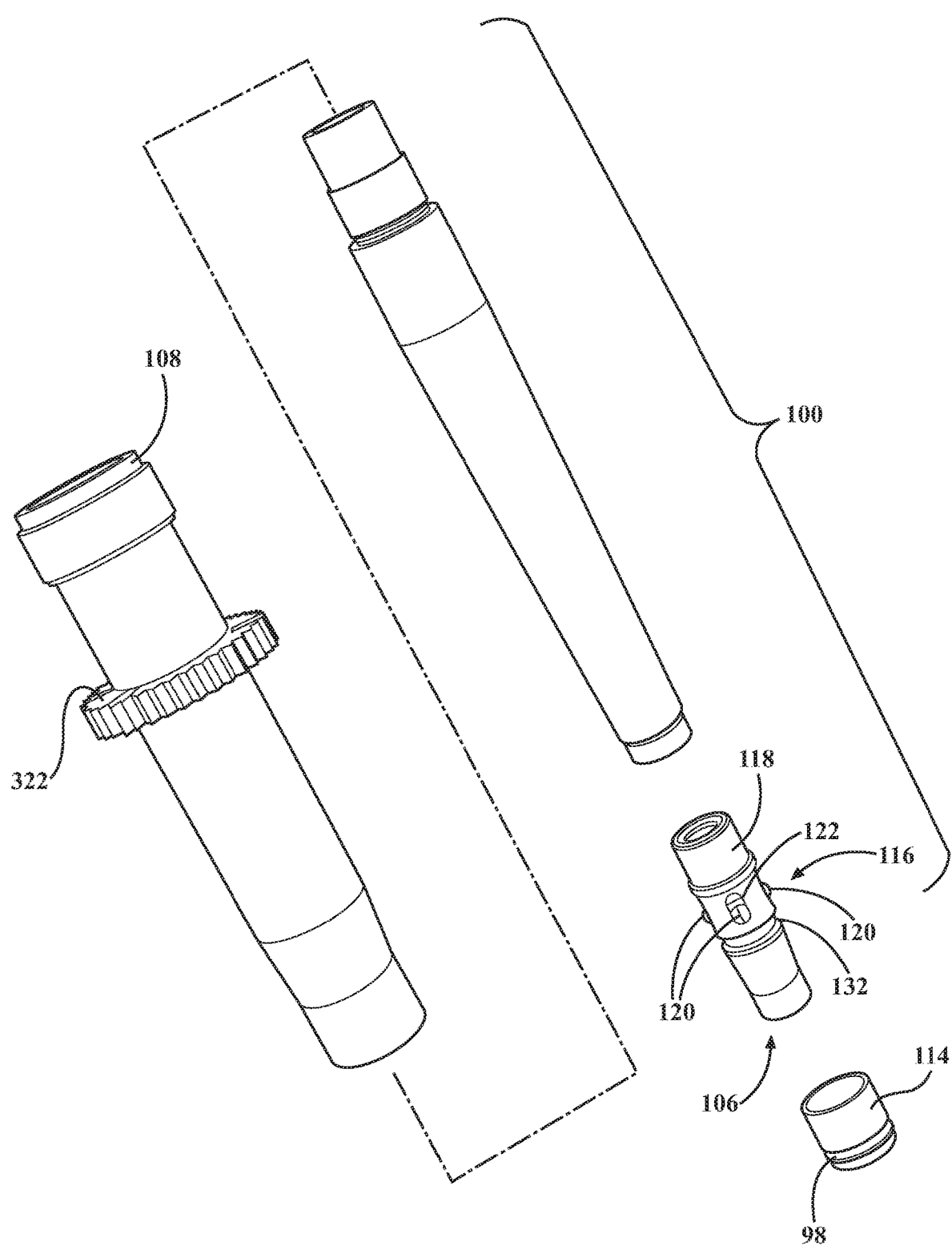
FIG. 18 is an exploded view of the nose tube.

With reference to FIGS. 15 and 16, the shroud 40 is generally cylindrical in shape. The shroud 40 includes a body portion 62, i.e., a base 62, that presents the inside surface 60. At least one finger 64 extends from the body portion 62. The shroud 40 shown in the Figures, for example, includes several fingers 64 that extend from the body portion 62. The fingers 64 are circumferentially spaced from each other about the tool axis T. The fingers 64 each include a tip 66 that tapers, e.g., angles inwardly toward the tool axis T. The fingers 64 are flexible relative to the body portion 62, as discussed further below.

With reference to FIGS. 24 and 25, the shroud 140 presents an inside surface 160 and a groove 161 along the inside surface 160. The groove 161 typically extends circumferentially about the inside surface 160.

With reference to FIGS. 32-38, the cutting accessory 32 includes a guard 68. The guard 68 covers the cutting tip 50 while the cutting accessory 32 is being handled 300 and/or when the cutting accessory 32 is mounted to the end effector 12 and not in use. As set forth further below, the guard 68 can support identification features, e.g., a memory chip or RFID chip, to identify parameters of the cutting accessory 32 to the manipulator controller 30. As also set forth below, the guard 68 can be configured to aid in engagement and disengagement of the cutting accessory 32 with respect to the end effector 12.

The cutting accessory 32 is configured to receive liquid and deliver the liquid to the surgical site during cutting. The liquid typically flows through the tool 38, e.g., the shaft 42 and the end piece 48, to the surgical site. The liquid can serve several functions. For example, the liquid can cool the cutting tip and/or cools and irrigates the surgical site, can lubricate the interface between the cutting tip 50 and the tissue in contact with the cutting tip 50 to reduce heat production at the interface; can clear cut tissue and/or bodily fluid; and/or can cool the shaft 42 of the tool 38 to draw heat from bearings 104 in nose tube 100. The liquid is, for example, an irrigation solution such as, for example, saline solution. Alternatively, the liquid can be of any type to cool and/or irrigate a surgical cutting accessory 32 and/or tissue in a surgical site without departing from the nature of the present invention.

With reference to FIGS. 7 and 8, the shaft 42 of the tool 38 defines a bore 70 that extends along the tool axis T for transferring the liquid. The liquid is delivered to bore 70 at the proximal end 44 of the tool 38, as set forth further below, and the liquid flows from the proximal end 44 to the distal end 46.

With reference to FIGS. 9-14, the cutting head 72 defines at least one port 74 in communication with the bore 70 of the shaft 42. The cutting head 72 typically defines the cavity 52 between the bore 70 of the shaft 42 and the ports 74. The ports 74 extend through the cutting head 72 to deliver the fluid from the bore 70 of the shaft 42 to the surgical site. The ports 74 extend relative to the tool axis T at an angle designed to deliver the fluid on the surgical site without spraying at staff in the operating room. The ports 74 also extend relative to the tool axis T at an angle designed to prevent the fluid from being aimed generally perpendicular to the surgical site to prevent cavitation at the surgical site caused by the fluid. For example, the ports 74 typically extend relative to the tool axis T at an angle of between 0° and 45°. The ports 74 typically have a diameter of 0.25 mm-0.50 mm.

III. End Effector

With reference to FIGS. 17-31, the end effector 12 includes a nose tube 100 that supports the cutting accessory 32 when the cutting accessory 32 is engaged with the end effector 12. The nose tube 100 defines a nose tube bore 102 and receives the shaft 42 of the cutting accessory 32 in the nose tube bore 102. The nose tube 100 releasably engages and rotatably supports the cutting accessory 32 in the nose tube bore 102. Typically at least one bearing 104, shown for example in FIGS. 5, 6, and 20, is disposed in the nose tube bore 102 and the bearing 104 is configured to receive and rotatably support the shaft 42 in the nose tube bore 102.

The nose tube 100 is fixed relative to the mounting fixture 36. The nose tube 100 extends along a nose tube axis N between a distal end 106, i.e., a terminal end 106 along the tube axis N, and a proximal end 108 of the nose tube 100. The nose tube 100 shown in the Figures includes a plurality of segments disposed along the nose tube axis N and the segments are fixed to one another. Alternatively, the nose tube 100 is formed of a single piece or is formed of any number of segments without departing from the nature of the present invention.

The end effector 12 includes an axial connector 110, 150 for axially engaging the cutting accessory 32 to the end effector 12 and a drive connector 112 for rotationally engaging the cutting accessory 32 to the end effector 12. Specifically, one embodiment of the axial connector 110 is shown in FIGS. 19-23 and another embodiment of the axial connector 150 is shown in FIGS. 24-31. The axial connector 110 of FIGS. 19-23 is configured to releasably engage the embodiment of the cutting accessory 32 that includes the shroud 40. The axial connector 150 of FIGS. 24-31 is configured to releasably engage the embodiment of the cutting accessory 32 that includes the shroud 140.

The axial connector 110, 150 is disposed along the nose tube axis N between the terminal end 106 and the drive connector 112. The axial connector 110, 150 and the drive connector 112 are disposed about the nose tube axis N.

As set forth further below, the axial connector 110, 150 is supported by the nose tube 100 and is configured to lock the cutting accessory 32 relative to the nose tube 100 along the nose tube axis N. As also set forth further below, the drive connector 112 is configured to receive the cutting accessory 32 along the nose tube axis N and rotatably drive the cutting accessory 32.

Typically, the axial connector 110, 150 and the drive connector 112 are spaced from each other along the nose tube axis N. For example, the axial connector 110, 150 is disposed at the distal end 106 of the nose tube 100 and the drive connector 112 is spaced from the axial connector 110, 150 along the nose tube axis N between the distal end 106 and the proximal end 108 of the nose tube 100. Alternatively, the drive connector 112 and the axial connector 110, 150 can be adjacent each other along the tool axis T. The axial connector 110, 150 and the distal connector releasably engage the cutting accessory 32 to the end effector 12.

The axial connector 110, 150 is supported by the nose tube 100 and releasably locks the cutting accessory 32 to the nose tube 100 along the nose tube axis N. The axial connector 110, 150 is releasably engaged with the shroud 40 of the cutting accessory 32. The axial connector 110, 150 defines a bore 57 extending along the nose tube axis N and receiving the cutting accessory 32. The cutting accessory 32 extends from the terminal end 106 of the nose tube 100 through the axial connector 110, 150 to the drive connector 112. When the cutting accessory 32 is assembled to the nose tube 100, the shroud 40 of the cutting accessory 32 extends along the nose tube axis N between a first end 47 proximate the cutting tip 50, e.g., the bur shown in the Figures, and a second end 49 distal to the cutting tip 50. The shaft 42 extends from the distal end 49 of the shroud 40 to the drive connector 112.

Figure 21:
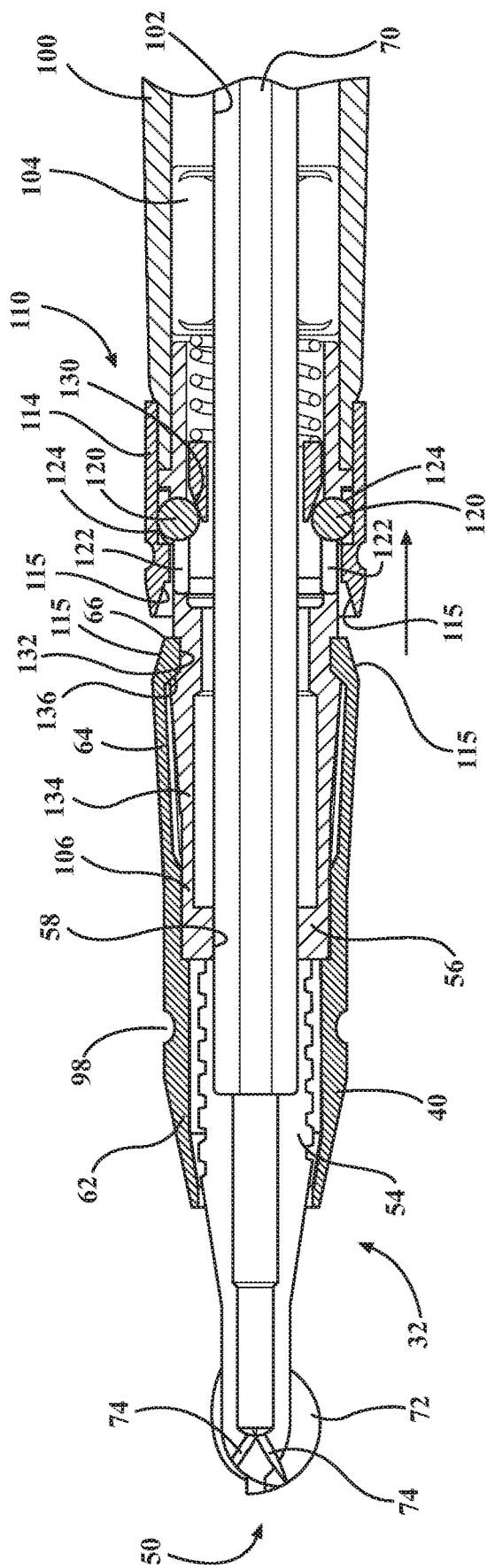
FIG. 21 is the cross-sectional view of FIG. 20 with a barrel of an axial connector in a release position.
Figure 22:
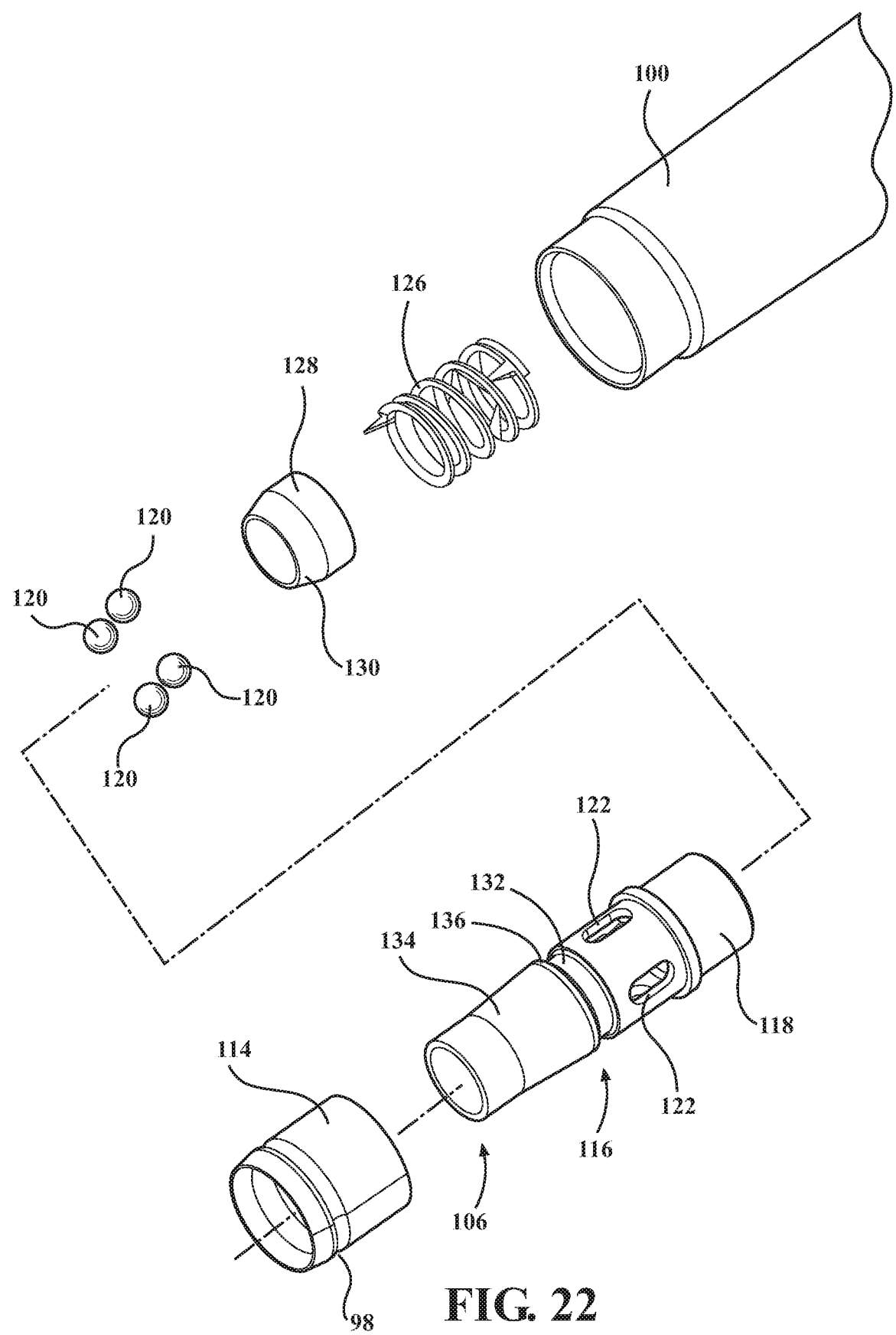
FIG. 22 is an exploded view of the axial connector.
Figure 23:
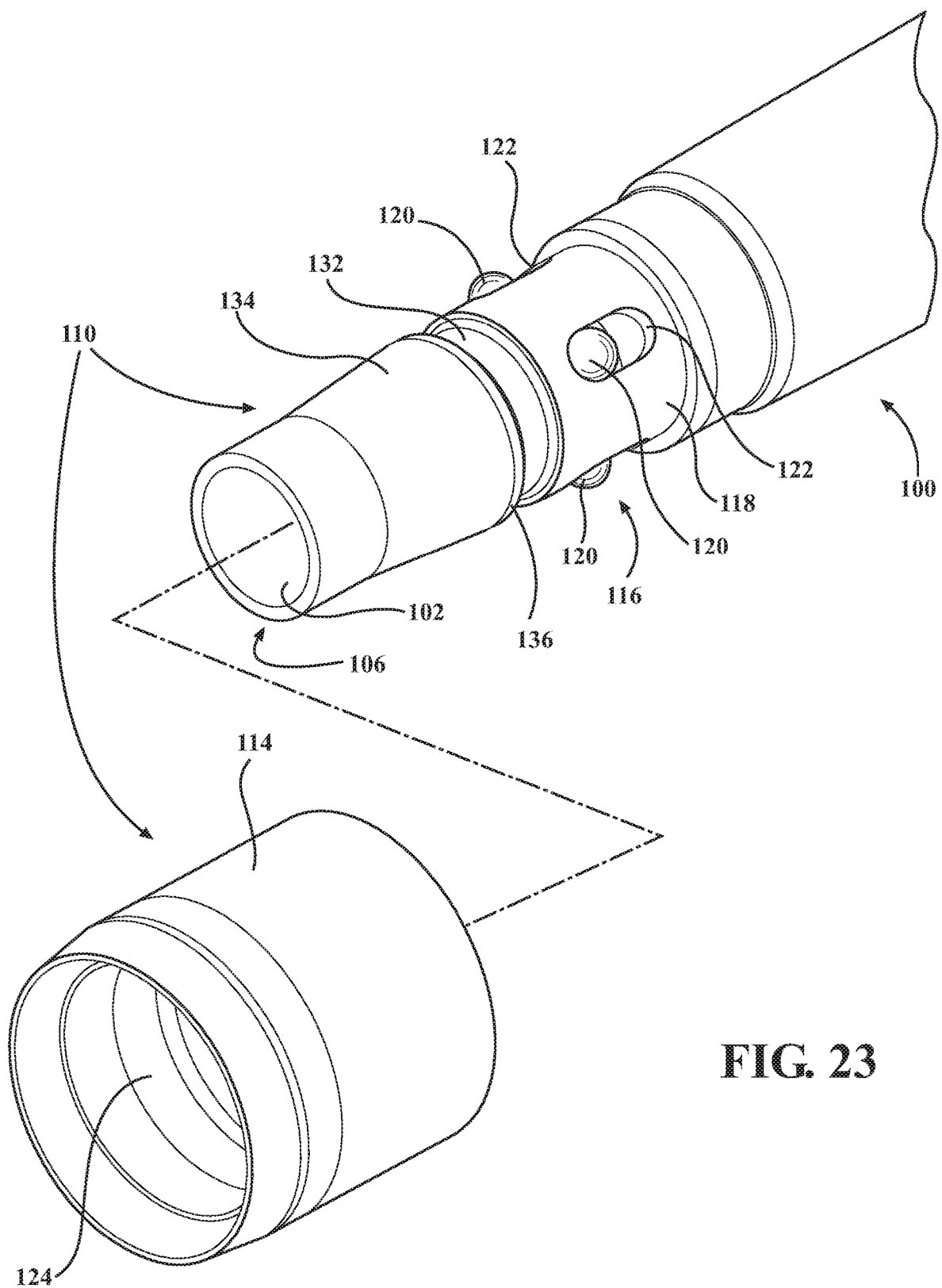
FIG. 23 is a partially exploded view of the axial connector with the barrel exploded from the nose tube.

With reference to the axial connector 110 shown in FIGS. 19-21, the axial connector 110 is typically coupled to the distal end 106 of the nose tube 100 and is moveable relative to the nose tube 100 between an extended position, i.e., a locked position, as shown in FIGS. 19 and 20, to retain the cutting accessory 32 and a retracted position, i.e., an unlocked position, as shown in FIG. 21 to release the cutting accessory 32. Specifically, the axial connector 110, 150 is moveable along the axis between the locked position and the unlocked position.

The axial connector 110, for example, includes a barrel 114, i.e., a ring 114, slidably retained on the nose tube 100. In other words, the barrel 114 is retained on the nose tube 100 and is slideable relative to the nose tube 100 between the extended position and the retracted position. Typically, the barrel 114 is rotatable about the tool axis T. The barrel 114 is typically cylindrical and receives the nose tube 100.

The barrel 114 extends radially about the shroud 40 to pinch the shroud against the nose tube 100 when the cutting accessory 32 is engaged with the nose tube 100 and the axial connector 110 is in the locked position. In other words, in the extended position, the barrel 114 is engaged with the cutting accessory 32, e.g., the shroud 40 of the cutting accessory 32, to engage the cutting accessory 32 to the nose tube 100. In the retracted position, the barrel 114 is disengaged with the cutting accessory 32 to release the cutting accessory 32 from the nose tube 100.

With reference to FIGS. 18-23, the nose tube 100 includes a guide portion 116 that supports the axial connector 110. For example, the nose tube 100 includes a guide portion 118 that presents the guide portion 116. The barrel 114 and the guide portion 116 define engaging features to operably couple the barrel 114 to the guide portion 116 such that the barrel 114 is moveable along the guide portion 116 between the extended position and the retracted position.

For example, at least one engaging member 120 is engaged with the barrel 114 and the guide portion 116 to couple the barrel 114 and the guide portion 116, as shown in FIGS. 19-23. The guide portion 116 of the nose tube 100 defines at least one channel 122 and the engaging member 120 is engaged with and moveable along the channel 122 between the extended position and retracted position. The channel 122 extends longitudinally along the nose tube axis N and typically extends through guide portion 116. The nose tube 100 shown in the Figures includes four engaging members 120 engaged with four channels 122, respectively. However, the axial connector 110 can include any number of engaging members 120 and corresponding channels 122.

The engaging member 120 is, for example, a spherical ball engaged with the barrel 114 and with the channel of the guide portion 116 to couple the barrel 114 to the guide portion 118. The barrel 114 defines a recess 124, typically semi-spherical in shape, that receives the ball. The ball is rotatable in the recess 124 and is fixed to the barrel 114 along the tool axis T. The ball is engaged with the channel 122 of the guide portion 116 to guide movement of the barrel 114 along the channel, i.e., along the nose tube axis N. In the alternative to the ball, the engaging member 120 can be any type of feature to couple the barrel 114 to the guide portion such as, for example, pins, flanges, etc.

With reference to FIGS. 19-22, the axial connector 110 includes a biasing device 126, e.g. a spring 126, coupled to the barrel 114 and the biasing device 126 urges the barrel 114 toward the extended position. The barrel 114 is movable to the retracted position by applying force against the barrel 114 toward the retracted position sufficient to overcome the force exerted by the biasing device 126, i.e., to compress the biasing device 126. As shown in the Figures, for example, the biasing device 126 is disposed in the nose tube bore 102. The biasing device 126 abuts bearing 104 in the nose tube bore 102, as shown in FIGS. 19-21, to retain the biasing device 126 in position along the nose tube axis N. The biasing device 126 shown in the Figures is a coil spring. Alternatively, the biasing device 126 is any type of biasing device.

With continued reference to FIGS. 19-22, a plunger 128 is disposed between the biasing device 126 and the barrel 114 for coupling the biasing device 126 and the barrel 114. Specifically, the plunger 128 is disposed in the nose tube bore 102 and is configured to slide relative to the nose tube 100 in the nose tube bore 102. The engaging members 120, e.g., balls, are disposed between the plunger 128 and the barrel 114 and the engagement members 120 contact the plunger 128. The plunger 128 defines a tapering surface 130 receiving the engaging members 120. The biasing device 126 abuts the plunger 128 between the bearing 56 and the plunger 128. In the alternative to the plunger 128, the barrel 114 and the biasing device 126 can be configured to be in direct contact.

With continued reference to FIGS. 19-22, the nose tube 100 defines a groove 132, i.e., a recess 132, near the distal end 106 of the nose tube 100 that extends circumferentially about the nose tube 100. With reference to FIGS. 19-21, the groove 132 is defined in part by a ramped surface 134 that tapers away from the nose tube axis N. A sloped surface 136 extends from the ramped surface 134 toward the distal end of the nose tube 100 and tapers toward the nose tube axis N. When in the extended position, the barrel 114 is typically adjacent the groove 132, i.e., aligned at least in part with the groove 132 along the nose tube axis N and disposed radially about at least a portion of the groove 132.

With the use of the axial connector 110, the cutting accessory 32 can be engaged with the end effector 12 without the use of a tool 38, i.e., merely with the use of a hand of a human operator. The assembly of the cutting tool 38 to the end effector 12 can be a one-handed operation, i.e., accomplished with the use of a single hand of the human operator. The cutting tool 38 is assembled to the end effector 12 by inserting the cutting tool 38 into the nose tube bore 102 and exerting pressure on the cutting tool 38 along the nose tube bore 102 toward the nose tube 100 to engage the cutting tool 38 with the axial connector 110.

Specifically, to assemble the cutting accessory 32 to the end effector 12, the shaft 42 of the tool 38 is inserted into the nose tube bore 102. As the shaft 42 is moved along the nose tube bore 102, the shaft 42 is received by the bearing(s) 104 in the nose tube bore 102. As set forth above, the fingers 64 of the shroud 40 are flexible relative to the body portion 62 of the shroud 40. Typically, the fingers 64 slide along the sloped surface 136 and deform outwardly relative to the tool axis T along the sloped surface 136 as the shroud 40 approaches the barrel 114.

As the shaft is moved along the nose tube bore 102, the tips 66 of the fingers 64 abut the barrel 114 and push the barrel 114 toward the retracted position. Specifically, the fingers 64 and the barrel 114 include opposing surfaces 115 that oppose each other along the nose tube axis N as the cutting accessory 32 is engaged with the nose tube 100. The opposing surfaces 115 are typically ramped. For example, the opposing surface 115 of each finger 64 is a ramped surface tapering radially inwardly in a direction from the first end 47 of the shroud 40 toward the second end 49 of the shroud 40 for contacting the nose tube 100 and flexing the fingers 64 during engagement of the cutting accessory 32 with the nose tube 100. The opposing surface 115 of each finger 64 terminates at the second end 49 of the shroud 40.

When the tips 66 of the fingers 64 reach the groove 132, the tips 66 move inwardly toward the tool axis T into the groove 132 in the nose tube 100 and the barrel 114 returns to the extended position to lock the cutting accessory 32 to the nose tube 100. In other words, the axial connector 110 engages the fingers 64 when the cutting accessory 32 is engaged with the nose tube 100 and the axial connector 110 is in the extended position.

The fingers 64 each define a protrusion 65, as shown in FIGS. 15 and 16, for example, configured to engage the groove 132. The fingers 64 are typically configured to resiliently deform outwardly along the sloped surface 136 such that the fingers 64 spring toward the pre-deformed shape into the groove 132. In addition or in the alternative, the barrel 114 deforms the fingers 64 into the groove 132 as the tips 66 contact and slide along the barrel 114.

When the cutting accessory 32 is engaged with the end effector 12, the bearing 56 of the cutting accessory 32 abuts the distal end 106 of the nose tube 100. The axial connector 110 is configured to engage the cutting accessory 32 when the bearing 56 of the cutting accessory 32 abuts the distal end 106 of the nose tube 100. The snapping of the tips 66 of the fingers 64 into the groove 132 provides a tactile confirmation that the cutting accessory 32 is properly placed in a position for the axial connector 110 to engage the cutting accessory 32 to the nose tube 100, i.e., confirms that the bearing 56 abuts the distal end 106 of the nose tube 100. In other words, the operator confirms that the cutting accessory 32 is properly located relative to the end effector 12 for engagement by the axial connector 110 when the operator feels, sees, and/or hears the tips 66 of the fingers 64 enter the groove 132. The fingers 64, the sloped surface 136 of the nose tube 100, and the barrel 114 are configured to draw the bearing 56 against the distal end 106 of the nose tube 100 when the cutting accessory 102 is engaged with the end effector 12, i.e., when tips 66 of the fingers 64 are engaged with between the sloped surface 136 of the nose tube 100 and the barrel 114.

When the tips 66 of the fingers 64 are in the groove 132, the biasing device 126 biases the barrel 114 to the extended position absent extraneous force applied to the barrel 114. When the tips 66 of the fingers 64 are in the groove 132 and the barrel 114 is in the extended position, the barrel 114 pinches the fingers 64 against the ramped surface 134 of the nose tube 100 to lock the shroud 40 to the nose tube 100.

To release the cutting tool 38 from the end effector 12, the barrel 114 is moved toward the retracted position to release the tips 66 of the fingers 64 from the groove 132. Typically, the barrel 114 is moved toward the retracted position by a human operator who exerts force on the barrel 114 toward the retracted position. The barrel 114 and the nose tube 100 define opposing surfaces 138 configured to abut each other when the barrel 114 is moved to the retracted position.

With the barrel 114 in the retracted position, the cutting tool 38 can be moved along the nose tube axis N away from the nose tube 100. Typically, the fingers 64 are configured to remain in the groove 132 when the barrel 114 is in the retracted position and, as the cutting tool 38 is moved away from the nose tube 100, the fingers 64 resiliently deform away from the tool axis T as the tips 66 of the fingers 64 slide along the ramped surface 134.

As set forth above, the guard 68 is configured to engage and disengage the cutting accessory 32 with the end effector 12. Specifically, the guard 68 is configured to actuate the barrel 114. In other words, the guard 68 is configured to move the barrel 114 to the retracted position to engage and disengage the cutting accessory 32 with the nose tube 100.

Figure 37:
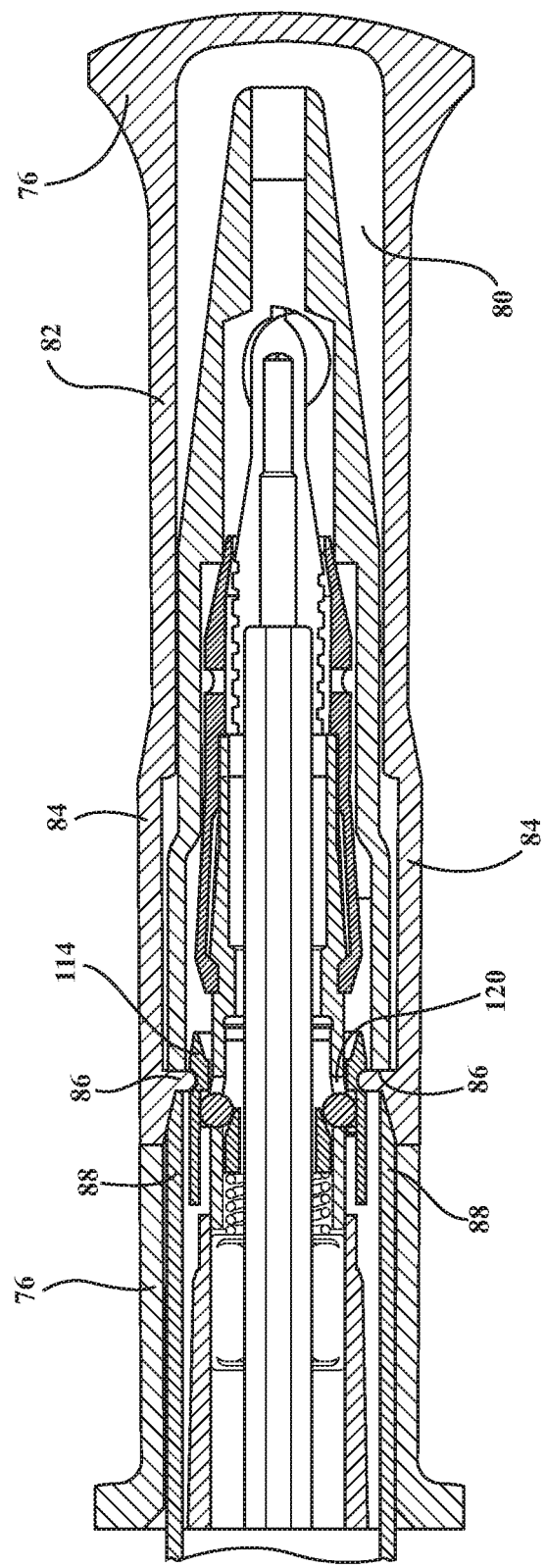
FIG. 37 is a cross-sectional view of the guard and the cutting accessory along line 29 of FIG. 35.
Figure 38:
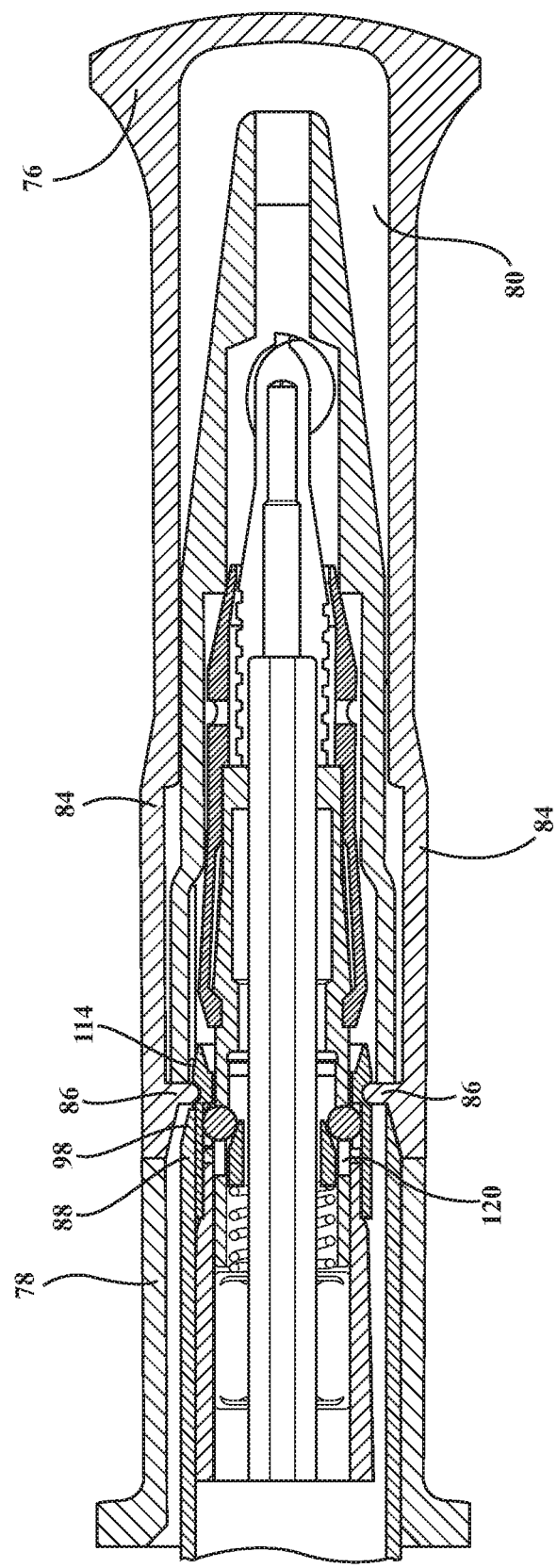
FIG. 38 is a cross-sectional view of the guard engaging the axial connector to release the cutting accessory from the nose tube.

With reference to FIGS. 32-34B, the guard 68 includes an outer member 76 and an inner member 78 slideably engaged with the outer member 76. Specifically, the outer member 76 defines a bore 80 and slideably receives the inner member 78 in the bore 80. The inner member 78 is slideable in the bore 80 between an extended position, as shown in FIG. 37, and a compressed position, as shown in FIG. 38.

Figure 34A:
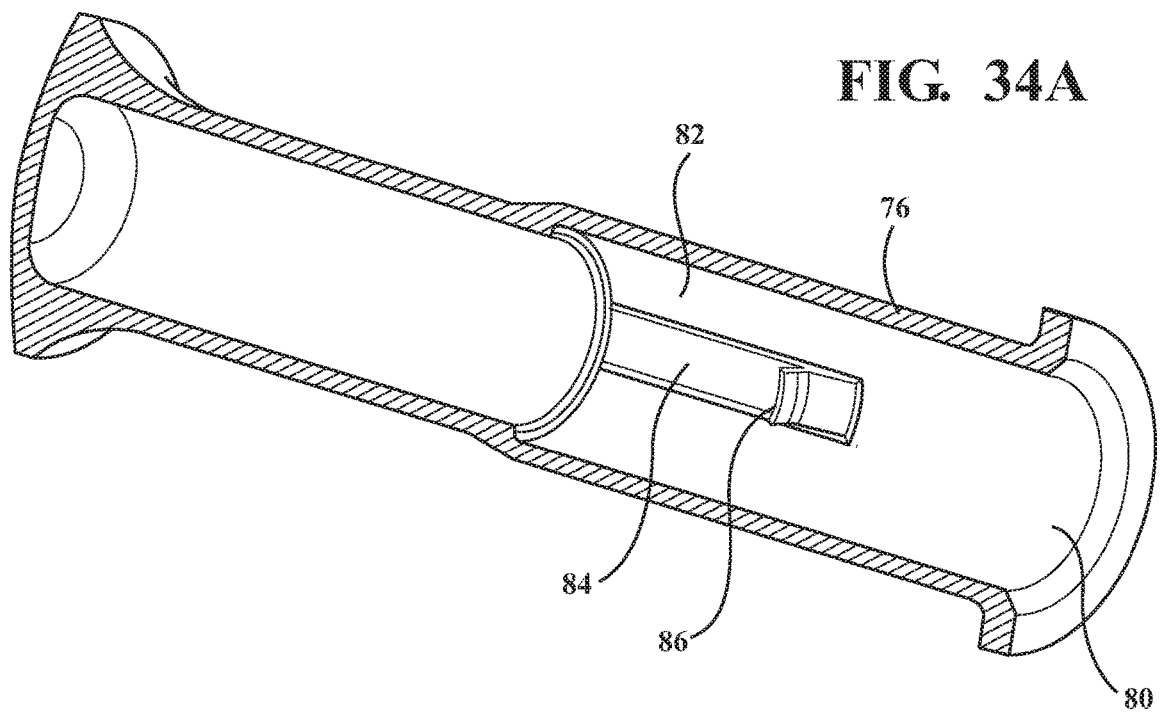
FIG. 34A is a cross-sectional view of an outer member of the guard.

With reference to FIG. 34A, the outer member 76 includes a body 82 and flexible tangs 84 flexibly connected to the body 82. The flexible tangs 84 support barbs 86 that extend into the bore 80. The inner member 78 defines slots 88 that receive the barbs 86.

Figure 34B:
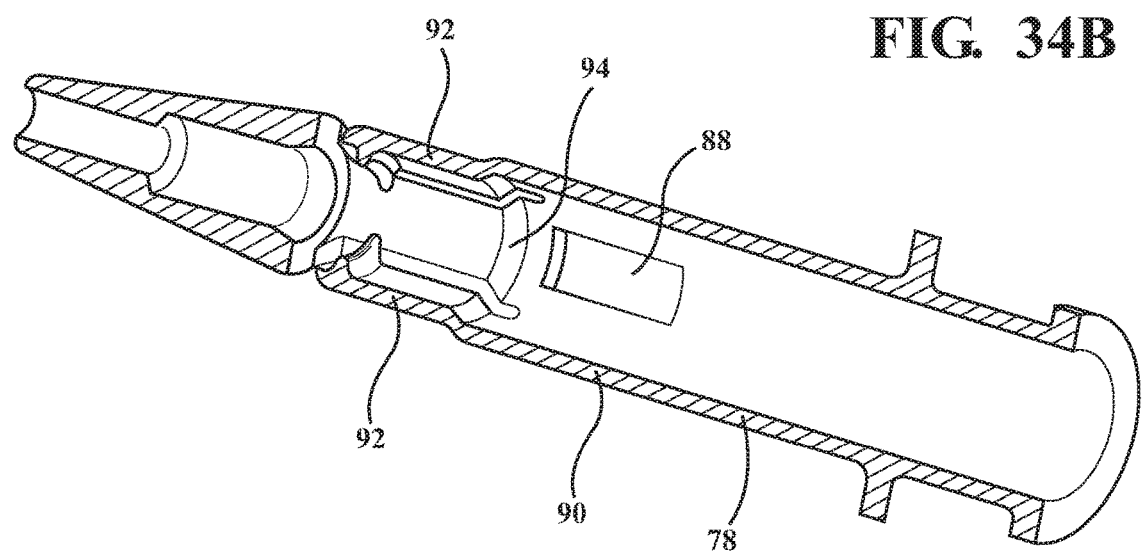
FIG. 34B is a cross-sectional view of an inner member of the guard.

With reference to FIG. 34B, the inner member 78 includes a body 90 and flexible tangs 92 flexibly connected to the body 90. The flexible tangs 92 support barbs 90. The inner member 78 defines an interior ledge 94 that is, for example, frusto-conical in shape. The inner member 78 can include a finger grip 97.

Figure 35:
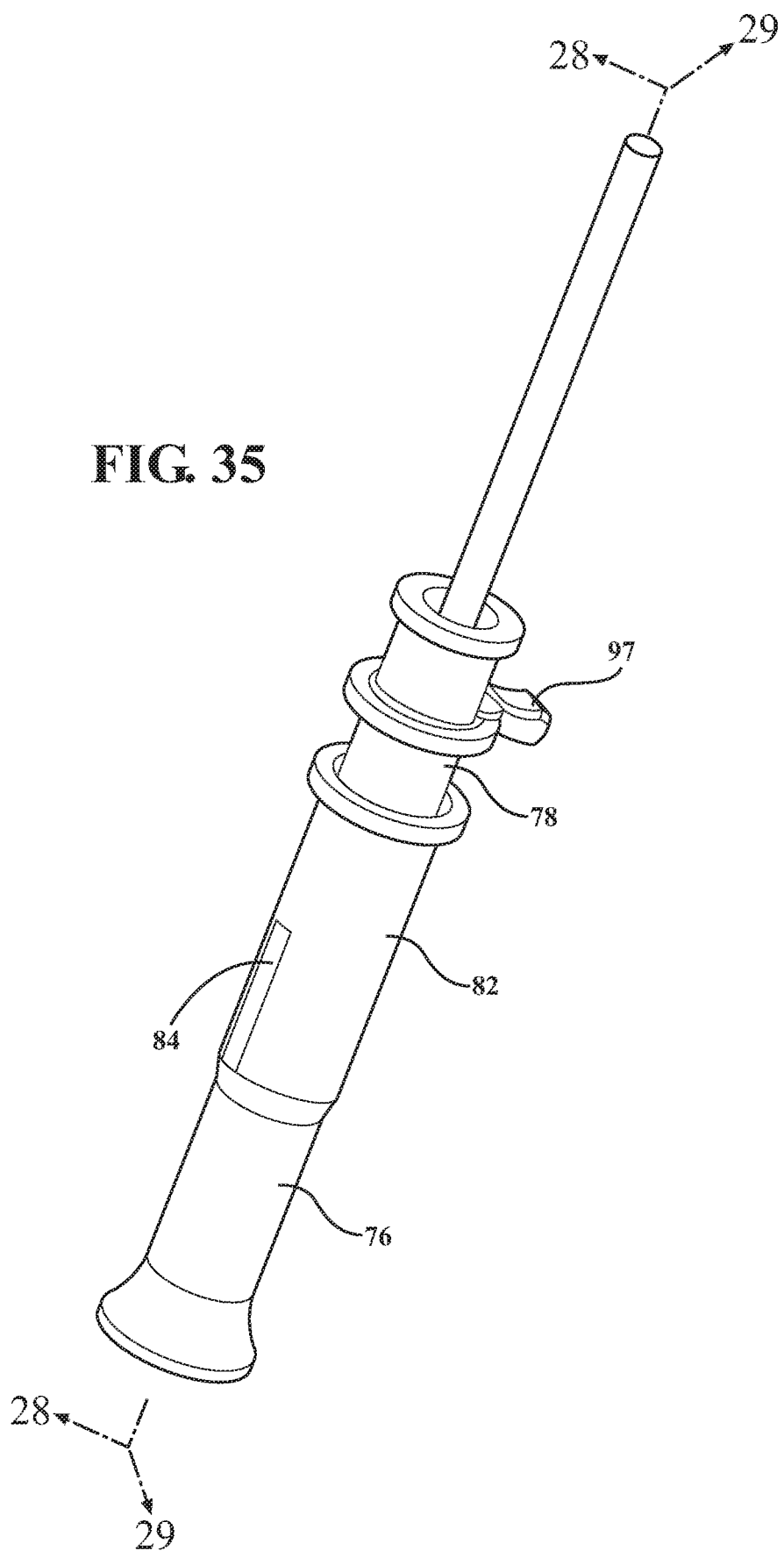
FIG. 35 is a perspective view of the cutting accessory and the guard covering a portion of the cutting accessory.
Figure 36:
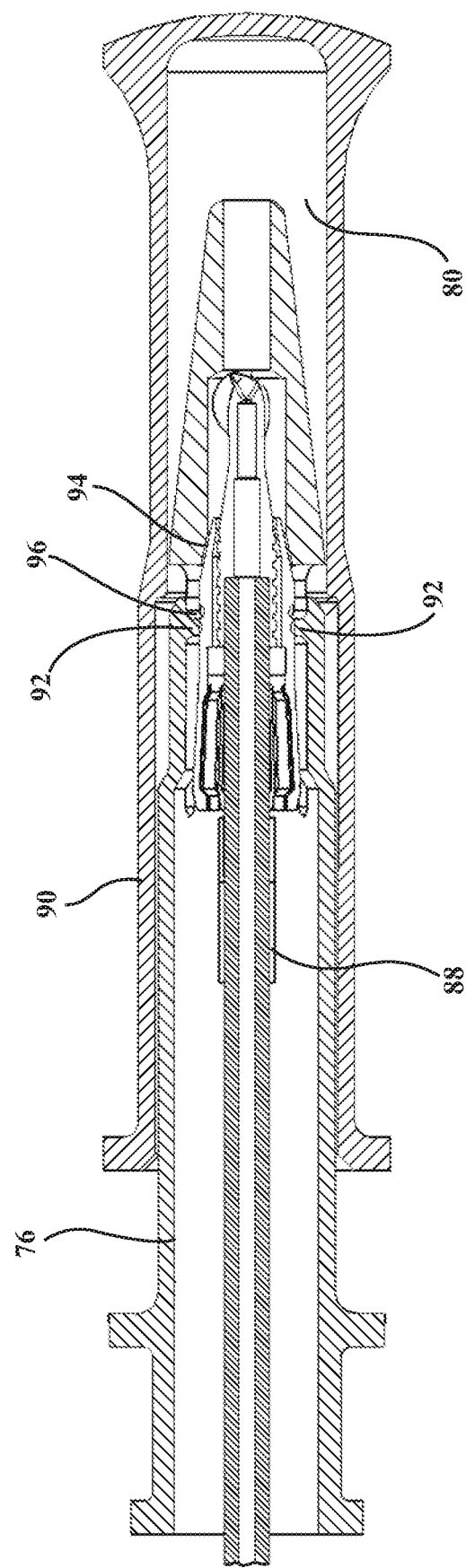
FIG. 36 is a cross-sectional view of the guard and the cutting accessory along line 28 in FIG. 35.

With reference to FIGS. 35 and 36, the guard 68 receives the cutting accessory 32. As set forth above, the guard 68 covers the cutting tip 50 of the cutting accessory 32 to aid in the handling of the cutting accessory 32.

When the cutting accessory 32 is disposed in the guard 68, the shroud 40 of the cutting accessory 32 abuts the ledge 94. The shroud 40 defines a groove 96 that receives the tangs 92 of the inner member 78.

When the guard 68 receives the cutting accessory 32 such that the shroud 40 abuts the ledge 94, the operator can use the inner member 78 to engage the cutting accessory 32 with the axial connector 110. Specifically, with the shaft 42 of the cutting accessory 32 in the nose tube bore 102, the user can exert force on the inner member 78 toward the nose tube 100 along the nose tube axis T such that the ledge 94 of the guard 68 forces the shroud 40 into engagement with the axial connector 110. Once the shroud 40 is engaged with the axial connector 100, the guard 68 can be removed from the cutting accessory 32 by exerting force on the guard 68 away from the nose tube 100 along the nose tube axis T.

To disengage the cutting accessory 32 from the axial connector 110, e.g., after a surgical procedure, the guard 68 is placed on the cutting accessory 32 with the ledge 94 abutting the shroud 40. In such a configuration, the tangs 84 of the outer member 76 engage a groove 98 on the barrel 114. The outer member 76 is then moved relative to the inner member 78 to the compressed position, as shown in FIG. 38, to move the barrel 114 to the retracted position.

Specifically, the operator grasps the inner member 78 with one hand and grasps the outer member 76 with the other hand. The operator then moves the outer member 76 relative to the inner member 78 along the nose tube axis N. This movement, as shown in FIG. 38, forces the tangs 84 of the outer member 76 against the groove 98 of the barrel 114 to force the barrel 114 to the retracted position to release the cutting accessory 32 from the nose tube 100.

As set forth above, when the guard 68 is disposed on the cutting accessory 32, the tangs 92 of the inner member 78 frictionally engage the shroud 40. With the outer member 76 moved to the compressed position, as shown in FIG. 38, the outer member 76 and inner member 78 are moved along the nose tube axis N away from the nose tube 100 to remove the cutting accessory 32 from the nose tube 100. During this movement, the frictional engagement between the tangs 92 and the shroud 40 retains the cutting accessory 32 attached to the guard 68 as the guard 68 is moved away from the nose tube 100.

As set forth above, the axial connector 150 shown in FIGS. 24-31 receives the cutting accessory 32 including the shroud 140. The axial connector 150 is supported on a guide portion 152 of the nose tube 100. The axial connector 150 includes fingers 154 supported by the guide portion 152 and a barrel 156 that is rotatable about the nose tube axis T to lock and unlock the fingers 154 radially relative to the guide portion 152, as set forth further below.

Figure 27:
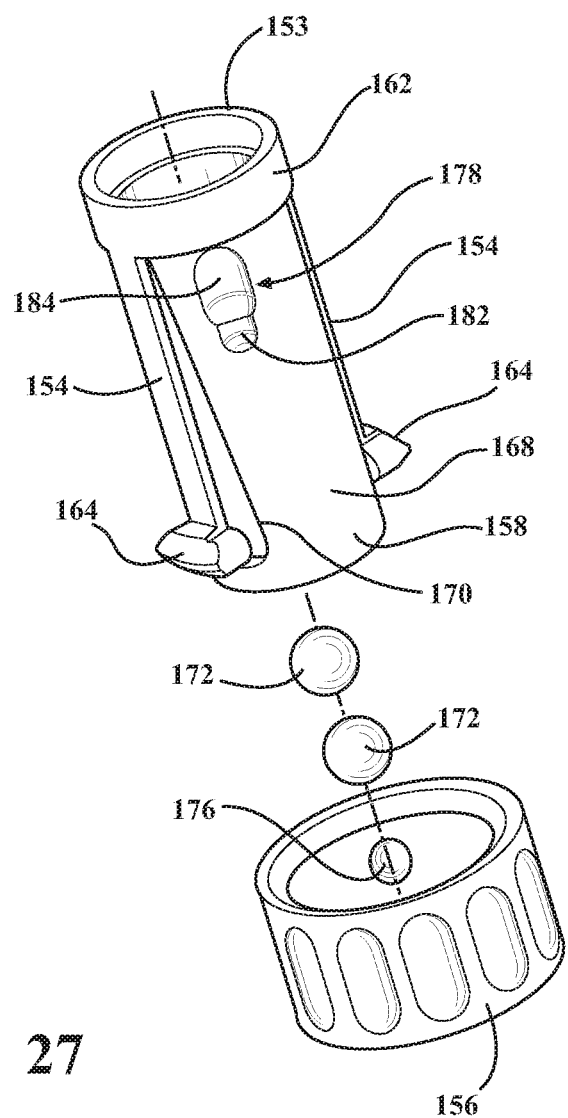
FIG. 27 is a partially exploded view of the axial connector of FIG. 24.
Figure 26:
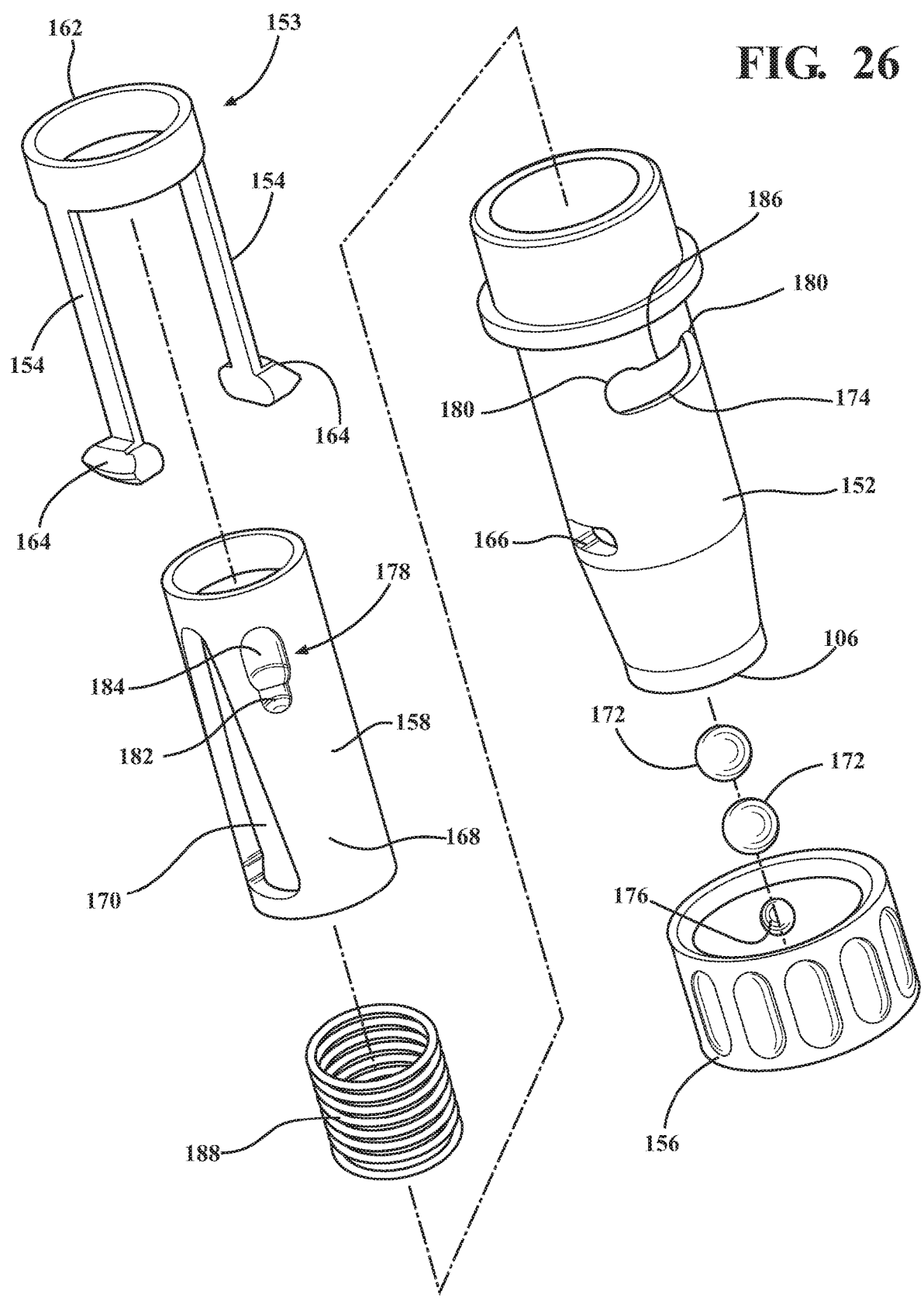
FIG. 26 is an exploded view of the axial connector and a portion of the nose tube of FIG. 24.

Specifically, with reference to FIGS. 26 and 27, the axial connector 150 includes a locking member 153 that includes a ring 162 and the fingers 154 extending from the ring 162. The fingers 154 each include a protrusion 164. While FIGS. 26 and 27 show the locking member 153 including two fingers 154, the locking member 153 can include any suitable number of fingers 154 without departing from the nature of the present invention.

Figure 28:
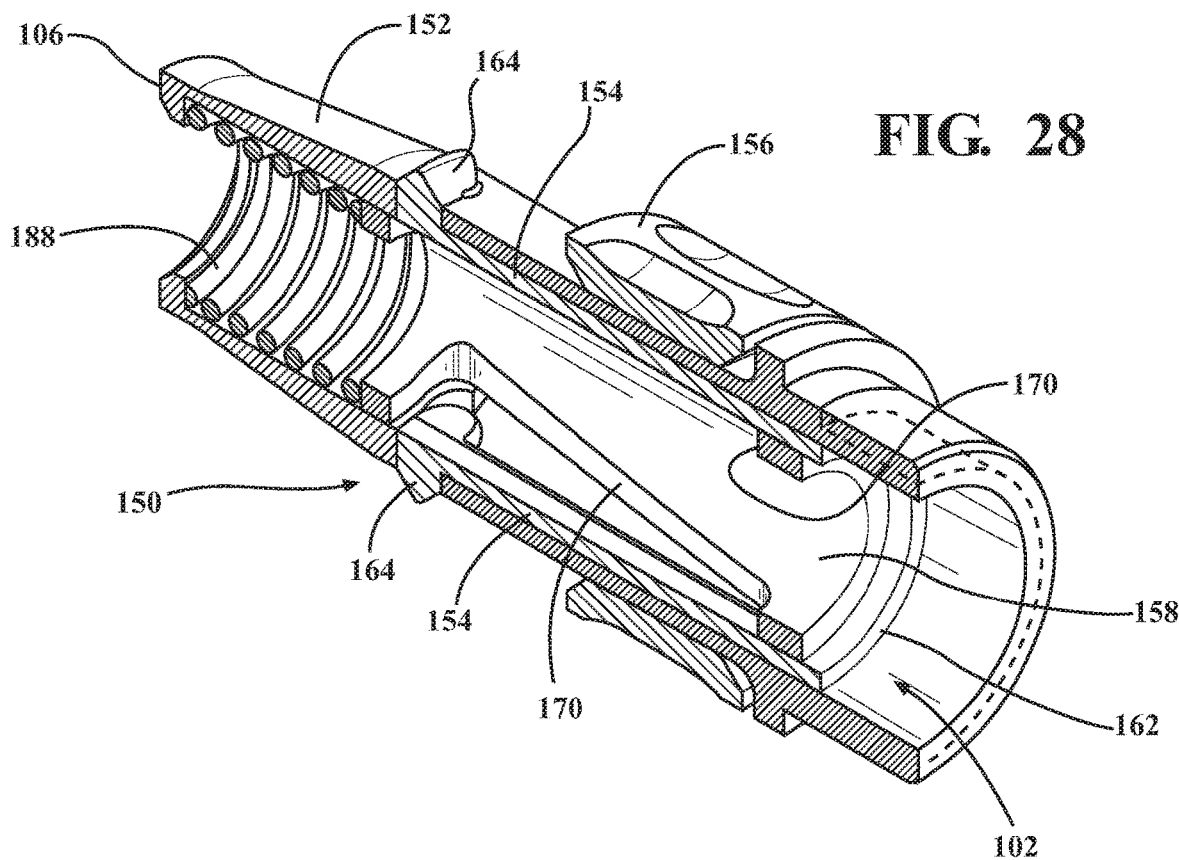
FIG. 28 is a cross-sectional view of the axial connector and a portion of the nose tube of FIG. 24.
Figure 29:
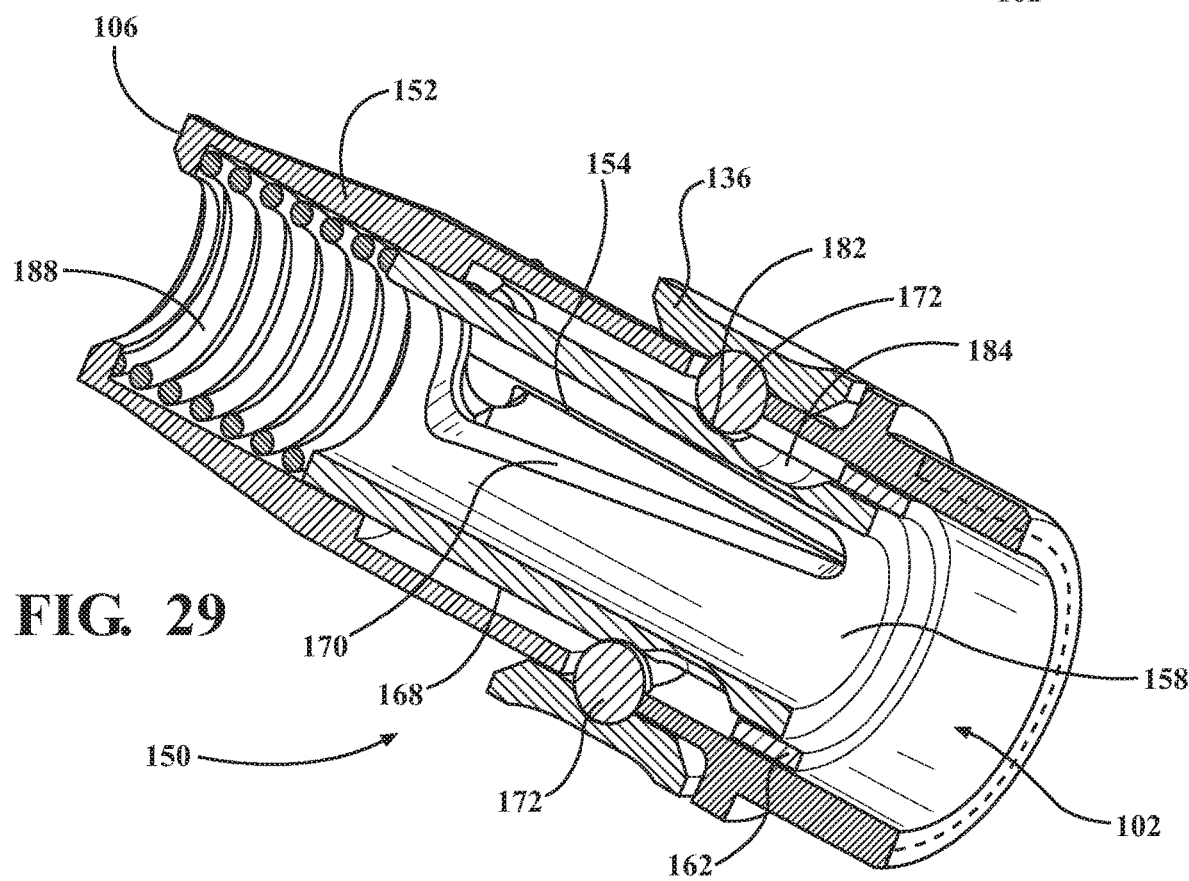
FIG. 29 is another cross-sectional view of the axial connector and a portion of the nose tube of FIG. 24.

With reference to FIGS. 26, 28, and 29, the guide portion 152 receives the lock collar 158. The guide portion 152 defines a pair of slots 166, as shown in FIGS. 26 and 27, and the protrusions 164 of each of the fingers 154 are positioned to extend through the slots 166, respectively, as shown in FIGS. 27 and 28. The fingers 154 bias the protrusions 164 to extend through the slots 166.

With reference to FIGS. 26-29, the lock collar 158 is disposed in the guide portion 152 and is positioned radially inwardly of the fingers 154. The lock collar 158 includes a wall 168, typically cylindrical, that defines cutouts 170 spaced circumferentially about the wall 168 for receiving the protrusions 164 of the fingers 154, as set forth further below.

The barrel 156 is supported on the guide portion 152 and engages the lock collar 158 through the guide portion 152. Specifically, as best shown in FIG. 29, balls 172 extend through slots 174 in the guide portion 152 and engage the barrel 156 and the lock collar 158. As best shown in FIGS. 26, 27, and 29, the barrel 156 defines dimples 176 that receive the balls 172. With reference to FIGS. 26 and 27 the lock collar 158 defines grooves 178 that receive the balls 172. While FIGS. 26 and 27 show the two balls 172, the lock collar 158 can include any suitable number of balls 172 without departing from the nature of the present invention.

The barrel 156 is rotatable about the nose tube axis N between an unlocked position, as shown in FIGS. 28 and 29, and a locked position (not shown). The lock collar 158 moves with the barrel 156 between the locked position and the unlocked position. In the unlocked position, the barrel 156 is positioned to align the cutouts 170 of the lock collar 158 with the fingers 154 to allow the fingers 154 to resiliently move radially inwardly in response to forces on the protrusions 164. In the locked position, the barrel 156 is positioned to align the wall 168 of the lock collar 158 with the fingers 154. In such a position, the wall 168 prevents the fingers 154 from moving radially inwardly in response to forces on the protrusions 164, i.e., locking the fingers 154 in place.

With reference to FIGS. 30 and 31, the cutting accessory 32 is attached to the nose tube 100 by inserting the shaft 38 of the cutting accessory 32 into the nose tube bore 102 and along the nose tube axis N. With the barrel 156 in the unlocked position, i.e., with the cutouts 170 of the lock collar 158 aligned with the fingers 154, the shroud 140 of the cutting accessory 32 depresses the protrusions 164 of the fingers 154 radially inwardly when the shroud 110 reaches the protrusions. Since the shroud 140 depresses the fingers 154 radially inwardly, the cutting accessory 32 can be seated against the nose tube 100, as shown in FIGS. 30 and 31. Specifically, the bearing 56 of the cutting accessory 32 abuts the distal end 106 of the nose tube 100 when the cutting accessory 32 is seated against the nose tube 100.

When the cutting accessory 32 is seated against the nose tube 100, the fingers 154 are resiliently biased through the slot 166 of the guide portion 152 and into engagement with the groove 178 of the shroud 140, for example, as shown in FIGS. 30 and 31. When the cutting accessory 32 is seated against the nose tube 100, the barrel 156 is rotated to the locked position, i.e., to align the wall 168 of the lock collar 158 with the fingers 154 to prevent the fingers 154 from being depressed radially inwardly. In such a position, the axial connector 150 axially locks the cutting accessory 32 to the nose tube.

When the cutting accessory 32 is to be disassembled from the nose tube 100, the barrel 156 is rotated to the unlocked position, i.e., to align the cutouts 170 of the lock collar 158 with the fingers 154. In such a position, when the cutting accessory 32 is pulled from the nose tube 100, the shroud 140 of the cutting accessory 32 depresses the fingers 154 radially inwardly into the cutouts 170 to allow the cutting accessory 32 to be removed from the nose tube 100.

With reference to FIG. 26, the guide portion 152 and the lock collar 158 are configured to provide haptic feedback identifying the locked position and unlocked position of the barrel 156. Specifically, the slots 174 of the guide portion 152 define detents 180 and the groove 178 of the lock collar 158 has a shallow portion 182 and a deep portion 184. A flat 186 is positioned between the detents 180 of the slot 174. A spring 188 is disposed in the guide portion 152 between the guide portion 152 and the lock collar 158 and biases the balls 172 into the detents 180 and the shallow portions 182.

In particular, when the barrel 156 is in the unlocked position, the ball 172 is disposed one of the detents 180. As the barrel 156 is rotated toward the locked position, the flat 186 forces the lock collar 158 against the spring 188. When the ball 172 reaches the other detent 180, the spring forces the ball 172 to enter the other detent 180. The interaction of the balls 172 with the detents 180 provides a haptic feedback and also resiliently retains the barrel 156 in the selected unlocked position or locked position.

Figure 39:
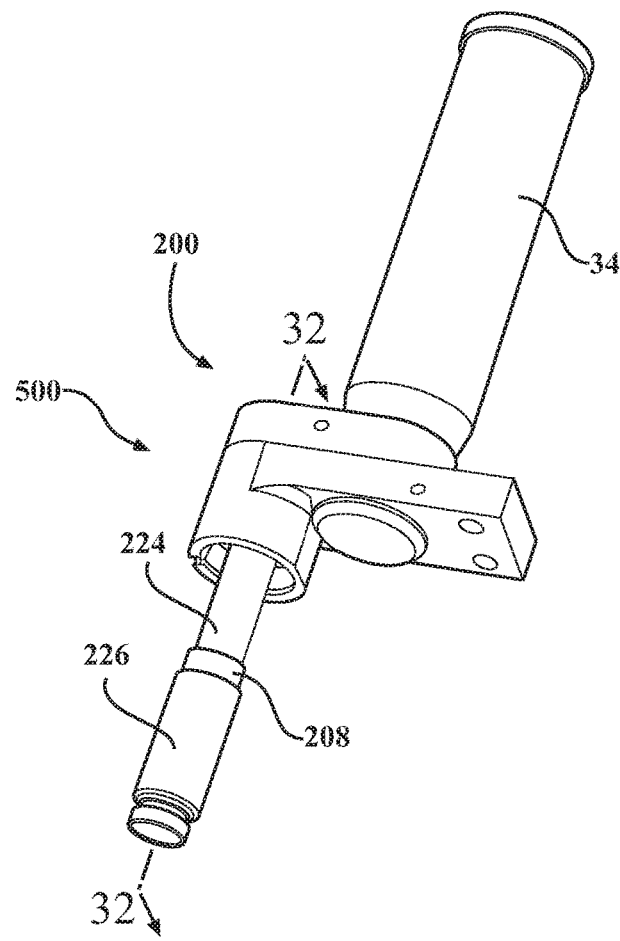
FIG. 39 is a perspective view of a drive system of the end effector.
Figure 40:
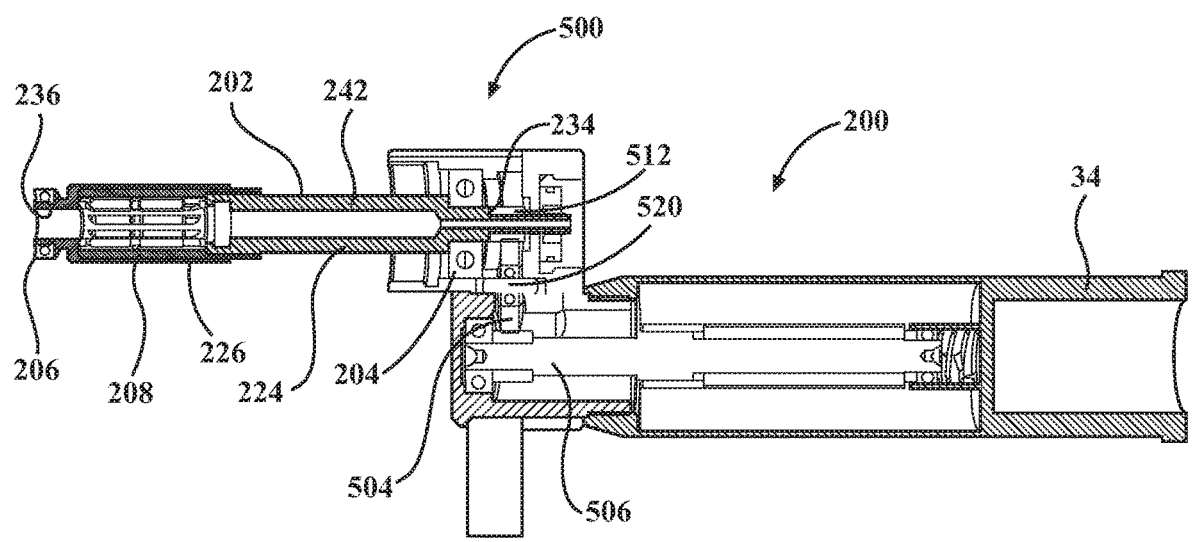
FIG. 40 is a cross-sectional view along line 32 of FIG. 39.

With reference to FIGS. 39 and 40, the cutting tool 38 includes a drive system 200 for driving the cutting accessory 32. The drive system 200 shown in the Figures is configured to impart rotational movement to the cutting accessory 32, e.g., to rotate the bur. Alternatively, the drive system 200 can be configured to impart any type of movement to the cutting accessory 32 such as, for example, oscillating translation for a reciprocating saw, pinching movement for opposing blades, translation for a needle/catheter, etc.

Figure 44:
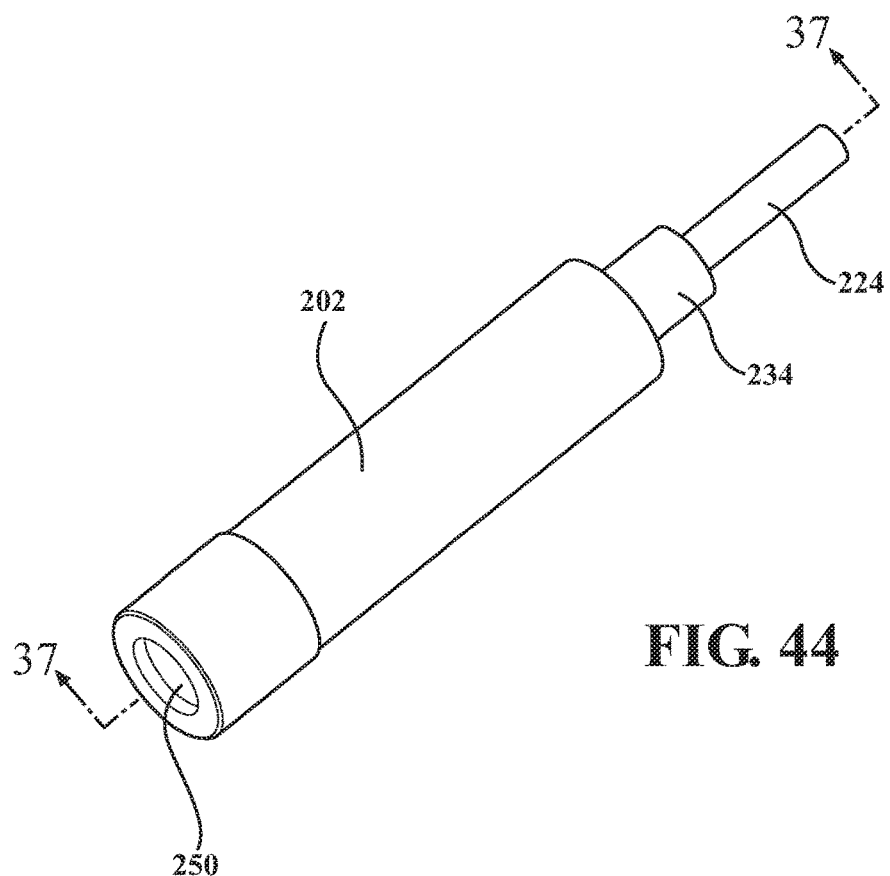
FIG. 44 is a perspective view of a drive member.
Figure 45:
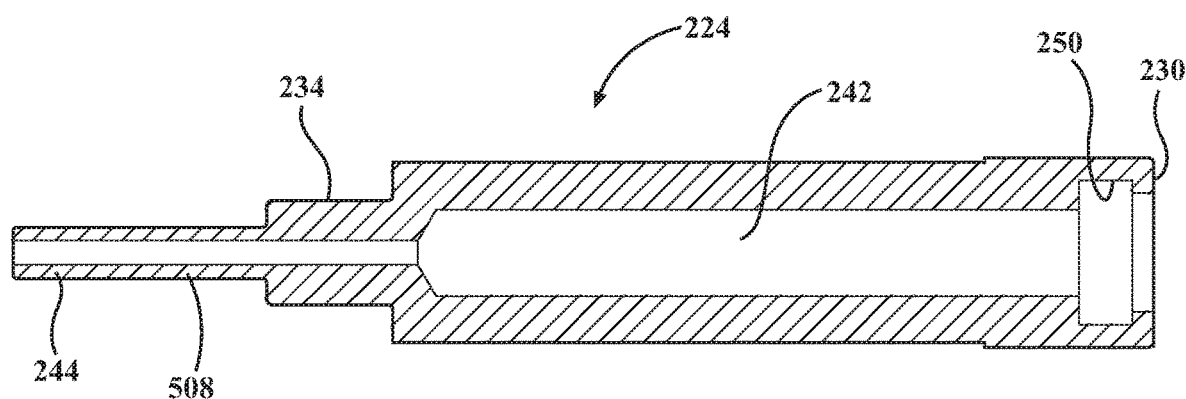
FIG. 45 is a cross-sectional view along line 37 of FIG. 44.
Figure 46:
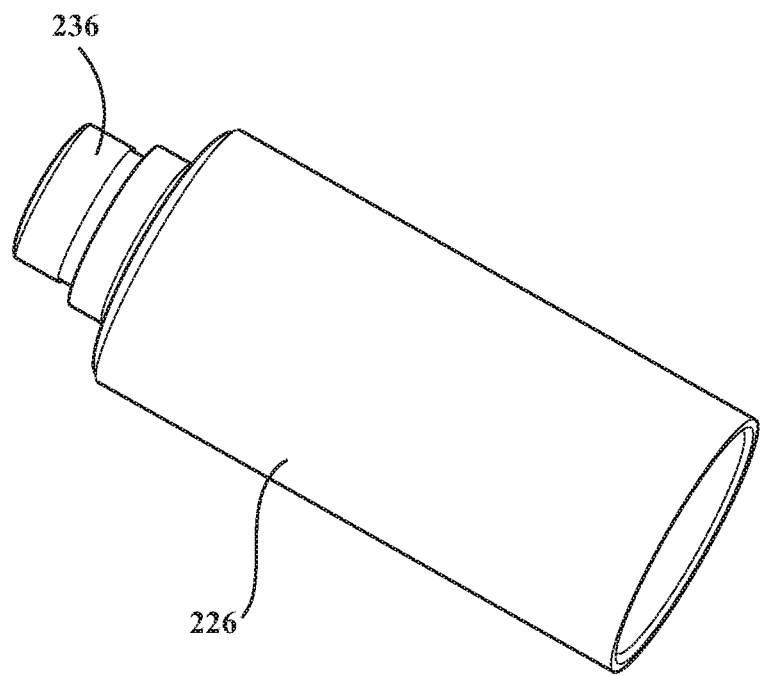
FIG. 46 is a perspective view of a socket.

The drive system 200 includes a drive member 202, e.g., a rotational drive member 202, supported by the nose tube 100, an actuator 34 coupled to the drive member 202, and the drive connector 112 coupled to the drive member 202 for rotationally engaging the cutting accessory 32. The drive member 202 shown in the Figures is rotatably supported in the nose tube 100. Specifically, a bearing 204 is disposed between the drive member 202 and the nose tube 100 and the bearing 204 rotatably supports the drive member 202 in the nose tube 100. With reference to FIGS. 44 and 45, the drive member 202 defines a bearing surface 234 for receiving the bearing 204. As set forth further below, the actuator 34 is coupled to the drive member 202 to rotate the drive member 202. Specifically, the actuator 34 is coupled to the drive connector 112 to rotate the drive connector 112 relative to the nose tube 100.

The drive connector 112 is supported by the nose tube 100 and receives the cutting accessory 32 for rotatably driving the cutting accessory 32. The drive connector 112 defines a bore 207 extending along the nose tube axis N and receiving the cutting accessory 32.

Figure 43:
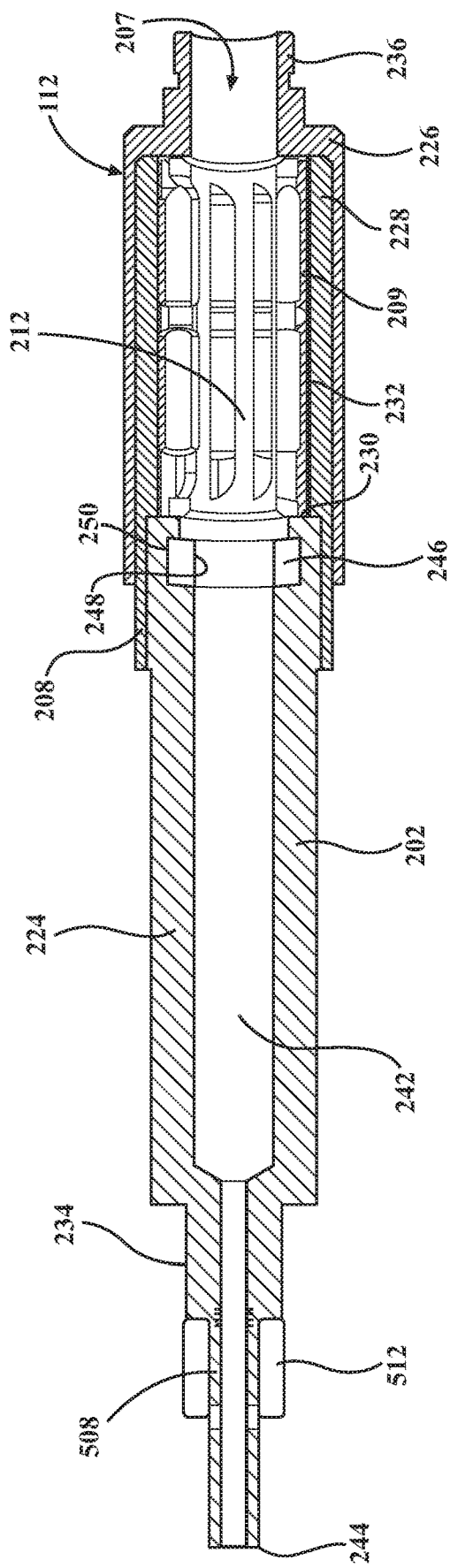
FIG. 43 is a cross-sectional view along line 35 in FIG. 41.

With reference to FIGS. 41-43, the drive connector 112 includes a wedge sleeve 208 and a clutch assembly 210 disposed in the wedge sleeve 208. The axial connector 110 is spaced from the clutch assembly 210. Specifically, the axial connector 110 is disposed between the clutch assembly 210 and the cutting tip 50 of the cutting accessory 32.

The clutch assembly 210 is configured to slideably receive the shaft 42 of the tool 38 along the nose tube axis N. The clutch assembly 210 is supported by and rotatable relative to the drive member 202 and receives the shaft 42 of the cutting accessory 32 along the nose tube axis N for selectively locking the shaft 42 to the drive member 202. Specifically, the shaft 42 is slideable into the clutch assembly 210 to engage the tool 38 with the clutch assembly 210 and is slideable out of the clutch assembly 210 to disengage the tool 38 from the clutch assembly 210.

The wedge sleeve 208 and the clutch assembly 210 are configured to frictionally lock the drive member 202 to the shaft 42 of the cutting accessory 32 to transmit rotation from the drive member 202 to the shaft 42. The clutch assembly 210 allows for use of a relatively short shaft 42 on the cutting accessory 32. Such use of a relatively short shaft 42 of the cutting accessory 32 increases stiffness of the cutting accessory 32, increases surgical access, and is more economical based on use of less material.

With reference to FIGS. 48-55, the clutch assembly 210 includes a cage 212 defining a bore and a plurality of slots 216 spaced circumferentially about the cage 212 in communication with the bore. Rollers 214 are disposed in each of the slots 216. The cage 212 defines a pair of spaced edges 218 defining each slot 216 and the roller 214 abuts both of the pair of edges 218. The rollers 214 extend through the slot into the bore. The rollers 214 are spaced from each other and receive the shaft 42 therebetween.

The rollers 214 are radially moveable relative to the cage 212. A spring 220 extends around the rollers 214 and the cage 212 to retain the rollers 214 in the slots 218 of the cage 212 and to urge the rollers 214 in contact with the edges 218. The rollers 214, for example, define a neck 222 for receiving the spring 220. The clutch assembly 210 shown in FIGS. 48-55 includes six slots 218 and six rollers 214; however, the clutch assembly 210 can include any number of slots 218 and corresponding rollers 214. The shaft 42 of the cutting accessory 32 contacts each of the rollers 214 when the shaft 42 is disposed the clutch assembly 210.

With reference to FIGS. 41-43, the drive member 202, for example, engages a socket 226 and the clutch assembly 210 is retained between the drive member 202 and the socket 226. The socket 226, for example, defines a lip 228 and the drive member 202 includes an end 230. The lip 228 and the end 230 define a cavity 232 therebetween and the clutch assembly 210 is disposed in the cavity 323, as shown in FIG. 43. A bearing 206 is disposed between the socket 226 and the nose tube 100 and the bearing 206 rotatably supports the socket 226 in the nose tube 100. With reference to FIGS. 44 and 45, socket 226 defines a bearing surface 236 for receiving the bearing 206.

Figure 47:
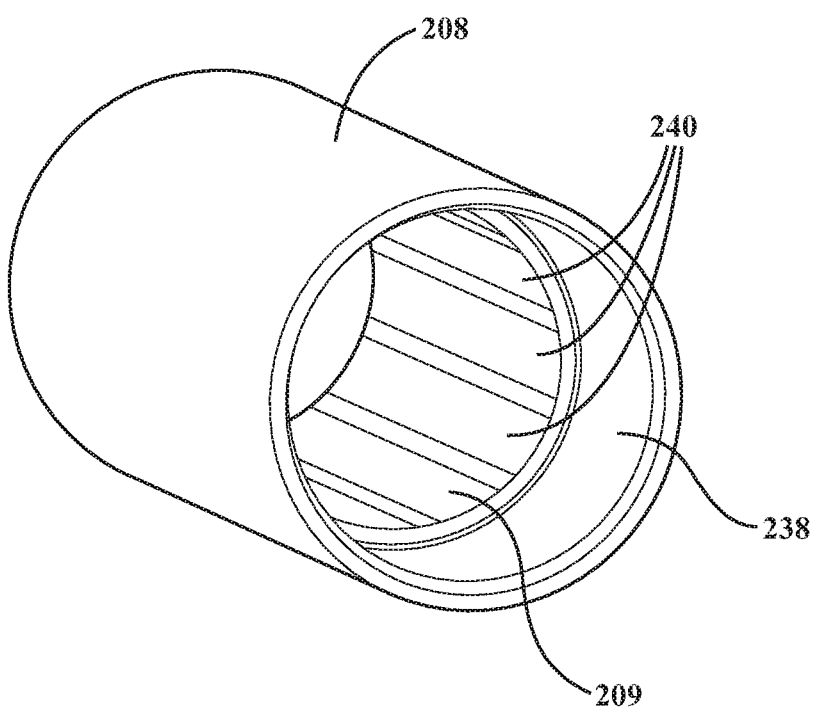
FIG. 47 is a perspective view of a wedge sleeve of the drive connector.
Figure 48:
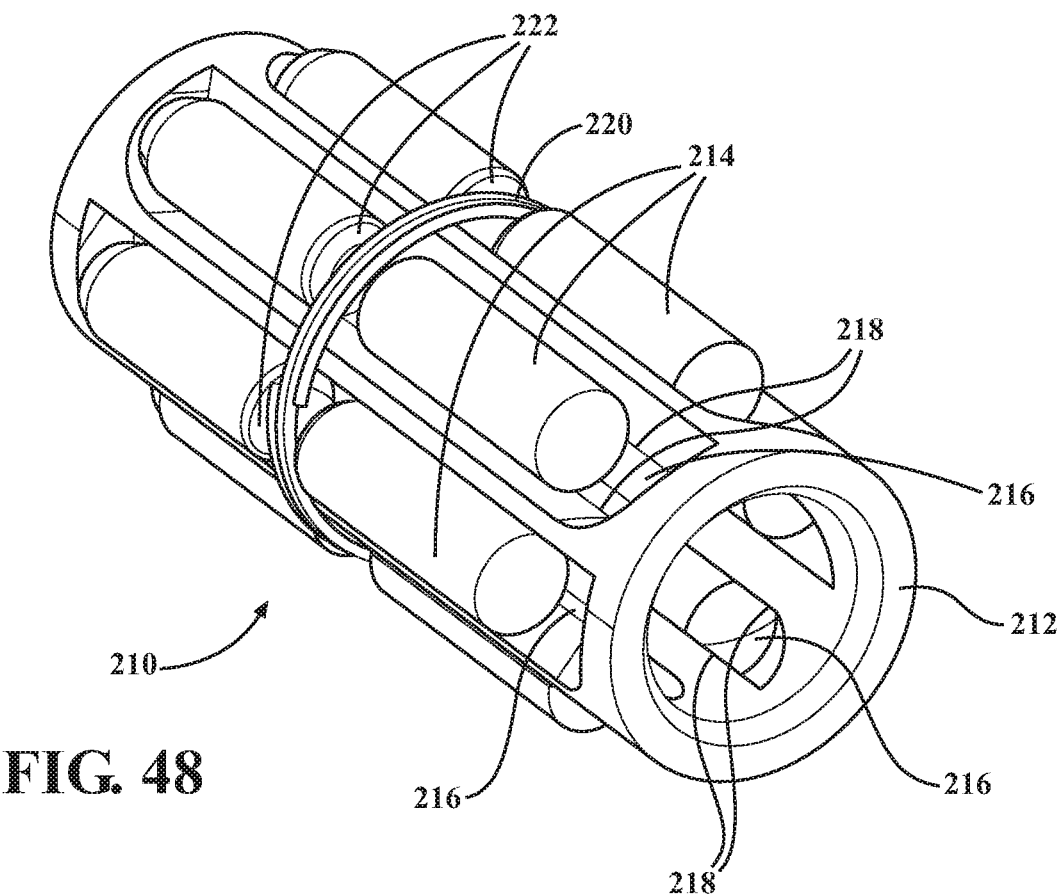
FIG. 48 is a perspective view of a portion of a clutch assembly of the drive connector.
Figure 49:
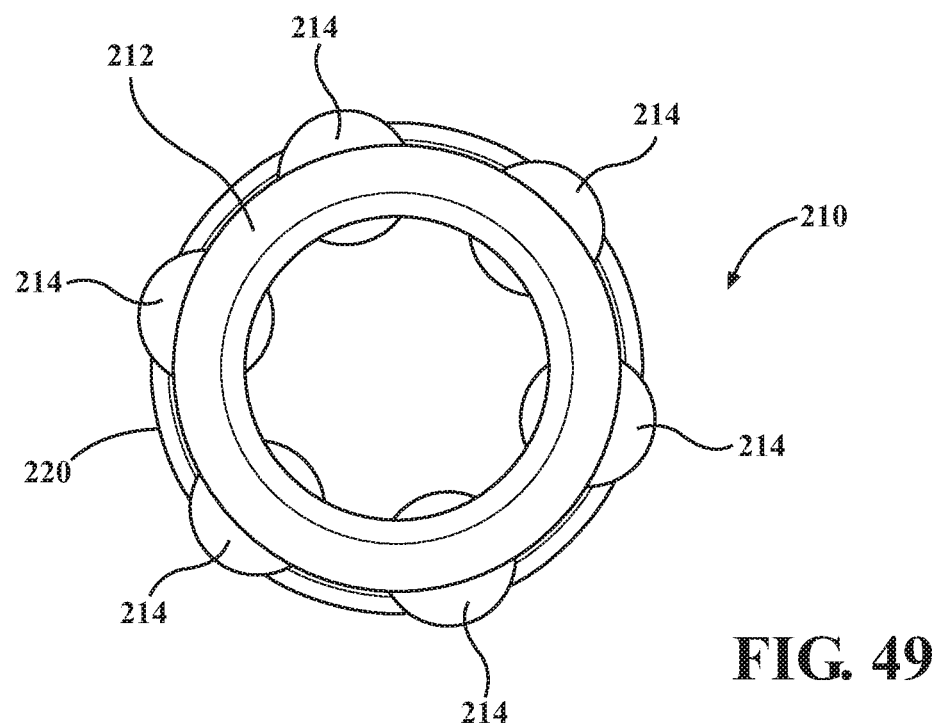
FIG. 49 is an end view of the portion of the clutch assembly of the drive connector shown in FIG. 48.
Figure 50:
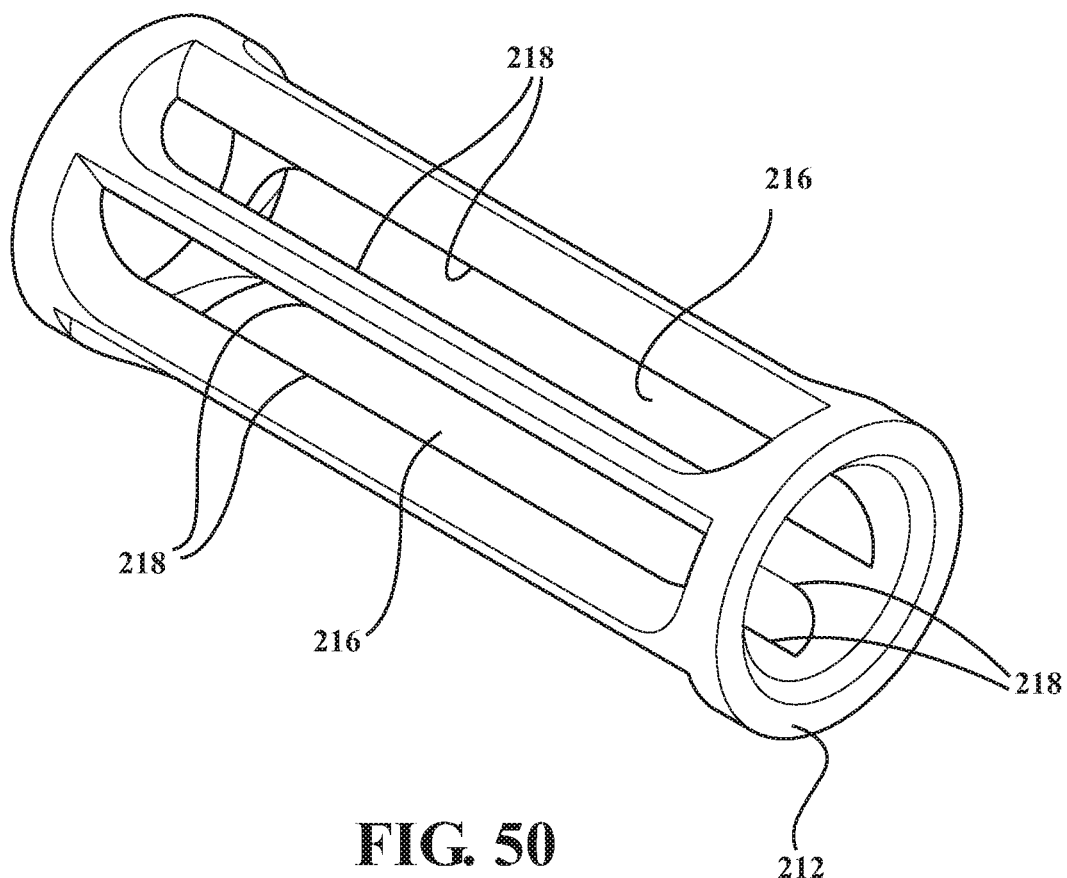
FIG. 50 is a perspective view of a cage of the clutch assembly.
Figure 51:
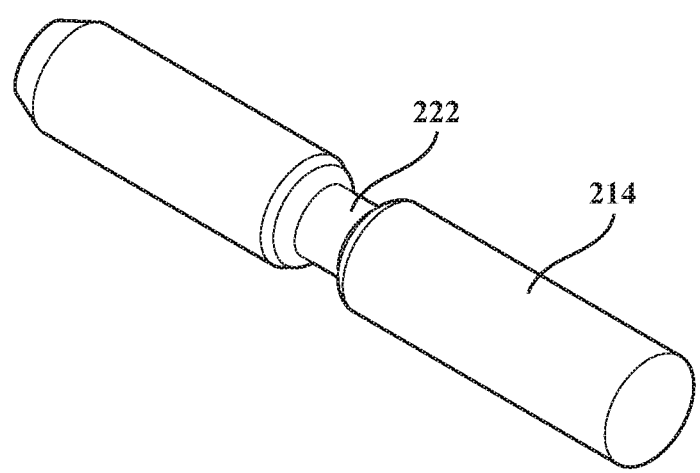
FIG. 51 is a perspective view of a roller of the clutch assembly.

The drive connector 112 includes an interior wall 209 that receives the clutch assembly 210 and is configured to selectively bias the rollers 214 against the shaft 42. Specifically, the wedge sleeve 208 defines the interior wall 209. The wedge sleeve 208, shown in isolation in FIG. 47, is disposed between the drive member 202 and the socket 226, as shown in FIGS. 41-43, and is fixed to the drive member 202. The wedge sleeve 208 is fixed to the drive member 202 in any fashion such as, for example, press-fit, welding, adhering, pinning, etc.

With reference to FIGS. 47 and 52-55, the wedge sleeve 208 defines a bore 238 and presents contact surfaces 240 disposed circumferentially about the bore 238. The contact surfaces 240 shown in FIGS. 47 and 52-55 are facets, i.e., planar. Alternatively, the contact surfaces 240 can have any shape sufficient to pinch the rollers 214 between the contact surfaces 240 and the shaft 42 of the tool 38 when the wedge sleeve 208 rotates relative to the clutch assembly 210. For example, the contact surfaces 240 can be arced about the nose tube axis N. The wedge sleeve 208 of FIGS. 47 and 52-55 includes twelve contact surfaces 240, i.e., is a dodecagon. Alternatively, the wedge sleeve 208 can include any number of contact surfaces 240.

Figure 52:
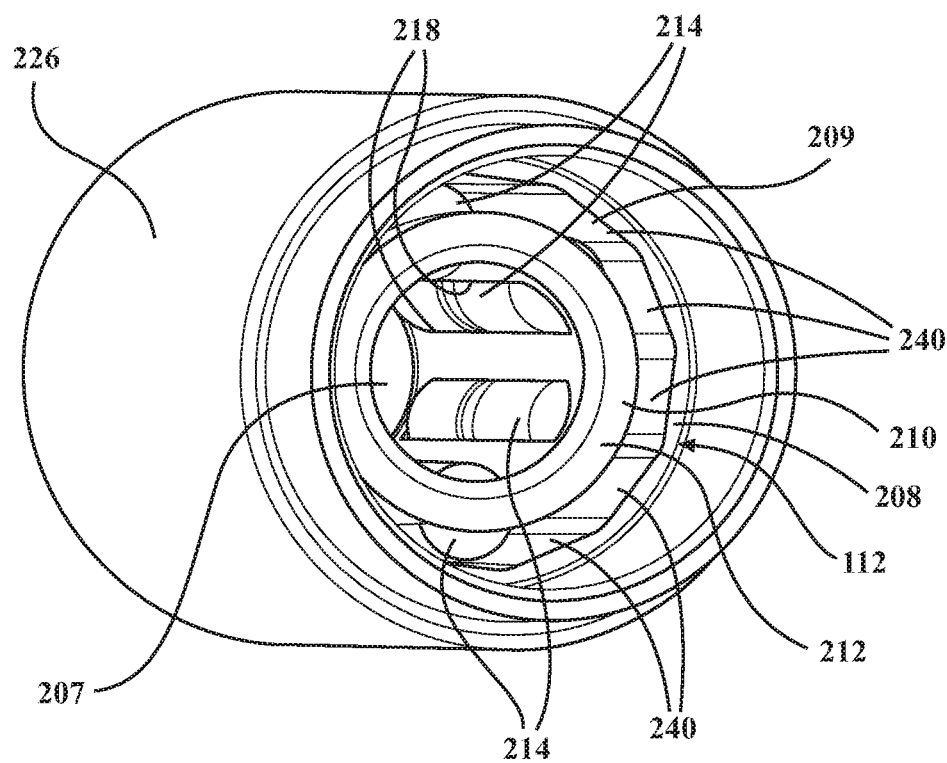
FIG. 52 is a perspective view of the drive connector disposed in the socket of the drive member.
Figure 53:
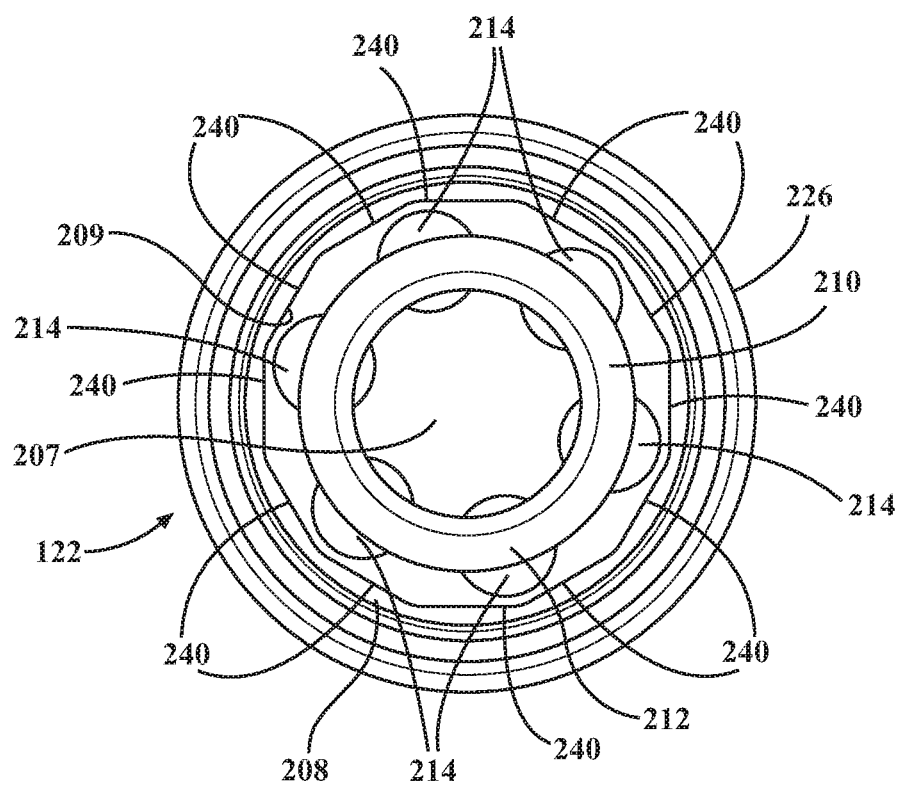
FIG. 53 is an end view of FIG. 52.
Figure 54:
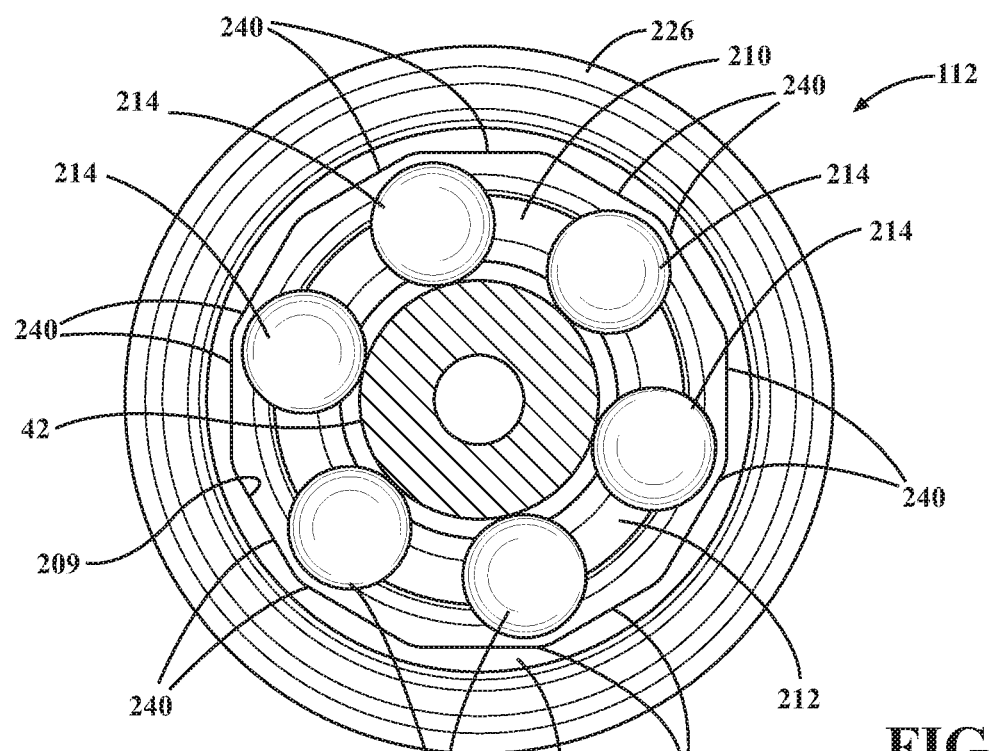
FIG. 54 is the end view of FIG. 53 with the shaft of the tool engaged with the drive connector when the shaft is initially inserted into the drive connector.
Figure 55:
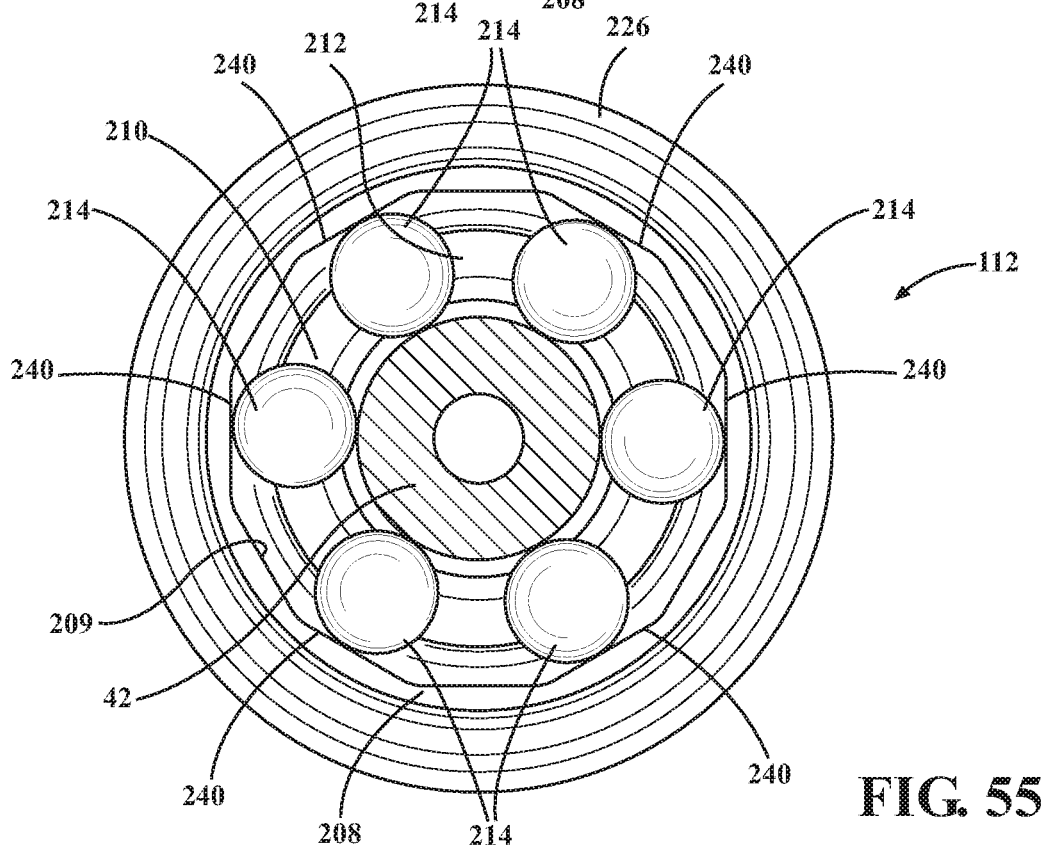
FIG. 55 is the end view of FIG. 53 with the shaft of the tool engaged with the drive connector and with the drive member delivering rotation to the shaft.

The contact surfaces 240 are configured to contact the rollers 214 when the wedge sleeve 208 rotates relative to the clutch assembly 210. The rollers 214 are spaced from the contact surfaces 240 before the shaft 42 of the tool 38 is inserted into the clutch assembly 210, as shown in FIGS. 52 and 53. As shown in FIG. 54, the rollers 214 remain spaced from the contact surfaces 240 when the shaft 42 is initially inserted into the clutch assembly 210. When the clutch assembly 210 rotates relative to the wedge sleeve 208, the rollers 214 rotationally lock the shaft 42 of the tool 38 to the drive system 200, as shown in FIG. 55.

For example, when the actuator 34 drives the drive member 202, the drive member 202 rotates the wedge sleeve 208 relative to the clutch assembly 210. As the wedge sleeve 208 rotates relative to the clutch assembly 210, the contact surfaces 240 contact the rollers 214 and pinch the rollers 214 between the contact surfaces 240 and the shaft 42 of the tool 38 to rotationally lock the shaft 42 of the tool 38 to the drive member 202. In other words, the contact surfaces 240 cause the rollers 214 to frictionally engage the shaft 42 of the tool 38. The clutch assembly 210 is self-engaging and self-releasing. The operator merely inserts the shaft 42 along the nose axis N into engagement with the clutch assembly 210 to engage the shaft with the clutch assembly 210, i.e., no twisting is necessary. As set forth above, the axial connector 110 retains the cutting accessory 32 to the nose tube 100 axially along the nose tube axis N.

The clutch assembly 210 is configured to releasably engage the cylindrical outer surface 43 of the shaft 42 of the tool 38. Specifically, the shaft 42 presents the outer surface 43 having a cylindrical cross-section that releasably engages the drive connector 112. The outer surface 43 typically has a constant outer diameter extending from the shroud 40 to the free end 45. In other words, the clutch assembly 210 does not require that the shaft 42 of the tool 38 have flats or other features designed to transfer rotational movement to the shaft 42. The clutch assembly 210 is engageable with any portion of the shaft 42 that is cylindrical. The shaft 42 is typically cylindrical between the proximal end 44 and the distal end 46, i.e., along the entire length of the shaft 42, such that particular alignment of the shaft 42 along the nose tube axis N is not required to engage the shaft 42 with the clutch assembly 210. In other words, the shaft 42 engages the clutch assembly 210 without the need of aligning specific features on the shaft 42 in a particular location along the nose tube axis N.

The drive system, including the drive member 202, the wedge sleeve 208, and the clutch assembly 210, enables the use of a cutting accessory 32 having high rigidity, decreases interference with the line of sight by the cutting accessory 32, increases surgical sight access by reducing bulk at the end of the nose tube 100, and allows for precise axial positioning, e.g., when used with the axial connector 110.

The use of drive system 200, and specifically the drive member 202, the wedge sleeve 208, and the clutch assembly 210, is not limited to the end effector 12. In other words, the drive system 200 can be implemented on any type of device. For example, a hand-held power tool (not shown) can include the drive system 200. The hand-held power tool can be, for example, a surgical hand-held power tool.

The drive system 200 is not limited to use with irrigated cutting accessories. For example, the drive system 200 can be used to couple to solid cutting tools. One such type of cutting tool could include, for example, a shaft having a 2 mm diameter.

The end effector 12 and the cutting accessory 32 define a liquid delivery path L for delivering liquid through the end effector 12 and the cutting accessory 32 to the surgical site. One embodiment of the liquid delivery path L is shown in FIGS. 5 and 6 and another embodiment of the liquid delivery path L is shown in FIG. 31. A bore 242, i.e., a lumen 242, of the drive member 202, the bore of the tool 38, and the ports of the cutting head 72 define the liquid delivery path L.

With reference to FIGS. 43-45, the drive member 202 includes a nipple 244 for receiving the liquid, as discussed further below. The drive member 202 defines the bore 242 extending from the nipple 244 along the tool axis T and through the drive member 202. As set forth above, the drive member 202 receives the shaft 42 of the cutting accessory 32 in the bore 242 of the drive member 202, i.e., is releasably engaged with the cutting accessory 32, and the drive member 202 delivers the liquid from the nipple 244 to the shaft 42. During cutting, the liquid can be delivered into the bore 242 of the drive member 202 at the nipple 244 and the liquid flows through the bore 242 of the drive member 202, through the bore 70 of the shaft 42, and out of the ports 74 of the cutting head 72 onto the surgical site.

With reference to FIG. 43, a static seal 246, also referred to as a first seal herein, is disposed in the bore of the drive member 202 and the static seal 246 seals between the drive member 202 and the cutting accessory 32 when the cutting accessory 32 is received in the bore of the drive member 202 to prevent the liquid from leaking between the drive member 202 and the shaft 42 of the cutting accessory 32.

The static seal 246 defines a bore 248 and the static seal 246 is configured to seal to the exterior of the shaft 42 of the tool 38 when the shaft 42 is inserted into the bore 248. With reference to FIGS. 43-45, the drive member 202 defines a pocket 250 receiving the static seal 246. The static seal 246 slideably receives the cutting accessory 32 in the bore 248 along the nose tube axis N. Specifically, the drive member 202 defines the pocket 250. The static seal 246 is rotationally fixed to the drive member 202 and the cutting accessory 32 for sealing between the drive member 202 and the cutting accessory 32.

The static seal 246 is "static" in that the drive member 202 and the shaft 42 of the cutting accessory 32 move together as a unit and the static seal 246 statically seals between the drive member 202 and the cutting accessory 32. The static seal 246, for example, is a high temperature elastomeric material such as, for example, silicone or Viton®, that is autoclave compatible.

With reference to FIGS. 5-6 and 56-58, the end effector 12 includes a cartridge 252, i.e., a fluid delivery member, coupled configured to be coupled to the drive member 202 for delivering fluid to the bore 242 of the drive member 202. The cartridge 252 is removably engageable with the drive member 202. Specifically, the cartridge 252 is configured to removably connect to the nipple 244. The cartridge 252 is configured to deliver liquid, electricity, and/or data communication to the rest of the end effector 12. For example, when the cartridge 252 is connected to the nipple 244, the cartridge 252 is in communication with the liquid delivery path L for delivering liquid to the liquid delivery path L.

With continued reference to FIGS. 5 and 6, a housing 254 is attached to the nose tube 100 and defines a cavity 256 that removably receives the cartridge 252. The cartridge 252 and the cavity 256 are, for example, configured such that the cartridge 252 is retained in the cavity 256 by a friction fit. Alternatively, or in addition, the cartridge 252 and the cavity 256 can include any type of feature for selectively retaining the cartridge 252 in the cavity 256.

The cartridge 252, for example, engages the nipple 244 of the drive member 202 for delivering liquid to the bore 242 of the drive member 202. The cartridge 252 is connected to a source of liquid (not shown) and the source of liquid delivers liquid to the cartridge 252. The source of liquid, for example, is a peristaltic pump controlled by the manipulator controller 30. Tubing (not shown) typically connects the cartridge 252 to the source of liquid.

Figure 56:
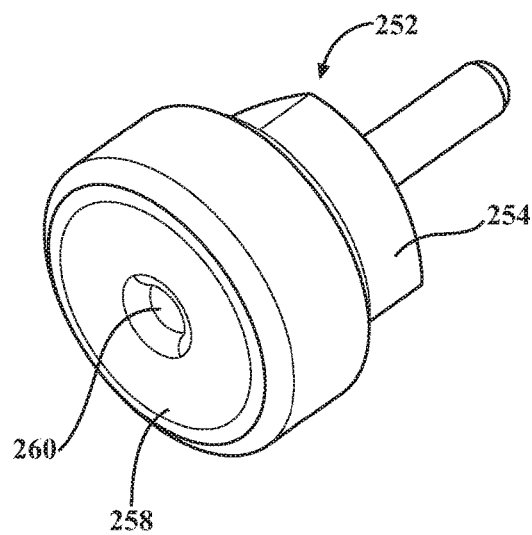
FIG. 56 is a perspective view of a cartridge.
Figure 57:
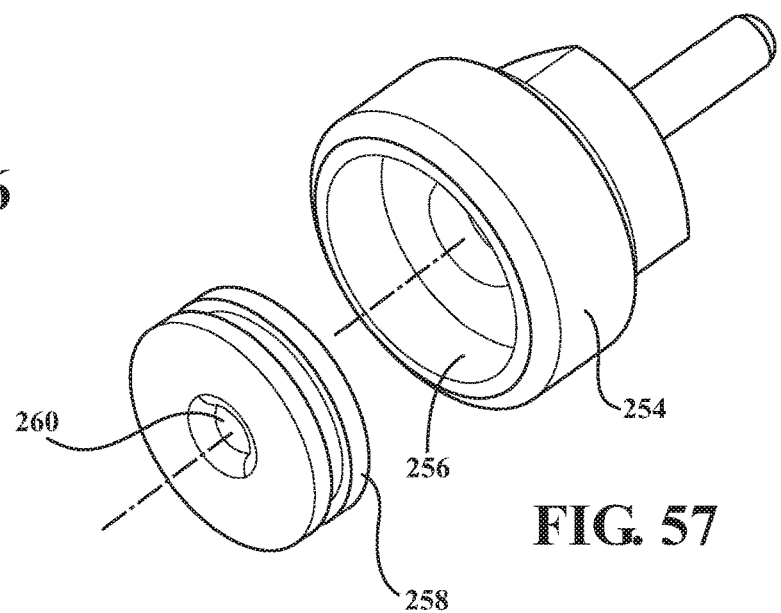
FIG. 57 is an exploded view of the cartridge including a dynamic seal.
Figure 58:
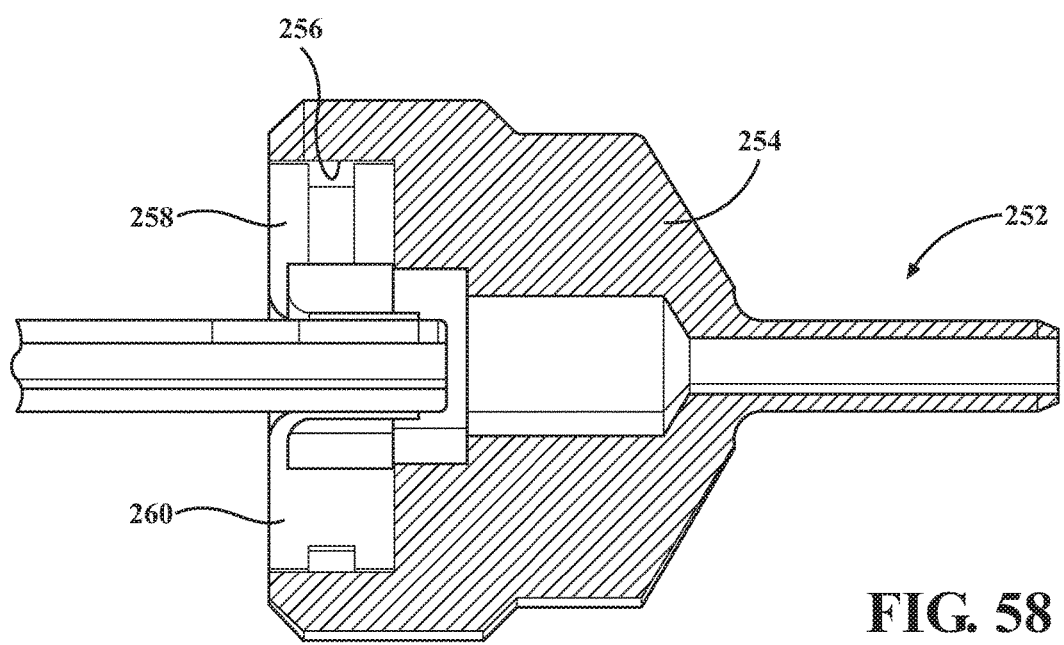
FIG. 58 is a cross-sectional view of the cartridge engaged with drive member.
Figure 59:
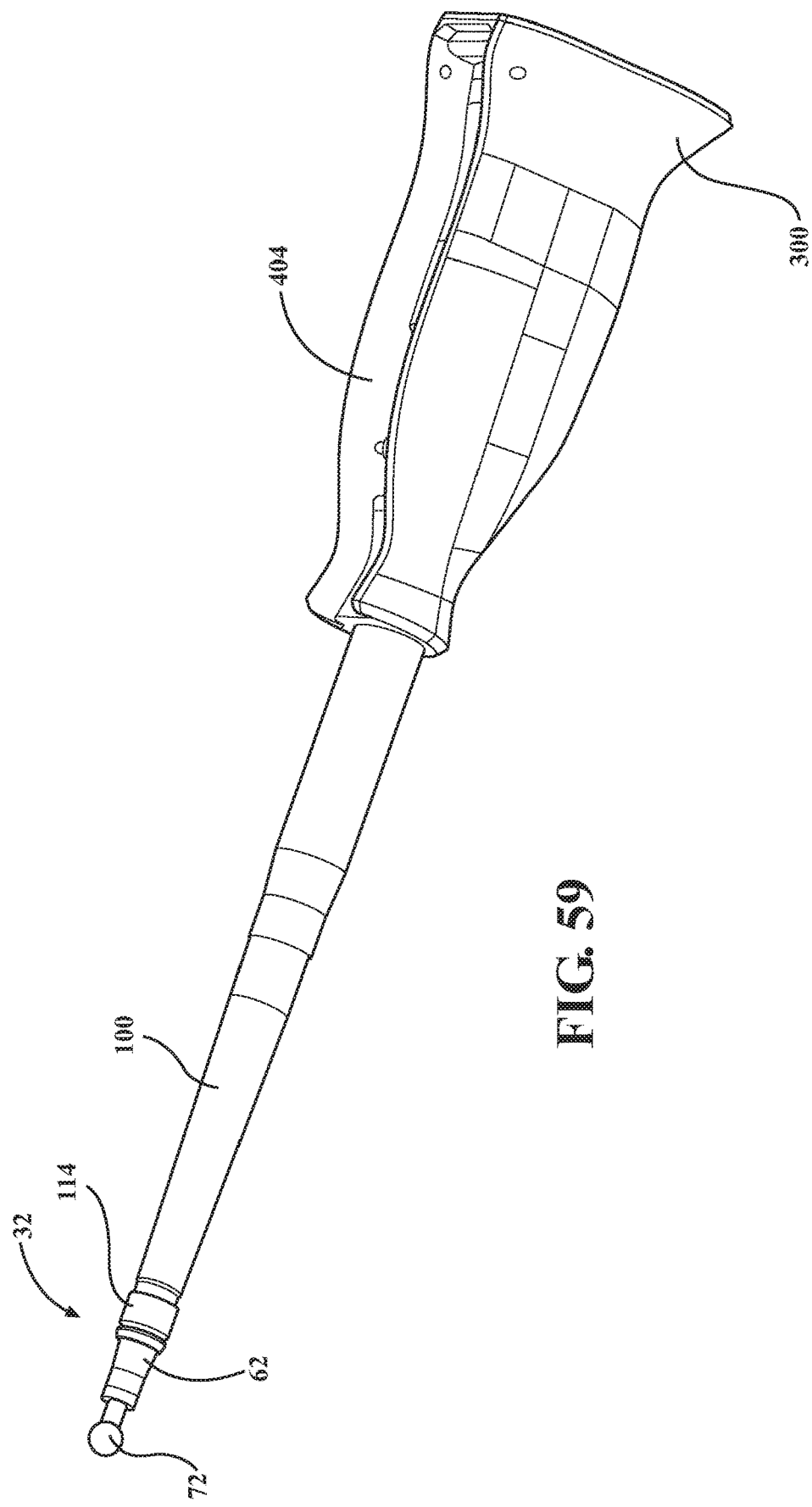
FIG. 59 is a perspective view of a handle on the nose tube.
Figure 60:
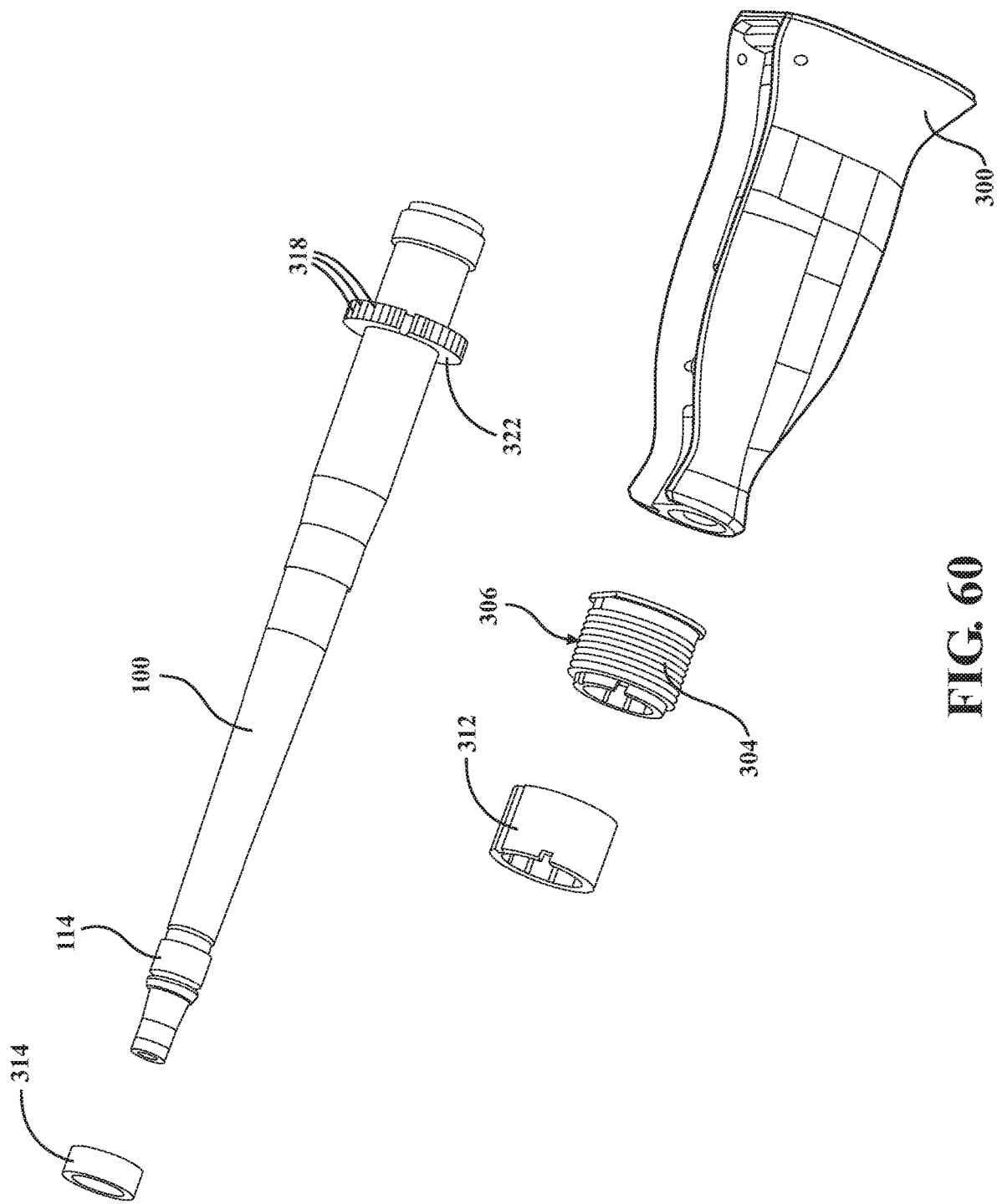
FIG. 60 is an exploded view of the handle and the nose tube.

With reference to FIGS. 56-58, the cartridge 252 includes a dynamic seal 258, also referred to as a second seal herein, for connecting to the nipple 244 of the drive member 202. The dynamic seal 258 defines a bore 260 that receives the nipple 244. When the cartridge 252 is coupled to the drive member 202, the dynamic seal 258 is disposed around the nipple 244 between the nipple 244 and the cartridge 252. The dynamic seal 258 is, for example, Teflon® infused polyamide.

The dynamic seal 258 rotatably engages at least one of the drive member 202 and the cartridge 252 for sealing between the drive member 202 and the cartridge 252 during relative rotation therebetween. The dynamic seal 258 typically remains stationary relative to the cartridge 252 and the nipple 244 rotates relative to the dynamic seal 258 when the drive member 202 rotates. The dynamic seal 258 is configured to seal between the nipple 224 and the cartridge 252 when the nipple 224 rotates relative to the cartridge 252. Typically, the dynamic seal 258 is retained in the cartridge 252, i.e., dynamic seal 258 moves with the cartridge 252 when the cartridge 252 is uncoupled from the drive member 202.

The drive member 202 extends along the nose tube axis N. The static seal 246 extends about the nose tube axis N. The dynamic seal 258 extends about the nose tube axis N when the cartridge 252 is coupled to the drive member 202. The static seal 246 and the dynamic seal 258 are spaced from each other along the nose tube axis N when the cartridge is coupled to the drive member 202. The static seal 246 is disposed along the axis between the drive connector 112 and the dynamic seal 258.

The cartridge 252, for example, includes data communication connectors (not shown) and the housing 254 supports corresponding data communication connectors (not shown) for transferring data to and from the end effector 12. For example, the end effector 12 can transfer data from a NVRAM chip or an RFID reader to the manipulator controller 30, as discussed further below. A flex circuit, for example, is connected to the data communication connector of the cartridge 252 for transferring data to and from the data communication connector. The flex circuit, for example, can be coupled to and extend along at least a portion of the tubing and/or wiring. The data communication connectors of the cartridge 252 and the corresponding data communication connectors of the housing can be any type of data communication connectors such as pins/corresponding sockets, plugs/receptacles, etc.

Alternatively, in the embodiment shown in FIG. 31, the shaft 42 of the cutting accessory 32 extends through the drive connector 112 to the dynamic seal 258 of the cartridge 252. Such a configuration eliminates the need for a static seal.

Figure 70:
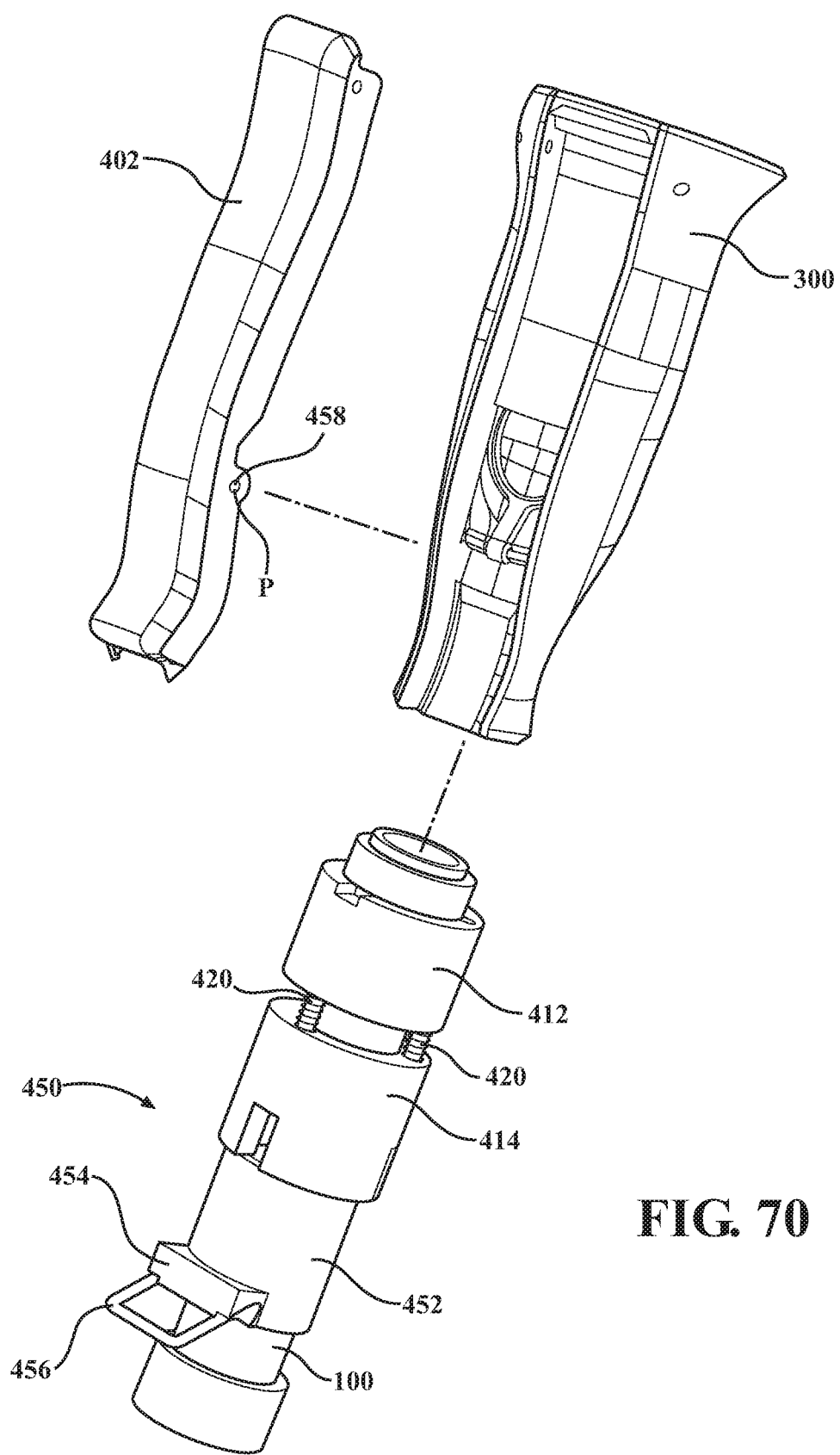
FIG. 70 is a partially exploded view a another embodiment of the grip sensing mechanism exploded from the handle.

With reference to FIGS. 59-62 and 70, the end effector 12 includes a handle 300 rotatably coupled to the nose tube 100. The handle 300 is rotatably supported by the nose tube 100 about the nose tube axis N. The handle 300 defines a bore 302 that receives the nose tube 100. The handle 300 is grasped by the hand of an operator to move the end effector 12 with the use of the force-torque sensor 408 as discussed above. The handle 300 typically has an ergonomic shape for matching the contour of the hand of the operator. The handle 300 in FIGS. 59-62 is selectively lockable with the nose tube 100 to selectively prevent rotation of the handle 300 relative to the nose tube 100 about the nose tube axis N. The handle 300 in FIG. 70 is freely rotatable about the nose tube 100 at all times.

Figure 69:
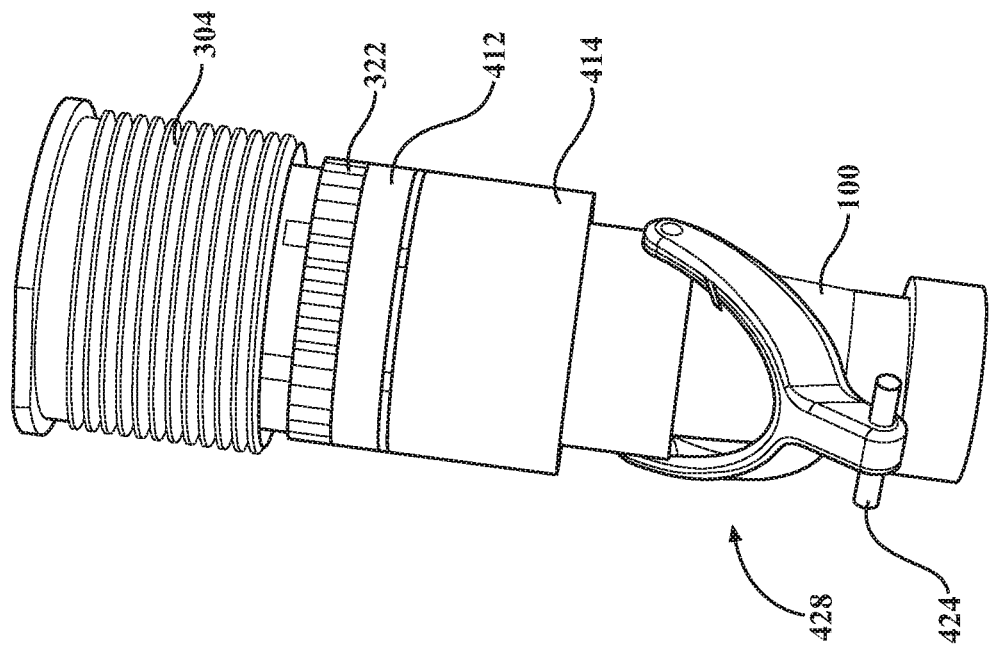
FIG. 69 is the perspective view of FIG. 60 with the activator holder in a proximate position relative to the sensor holder.
Figure 68:
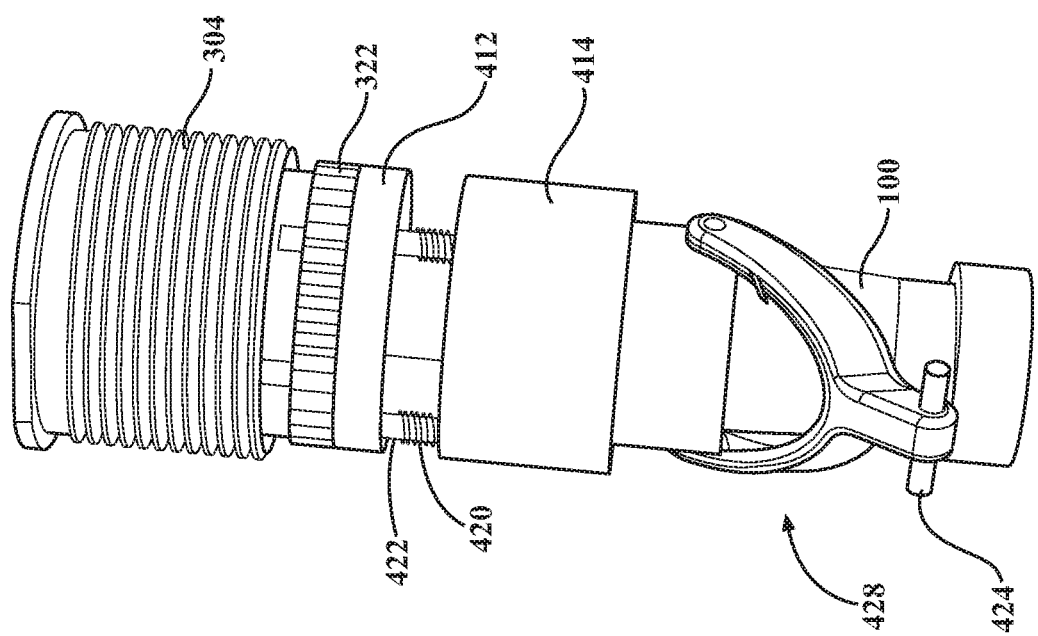
FIG. 68 is a perspective view of a portion of the grip sensing mechanism with an activator holder in a spaced position relative to the sensor holder.

With reference to FIGS. 68 and 69, a sleeve 304 is coupled to the nose tube 100 and defines threads 306 concentric with the nose tube axis N. The sleeve 304 is axially fixed along the nose tube axis N relative to the nose tube 100.

Figure 66:
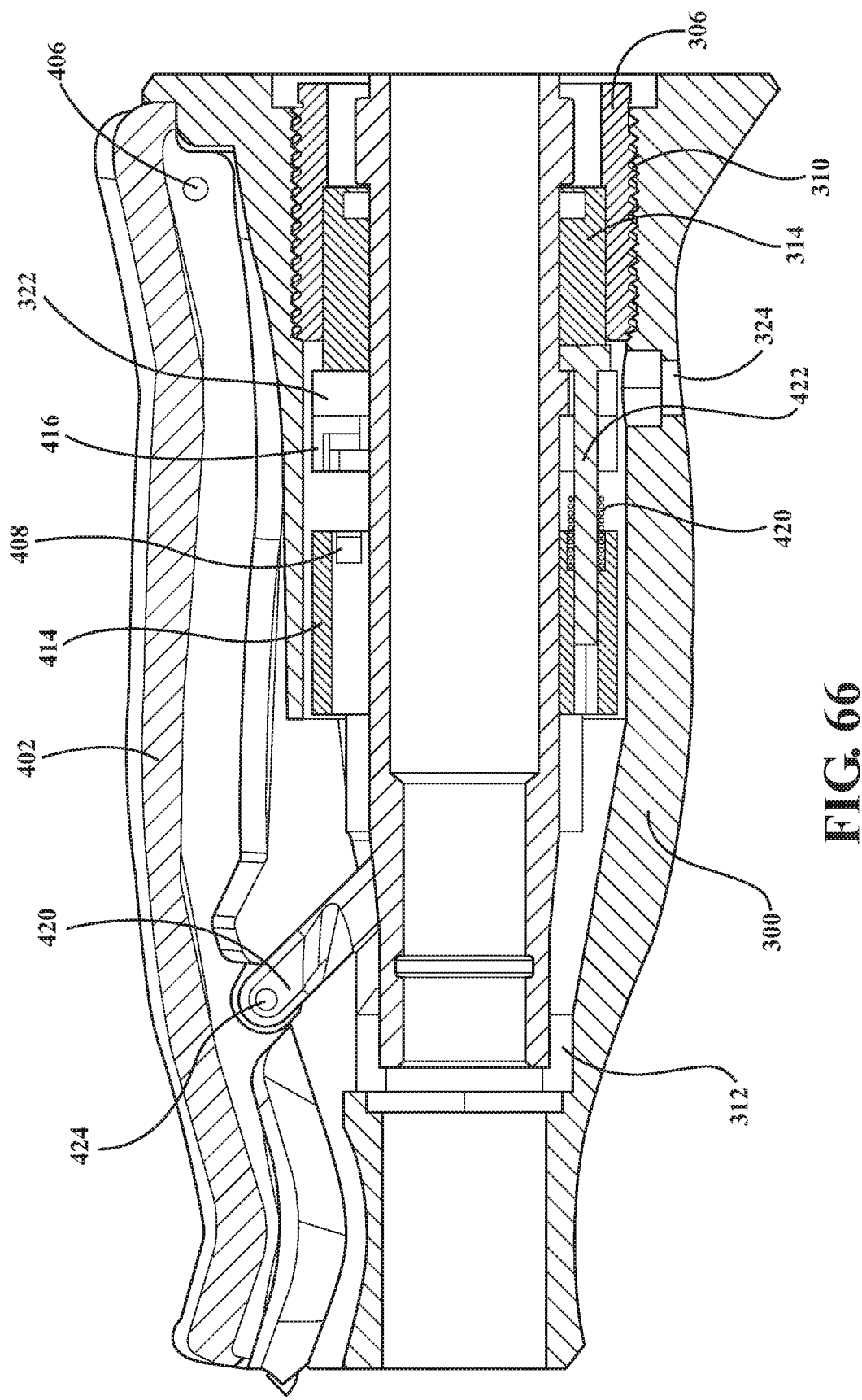
FIG. 66 is a cross-sectional view of the grip sensing mechanism and the handle with the lever in a released position.
Figure 67:
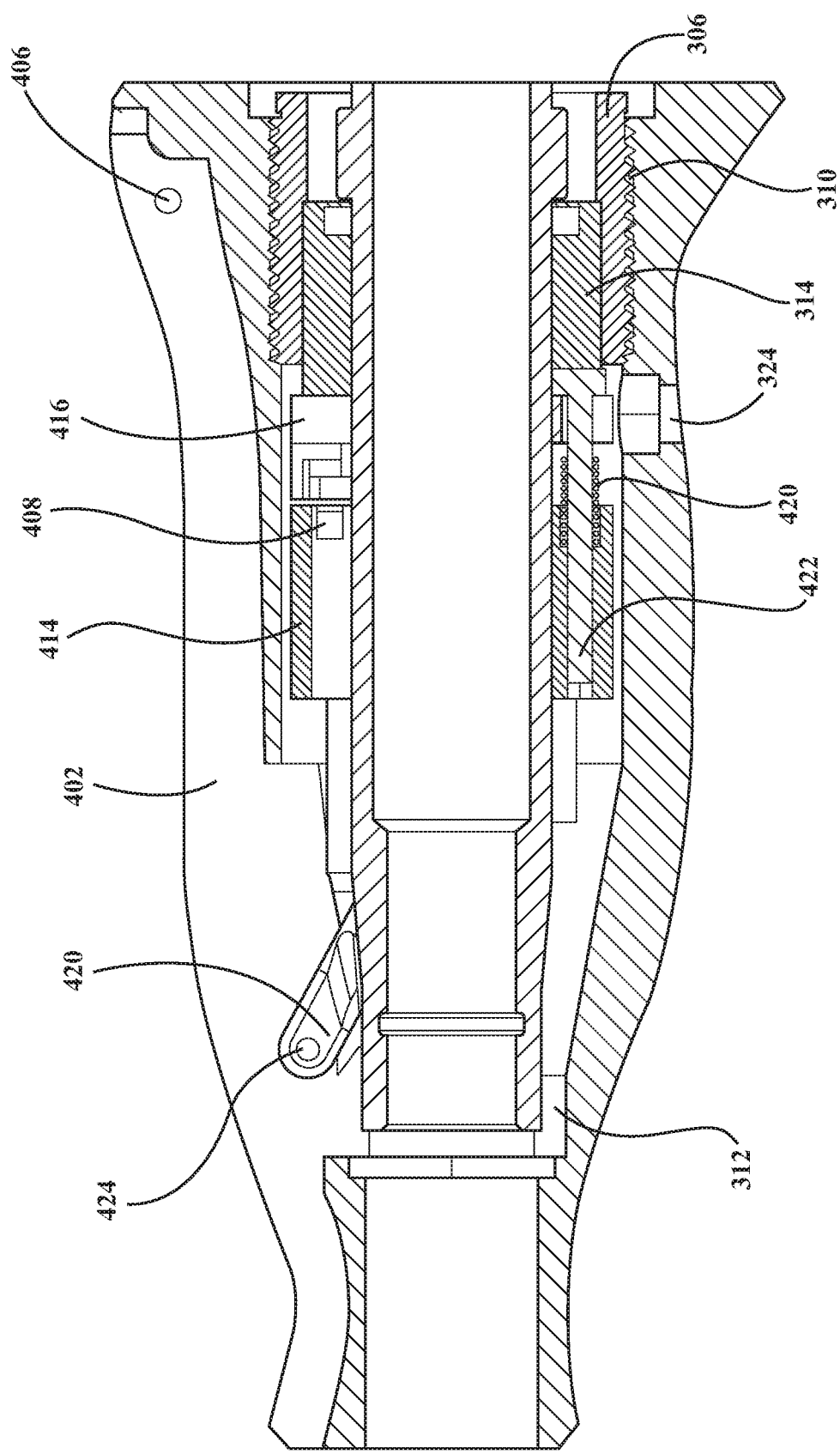
FIG. 67 is a cross-sectional view of the grip sensing mechanism and the handle with the lever in a depressed position.

With reference to FIGS. 66 and 67, the handle 300 includes an inner surface 308 defines threads 310 engaging the groove 306 of the sleeve 304 to couple the handle 300 to nose tube 100. The sleeve 304 is typically disposed at the distal end 106 of the nose tube 100 and alternatively, can be disposed at any position along the nose tube 100. A bushing 312 is disposed between the nose tube 100 and the sleeve 304 and is rotatable relative to at least one of the nose tube 100 and the sleeve 304.

Figure 61:
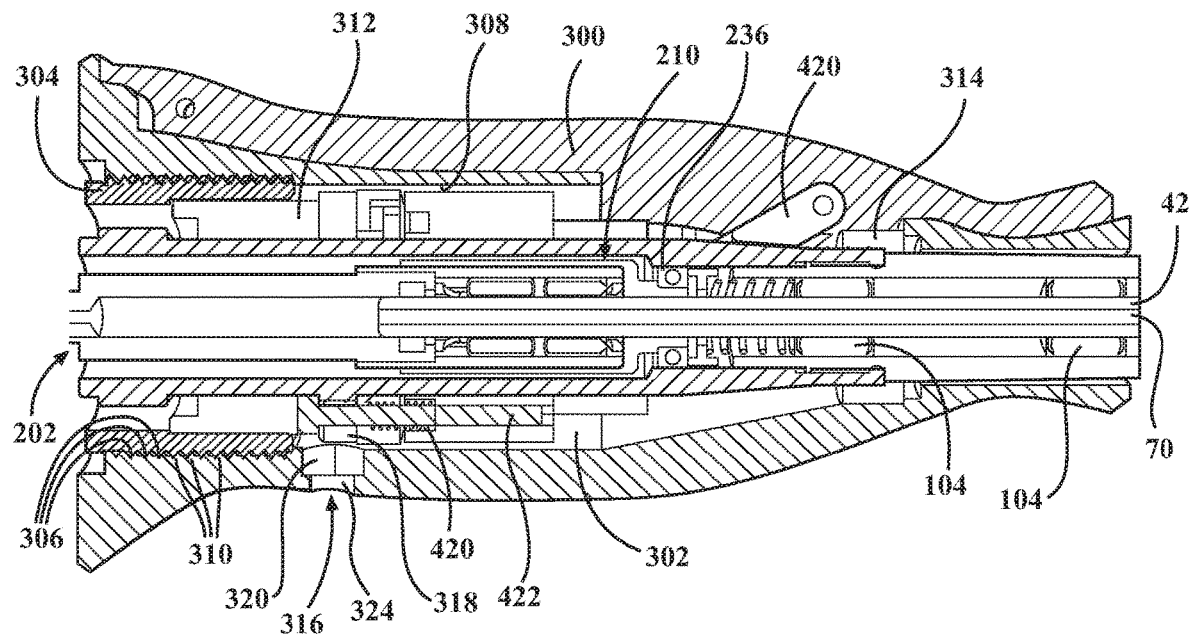
FIG. 61 is a cross-sectional view of the handle and the nose tube.
Figure 62:
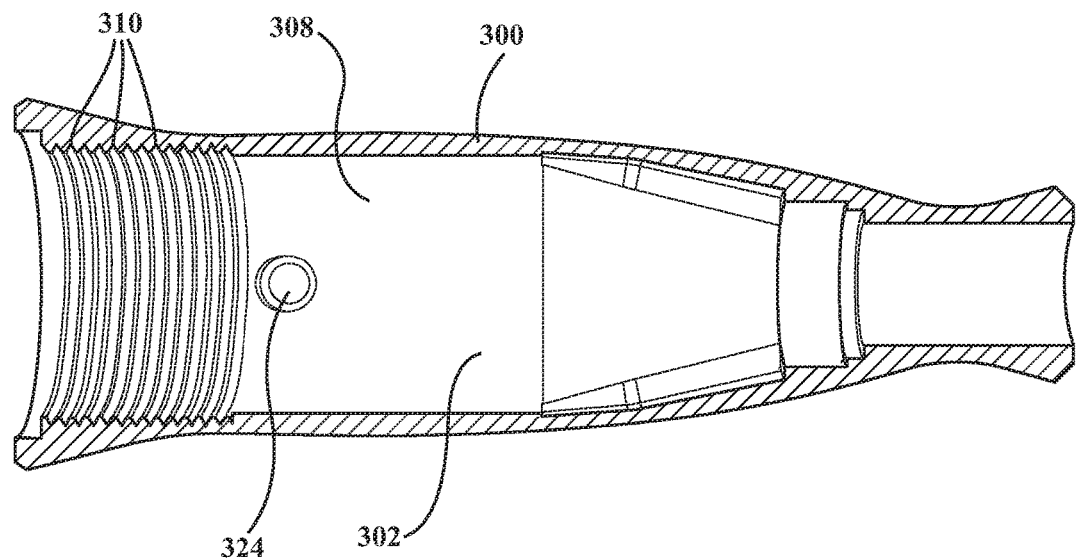
FIG. 62 is a cross-sectional view of the handle.
Figure 63:
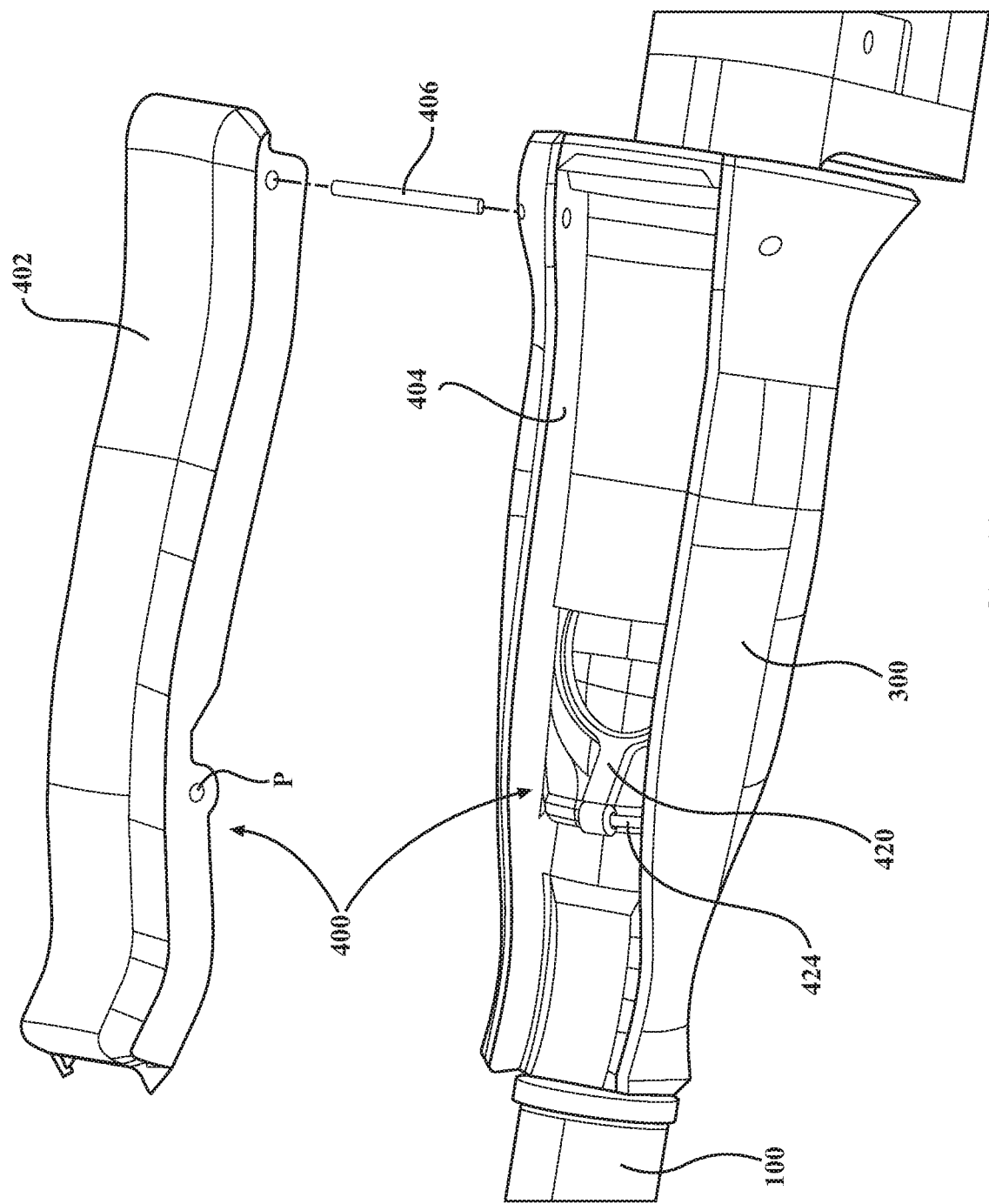
FIG. 63 is a partially exploded view of a lever and the handle.

With reference to FIG. 61, a bushing 314 is disposed between the nose tube 100 and the handle 300 for rotatably coupling the handle 300 to the nose tube 100. The bushing 314 is spaced from the sleeve 304 and is typically disposed along the nose tube 100 between the sleeve 304 and the distal end 106 of the nose tube 100. The inner surface 308 of the handle 300 engages the bushing 314. The bushing 314, for example, is fixed to the nose tube 100, e.g., by friction fit, and the inner surface 308 of the handle 300 rotatably engages the bushing 314. Alternatively, for example, the bushing 314 is fixed to the inner surface 308 of the handle 300, e.g., by friction fit, and the bushing 314 rotatably engages the nose tube 100.

The handle 300 provides a passive sixth axis. In other words, movement can be transmitted from the hand of an operator to the handle 300 in five degrees of freedom (DOF) and the handle 300 is passive, i.e., does transmit movement, about a sixth degree of freedom, i.e., rotation about the nose tube axis N. In other words, any torque applied to the handle 300 rotates the handle 300 relative to the nose tube 100. With reference to FIG. 3, the handle 300 transmits movement to the rest of the end effector 12, e.g., the nose tube 100, in translation along the x-axis, y-axis, and z-axis and in rotation about the x-axis and the y-axis. The handle 300 is passive, i.e., does not transmit movement to the nose tube 100, in rotation about the z-axis.

With reference to FIGS. 64-67, the handle 300 and the nose tube 100 define locking features 316 for selectively locking the handle 300 to the nose tube 100. For example, the nose tube 100 defines teeth 318 extending circumferentially about the nose tube 100 and the handle 300 includes a locking member 320 for engaging the teeth 318 to rotationally lock the handle 300 to the nose tube 100. The nose tube 100 includes a circumferential ring 322, for example, that presents the teeth 318.

The locking member 320 is aligned with the teeth 318 along the nose tube axis N. The locking member 320, for example, is a set screw threadedly engaged with a threaded access hole 324 in the handle 300. The set screw can be threadedly advanced and retracted relative to the access hole 324 to engage and disengage the teeth 318.

With reference to FIGS. 63-77, the end effector 12 includes a grip sensing mechanism 400, 450. One embodiment of the grip sensing mechanism 400 is shown in FIGS. 63-69 and a second embodiment of the grip sensing mechanism 450 is shown in FIGS. 69-77. When the robot 11 is operated in manual mode, the grip sensing mechanism 400, 450 is operable to prevent movement of and operation of the cutting accessory 32 when the grip sensing mechanism 400, 450 is released by the operator, e.g., if the operator accidentally loses grip of the end effector 12. In other words, during use, the manipulator 10 can move the cutting accessory 32 and the actuator 34 can be powered to drive the cutting accessory 32 as long as the operator continues to actuate the grip sensing mechanism 400, 450. If the operator releases the grip sensing mechanism 400, 450, the manipulator 10 does not move the cutting accessory 32 and operation of the actuator 34 is prevented. This ensures that the cutting accessory 32 is not moved or driven, e.g., does not rotate, unless a hand of an operator is gripping the handle 300 of the end effector 12.

The grip sensing mechanism 400, 450 is typically supported on the handle 300. The grip sensing mechanism 400, 450 is configured to be actuated when engaged by the hand of the operator when the operator grasps the handle 300.

The grip sensing mechanism 400, 450 includes a lever 402, i.e., a trigger 402, moveably mounted to the handle 300 and a sensor 408 that is actuated in response to movement of the lever 402. In other words, the sensor 408 is supported by the nose tube 100 and is configured to identify the position of the lever 402 in the gripped position and the released position. With reference to FIG. 66, the handle 300 defines a slot 404 and the lever 402 is disposed in the slot 404.

With reference to FIGS. 66-67 and 74-75, the lever 402 is typically pivotably mounted to the handle 300 and is configured to be pivoted relative to the handle 300 when the operator grasps the handle 300. For example, the lever 402 is supported by the nose tube 100, e.g., pinned to the handle 300 with a pin 406, and the lever 402 is rotatable about the pin 406 relative to the handle 300 between a depressed position and a released position. Alternatively, the lever 402 can, for example, be configured to be slideable along the handle 300 along the nose tube axis N, can be configured to be depressed relative to the handle 300 transversely to the nose tube axis N, etc.

The sensor 408 is in a first state in response to pivoting of the lever 402 relative to the handle 300 to the depressed position. In the first state, the sensor 408 indicates to the manipulator controller 30 that the manipulator 10 can move the end effector 12 and the actuator 34 can be operated to drive the cutting accessory 32. The sensor 408 is in a second state in response to pivoting of the lever 402 relative to the handle 300 to the released position. In the second state, the sensor 408 indicates to the manipulator controller 30 that the manipulator 10 should not move the end effector 12 and that the actuator 34 cannot be operated to drive the cutting accessory 32.

An activator 410 is typically coupled to the lever 402 to actuate the sensor 408 between the first state and the second state. The activator 410 is configured to communicate with the sensor 408 in response to movement of the lever 402 between the depressed position and the released position.

The activator 410 is operably coupled to the lever 402 such that actuation of the lever 402 results in movement of the activator 410. For example, as set forth further below, the lever 402 is operably coupled to the activator 410 to translate the activator 410 relative to the sensor 408 in response to pivoting of the lever 402 relative to the handle 300.

The sensor 408, for example, is an inductive sensor and the activator 410, for example, is a metal indicator. However, it should be appreciated that the sensor 408 could be of any type such as a Hall Effect sensor, a capacitive sensor, etc., and the activator can be of any suitable type. Actuation of the lever 402, i.e., movement of the lever 402 to the depressed position, results in movement of the magnet relative to the Hall Effect sensor to actuate the Hall Effect sensor. Alternatively, the sensor 408 and activator 410 can be of any type such as, for example, a light sensor actuated by a light emitting diode (LED), a proximity sensor, etc.

Figure 64:
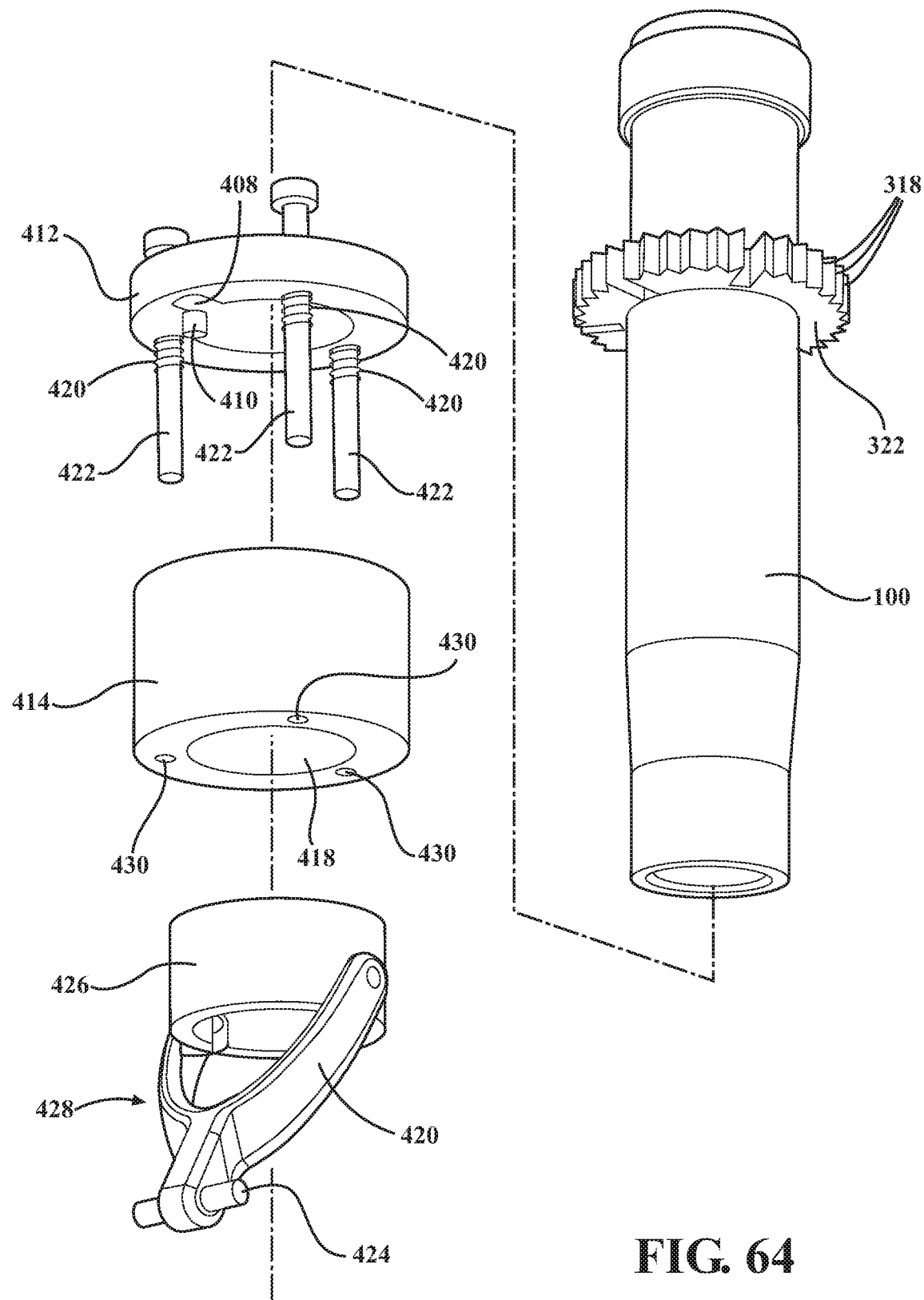
FIG. 64 is a partially exploded view of a portion of a grip sensing mechanism of a first embodiment.
Figure 65:
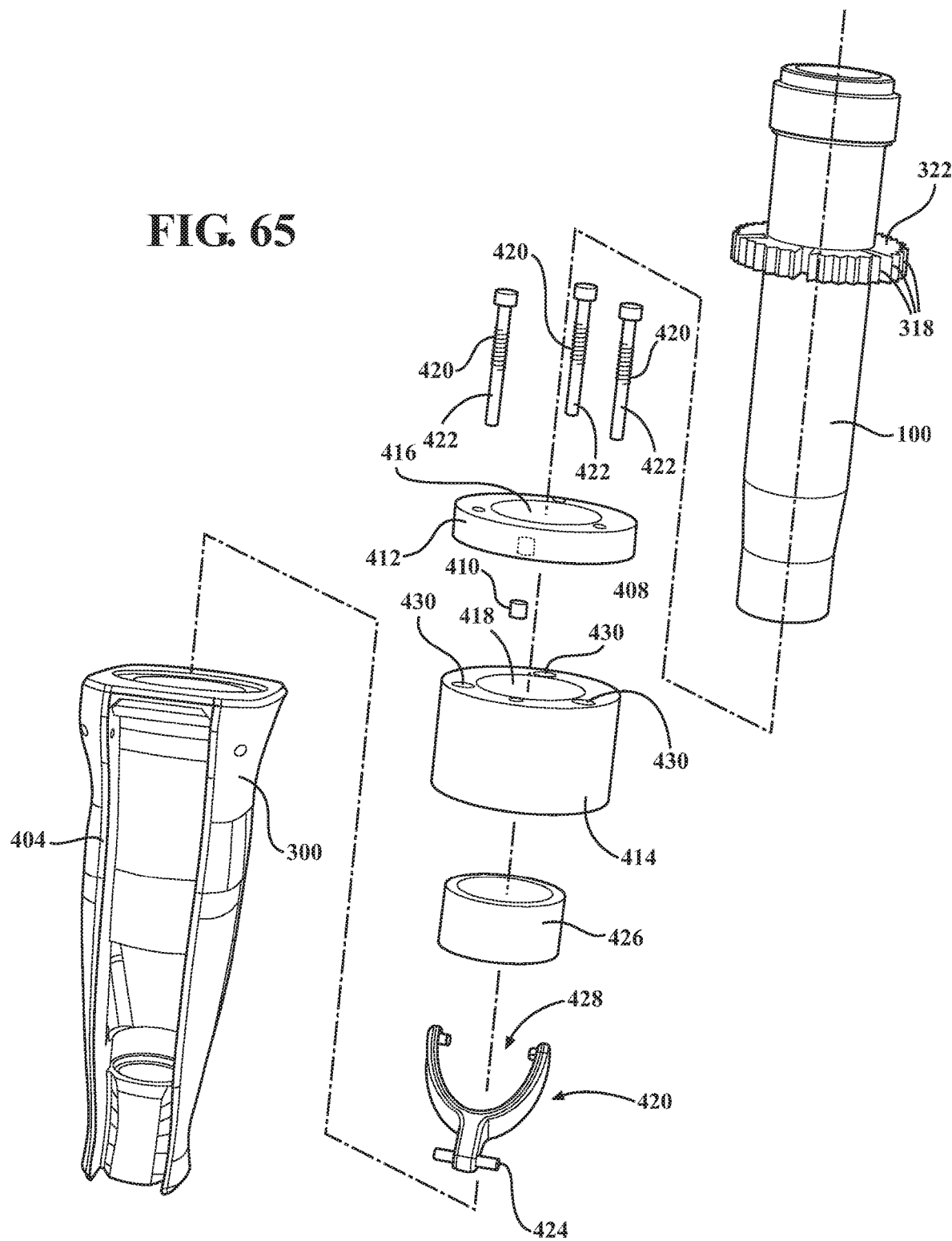
FIG. 65 is a partially exploded view of the grip sensing mechanism and the handle.
Figure 71:
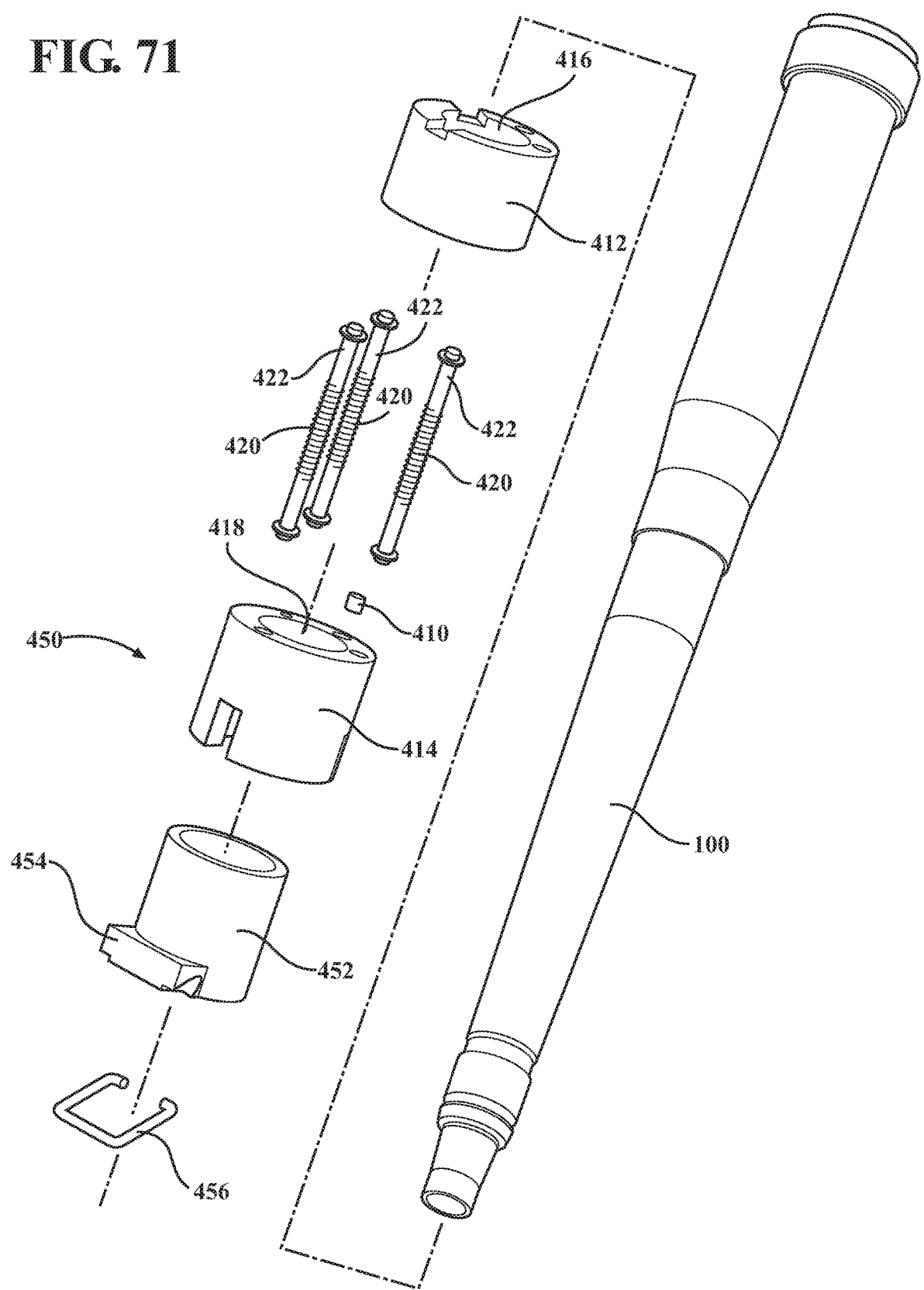
FIG. 71 is a partially exploded view of the grip sensing mechanism of FIG. 62.
Figure 72:
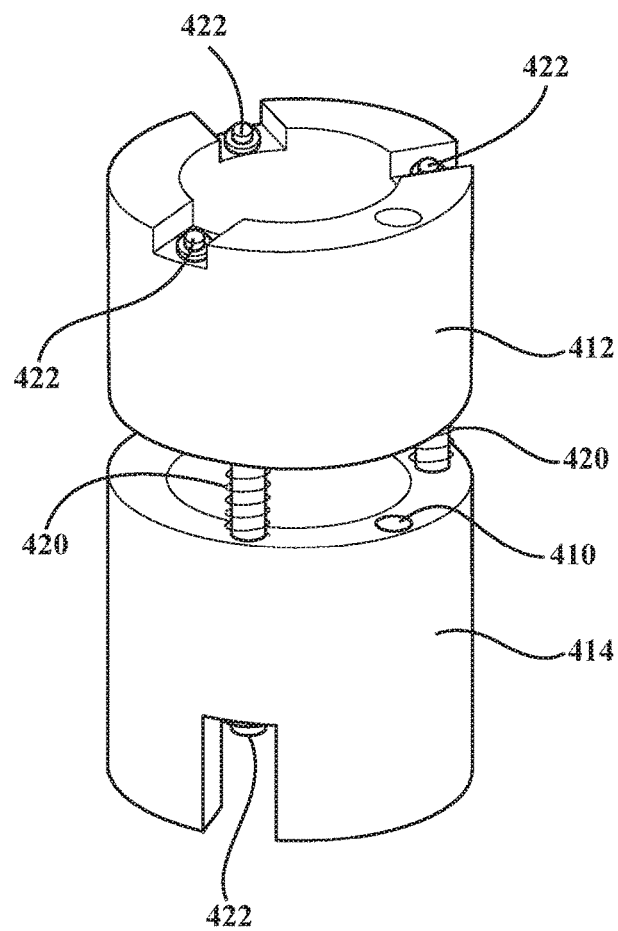
FIG. 72 is a perspective view of a portion of the grip sensing mechanism of FIG. 62 with the activator holder in a spaced position relative to the sensor holder.
Figure 73:
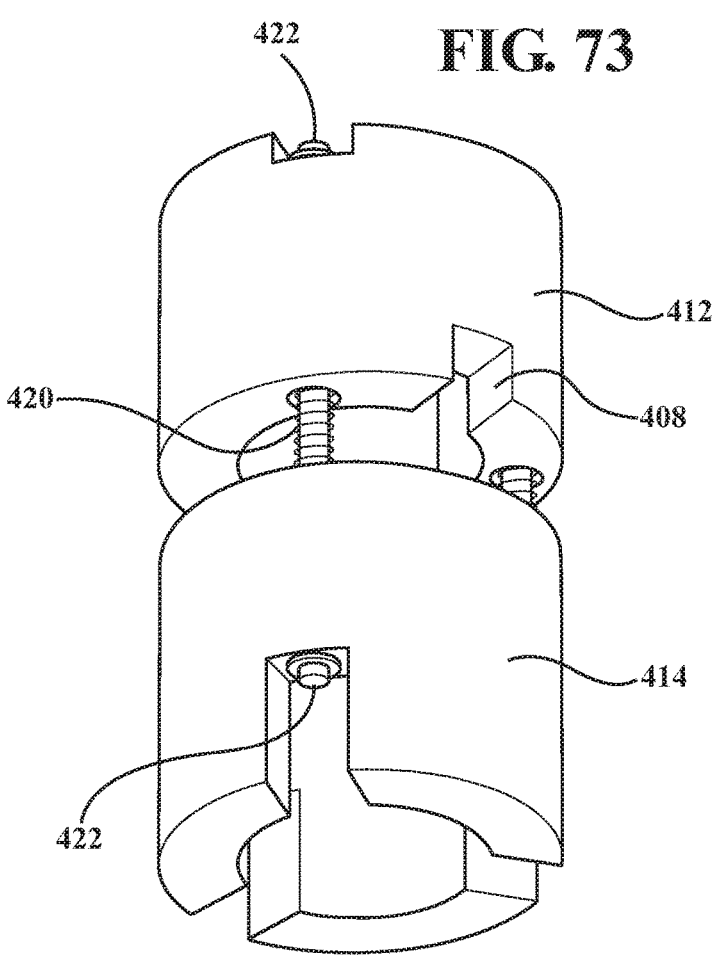
FIG. 73 is another perspective view of a portion of the grip sensing mechanism of FIG. 70.
Figure 74:
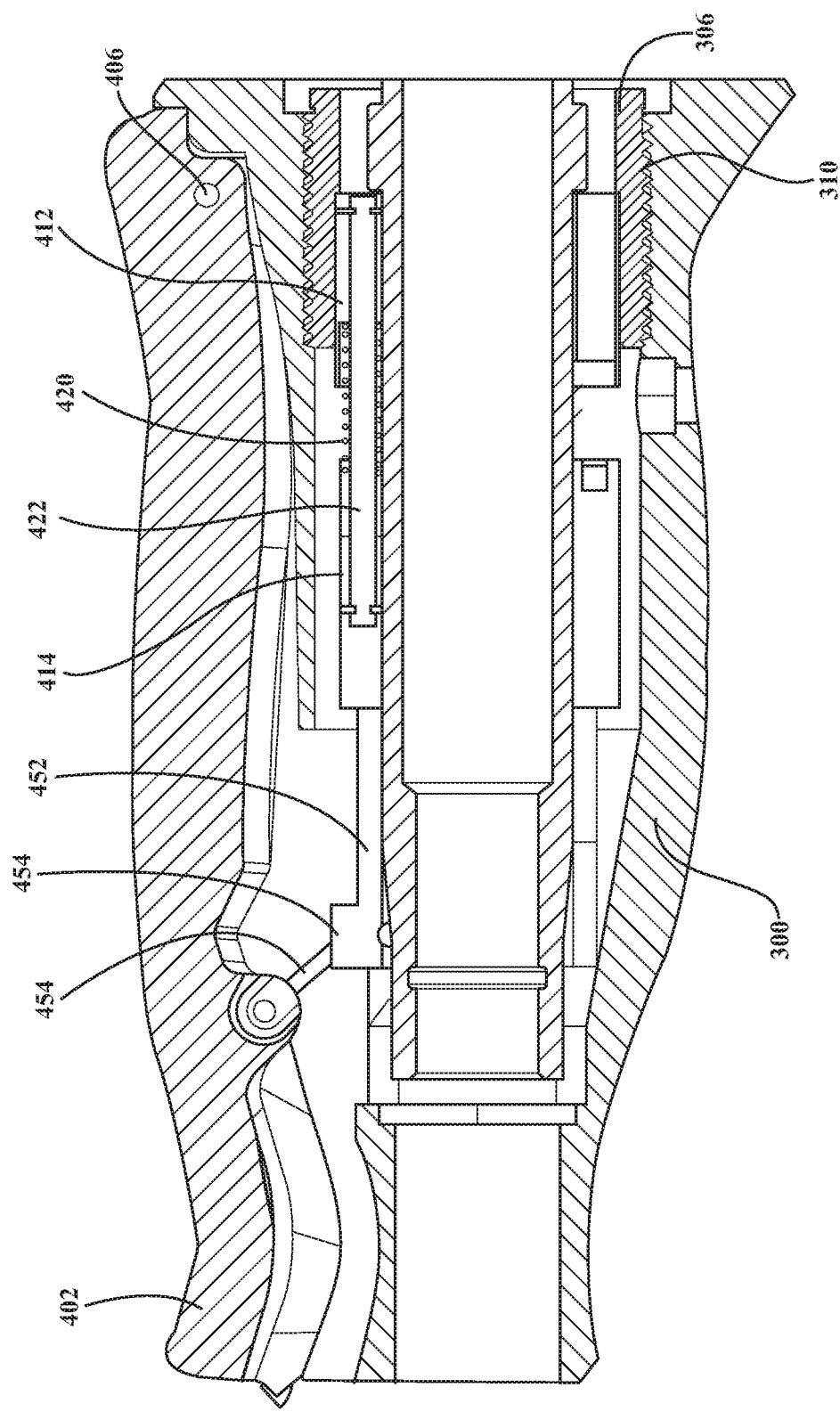
FIG. 74 is a cross-sectional view of the grip sensing mechanism and the handle with the lever in a released position.
Figure 75:
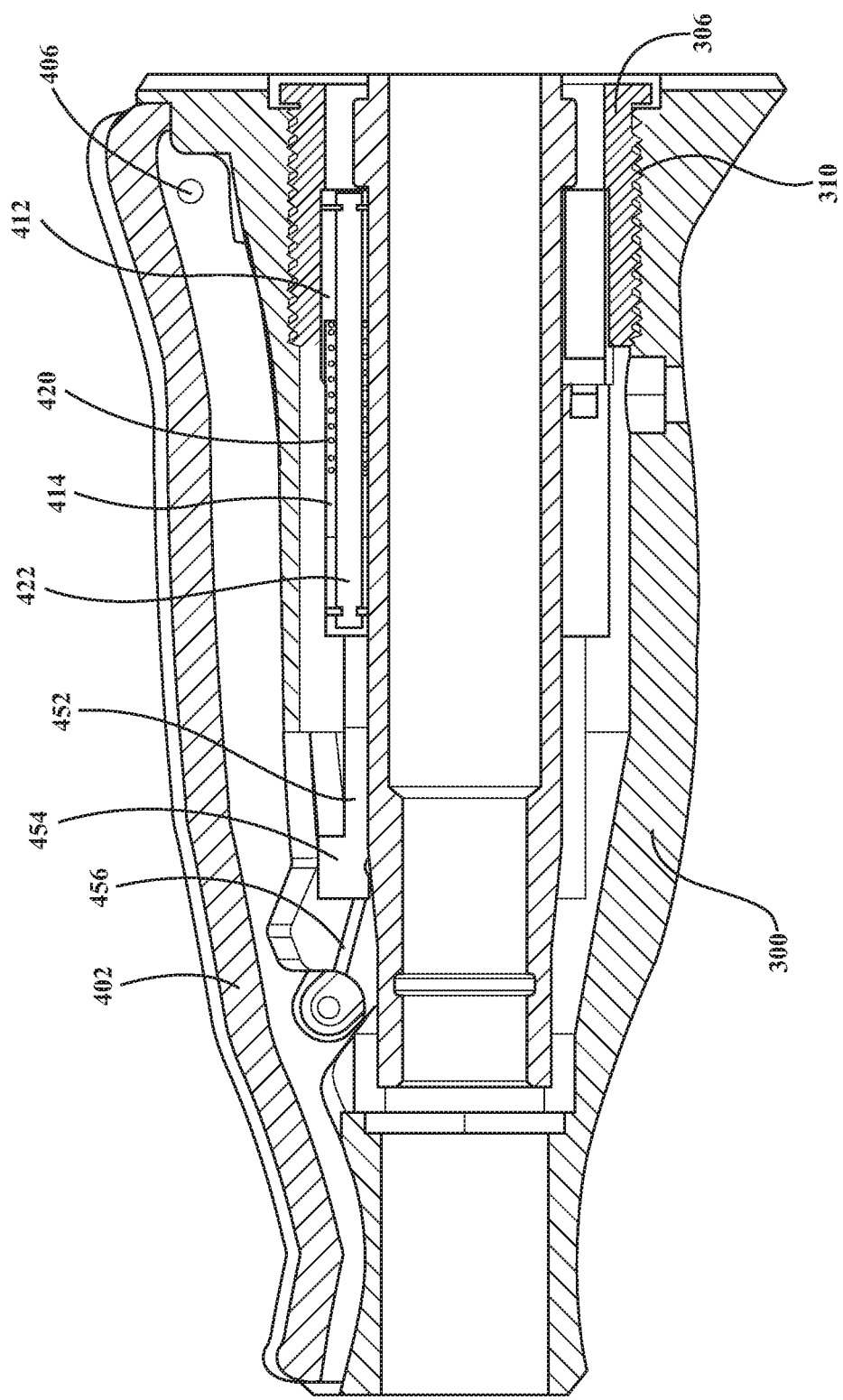
FIG. 75 is a cross-sectional view of the grip sensing mechanism and the handle with the lever in a depressed position.
Figure 76:
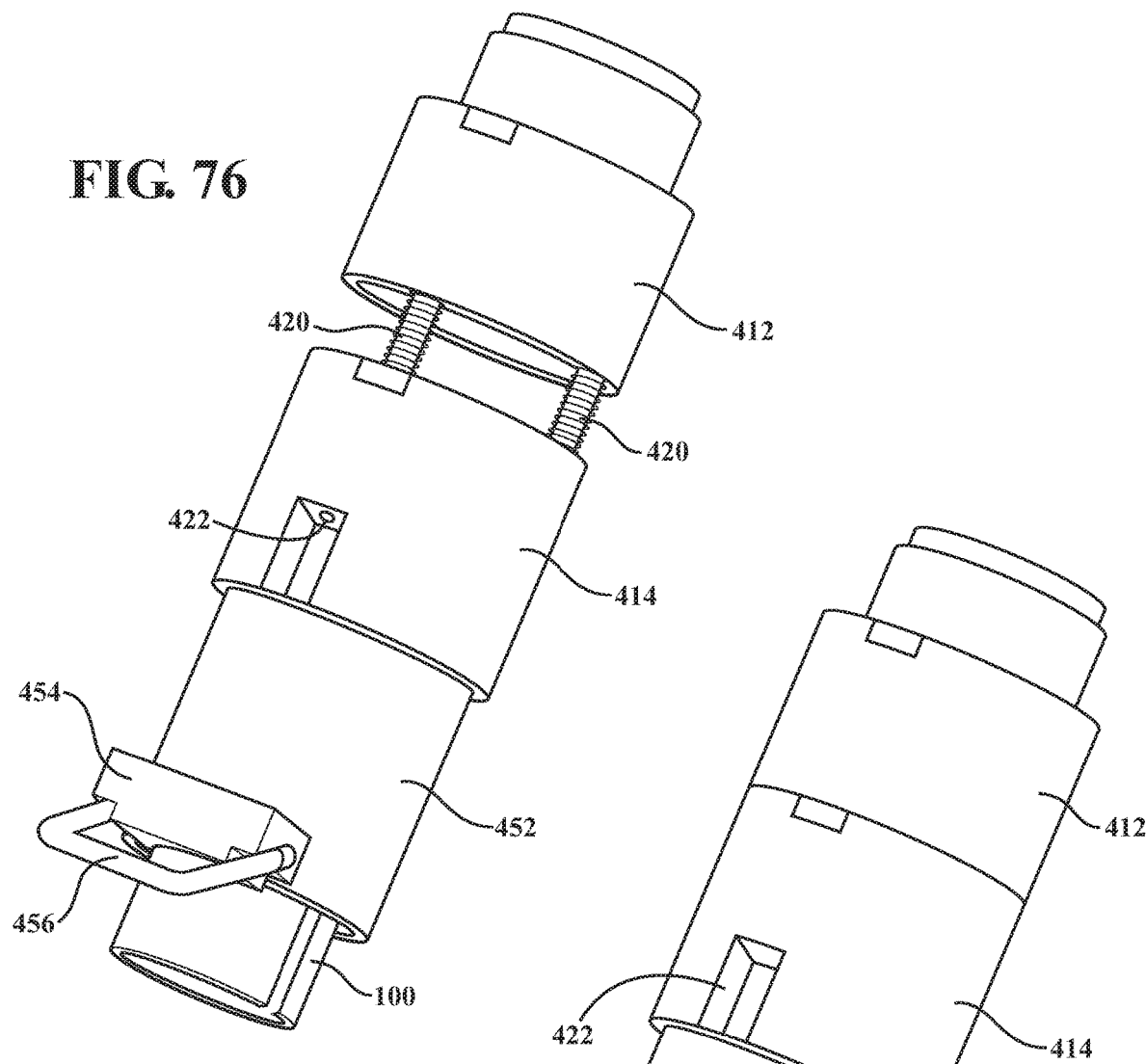
FIG. 76 is a perspective view of a portion of the grip sensing mechanism with an activator holder in a spaced position relative to the sensor holder.
Figure 77:
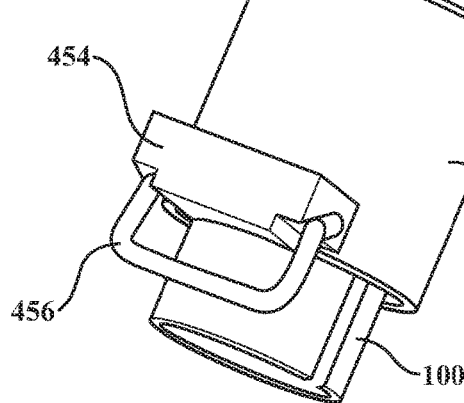
FIG. 77 is the perspective view of FIG. 76 with the activator holder in a proximate position relative to the sensor holder.

With reference to FIGS. 64-65 and 71, the grip sensing mechanism 400, 450 includes a sensor holder 412 supporting the sensor 408 and a carriage 414, i.e., an activator holder 414, supporting the activator 410. The sensor holder 412 defines a cutout receiving the sensor 408 and the activator holder 414 defines a cutout receiving the activator 410. At least one of the sensor holder 412 and the activator holder 414 is coupled to the lever 402 and is configured to move in response to actuation of the lever 402.

With reference to FIGS. 64-77, the sensor holder 412 and the activator holder 414 are coupled to the nose tube 100 and at least one of the sensor holder 412 and the activator holder 414 is moveable relative to the other along the nose tube bore 102. For example, with reference to FIGS. 64 and 71, the sensor holder 412 and the activator holder 414 each define a bore 416, 418 that slideably receives the nose tube 100. The sensor holder 412 is fixed to the nose tube 100 and the activator holder 414 is moveable relative to the nose tube 100 along nose tube bore 102 toward and away from the sensor holder 412. Alternatively, the activator holder 414 is fixed to the nose tube 100 and the sensor holder 412 is moveable relative to the nose tube bore 102 toward and away from the activator holder 414 or both the activator holder 414 and the sensor holder 412 are moveable relative to the nose tube bore 102 toward and away from each other.

With reference to FIGS. 66-69 and 74-77, the activator holder 414 is moveable along the nose tube 100 toward the sensor holder 412 to a proximate position, as shown in FIGS. 66, 68, 74, and 76, and away from the sensor holder 412 to a spaced position, as shown in FIGS. 67, 69, 75, and 77. At least one biasing device 420 is disposed between the activator holder 414 and the sensor holder 412 for urging the activator holder 414 toward the spaced position. For example, as shown in the FIGS. 64, 65, and 71, three biasing devices 420 are disposed between the activator holder 414 and the sensor holder 412. The biasing device 420 urges the activator holder 414 away from the sensor holder 412 along the nose tube axis N toward the spaced position. The biasing device 420 shown in FIGS. 67 and 68 is a coil spring. Alternatively, the biasing device 420 can be any type of spring.

With continued reference to FIGS. 64, 65, and 71, a post 422 supports the biasing device 420 between the sensor holder 412 and the activator holder 414. Specifically, for example, three posts 420 support the three biasing devices 420. The biasing device 420 is disposed on the post 422 and is configured to be retained on the post 422 between the sensor holder 412 and the activator holder 414. The post 422 extends between the sensor holder 412 and the activator holder 414 and at least one of the sensor holder 412 and the activator holder 414 slides along the post 422. For example, the activator holder 414 defines a bore 420 that slideably receives the post 422. The post 422 aligns the sensor holder 412 and the activator holder 414 about the nose tube axis N.

With reference to FIGS. 64 and 65, a push member 420 is pivotably coupled to the lever 402 and is coupled to the activator holder 414. The push member 420 is configured to move the activator holder 414 toward the proximate position in response to actuation of the lever 402 to the depressed position. The lever 402 is pinned to the push member 420 with a pin 424 that extends through the lever 402 and the push member 420. The push member 420 is pivotable relative to the lever 402 about the pin 424.

With reference to FIGS. 64 and 65, a sleeve 426 slideably receives the nose tube 100 adjacent the activator holder 414. The activator holder 414 is coupled to the lever 420 and is moveable relative to the sensor 408 along the nose tube axis N in response to movement of the lever 420 between the gripped position and the released position for indicating to the sensor 408 the position of the lever in the gripped position and the released position.

The activator holder 414 extends annularly about the nose tube axis N and slides along the nose tube 100 as the lever 420 moves between the gripped position and the released position. The push member 420 includes a fork 428 that receives the sleeve 426 and is pivotally pinned to the sleeve 426. When the push member 420 is moved relative to the nose tube 100 in response to actuation of the lever 402, the push member 420 moves the sleeve 426 and the sleeve 426 abuts and moves the activator holder 414.

With reference to FIGS. 66 and 67, the push member 420 extends transversely to the nose tube axis N from the lever 402 toward the proximal end 108 of the nose tube 100 at an acute angle relative to the lever 402. When the lever 402 is actuated, i.e., when the lever 402 is moved to the depressed position, the lever 402 forces the push member 420 to slide the sleeve 426 along the nose tube axis N toward the proximal end of the nose tube 100 and the sleeve 426 forces the activator holder 414 to the proximate position against the bias of the biasing device 420. In other words, the bias of the biasing device 420 is overcome to move the activator holder 414 along the nose tube axis N to the proximate position. When the operator releases the lever 402, the biasing device 420 biases the activator holder 414 to the spaced position and the activator holder 414 abuts the sleeve 426 and pushes the sleeve 426 toward the distal end 106 of the nose tube 100. Movement of the sleeve 426 toward the distal end 106 of the nose tube 100 pivots the push member 420 and forces the lever 402 to return to the released position.

As set forth above, another embodiment of the grip sensing mechanism 450 is shown in FIGS. 70-77. With reference to FIGS. 70 and 71, the grip sensing mechanism 450 includes a sleeve 452 coupled to the lever 402 and to at least one of the actuator holder 414 and the sensor holder 412. For example, as shown in FIG. 70, the sleeve 452 slideably engages the nose tube 100 and abuts the actuator holder 414.

A push member 456 is coupled to the lever 402 and the sleeve 452 to transfer movement from the lever 402 to the sleeve 452. The sleeve 452 presents a lip 454 that receives the push member 456. The lever 402 defines a hole 458 that receives the lever 456.

With reference to FIGS. 74-77, when the lever 402 is actuated, i.e., when the lever 402 is moved to the depressed position, the lever 402 forces the lever 456 to slide the carriage 452 along the nose tube axis N toward the proximal end of the nose tube 100. The carriage 452 forces the activator holder 414 to the proximate position against the bias of the biasing device 420. In other words, the bias of the biasing device 420 is overcome to move the activator holder 414 along the nose tube axis N to the proximate position. When the operator releases the lever 402, the biasing device 420 biases the activator holder 414 to the spaced position and the activator holder 414 abuts the carriage 452 and pushes the carriage 452 toward the distal end 106 of the nose tube 100. Movement of the carriage 452 toward the distal end 106 of the nose tube 100 pivots the lever 456 and forces the lever 402 to return to the released position.

As set forth above, the handle 300 is rotatably supported by the nose tube 100 about the nose tube axis N. The lever 402 is pivotably coupled to the nose tube about a pivot point P. The pivot point P is fixed relative to the handle about the nose tube axis N. In other words, the lever 402 rotates about the nose tube axis N with the handle 300, i.e., as a unit. The carriage 414 is rotatably supported by the nose tube 100 and rotates with the handle 300 about the nose tube axis N.

With reference to FIGS. 78-83, a gear box 500 couples the actuator 34 to the drive member 202. The gear box 500 offsets the actuator 34 from the tool axis T. In other words, the actuator 34 is offset from the tool axis T to provide access for the cartridge 252 to supply liquid to the tool 38. Specifically, the actuator 34 is offset toward the manipulator 10. This shifts the center of gravity of the end effector 12 toward the manipulator 10, which reduces inertia of the manipulator 10 and improves ergonomics and handling of the end effector. The shift of the center of gravity of the end effector 12 results in better performance of the force-torque sensor on the manipulator 10.

The gear box 500 includes a housing 502 and can include at least one gear 504 supported in the housing 502. The gear 504 is in communication with the actuator 34 and the drive member 202 for transmitting rotation from the actuator 34 to the drive member 202, as shown in FIG. 81. The gear box 500 shown in the Figures includes one gear 504, however, the gear box 500 can include any number of gears between the motor and the drive member 202. Alternatively, the actuator 34 can be directly engaged with the drive member 202 and can be axially aligned with the drive member 202. In such an embodiment, the actuator 34 can be cannulated to deliver irrigation fluid to the drive member 202.

Figure 78:
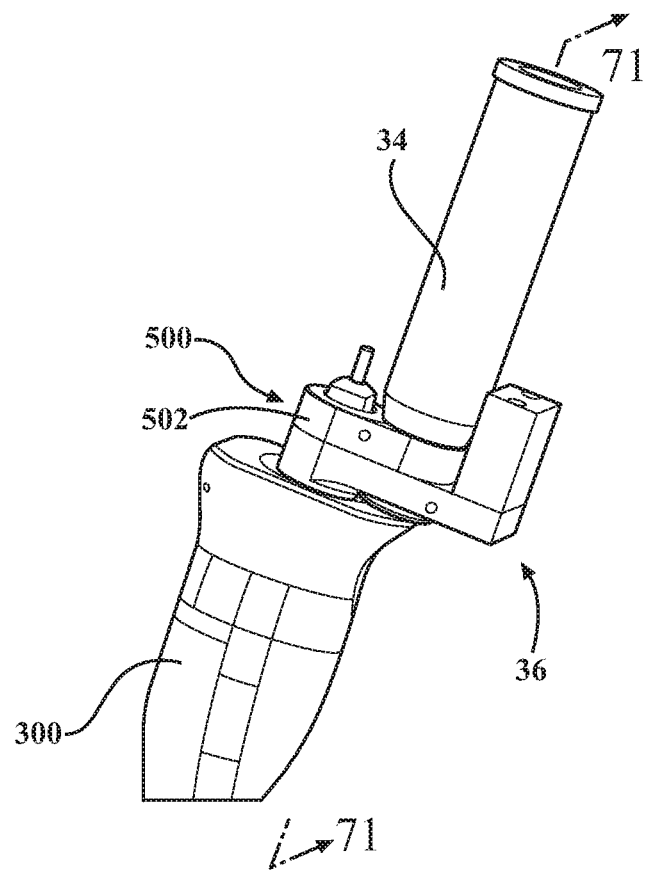
FIG. 78 is a perspective view of a portion of the end effector including a gear box.
Figure 79:
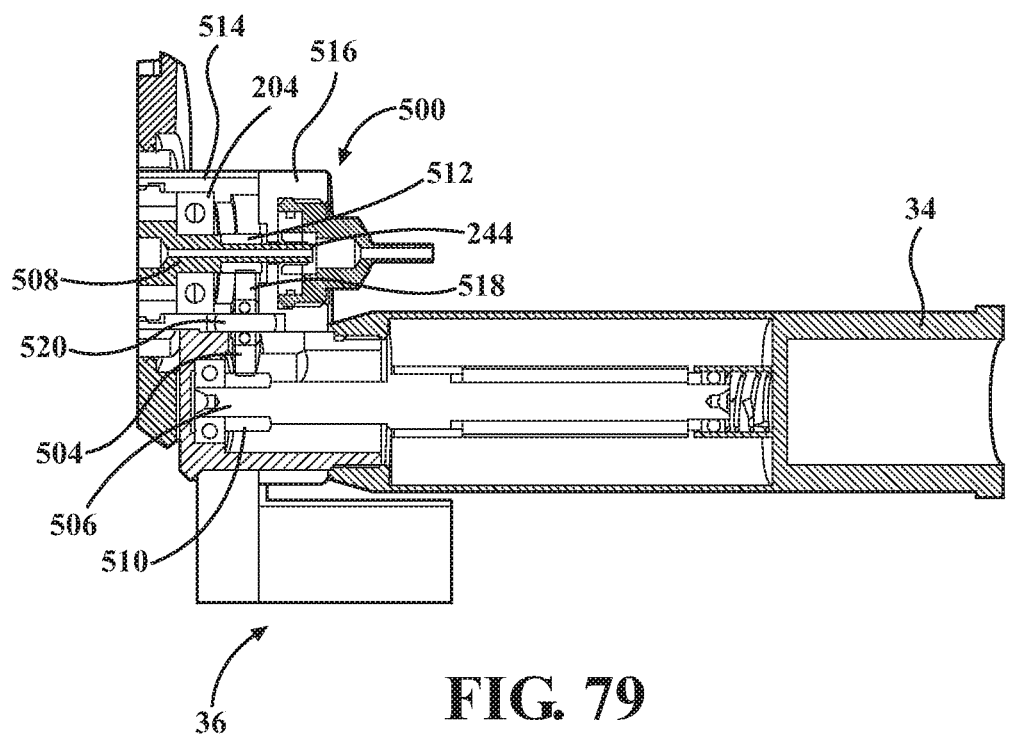
FIG. 79 is a cross-sectional view along line 71 in FIG. 78.

With reference to FIGS. 78 and 79, the housing 502 receives the actuator 34 and the drive member 202. The actuator 34 includes an output shaft 506 and the drive member 202 includes an input portion 508 with the housing 502 receiving the output shaft 506 and the input portion 508. The output shaft 506 of the actuator 34 is engaged with a gear 510. For example, the gear 510 is fixed to the output shaft 506 or can be formed on the output shaft 506. The gear 510 is meshed with the gear 504 in the housing 502.

The input portion 508 of the drive member 202 is engaged with the gear 504. For example, an idler gear 512 is fixed to the input portion 508 of the drive member 202. The idler gear 512 is meshed with the gear 504 in the housing 502.

Figure 80:
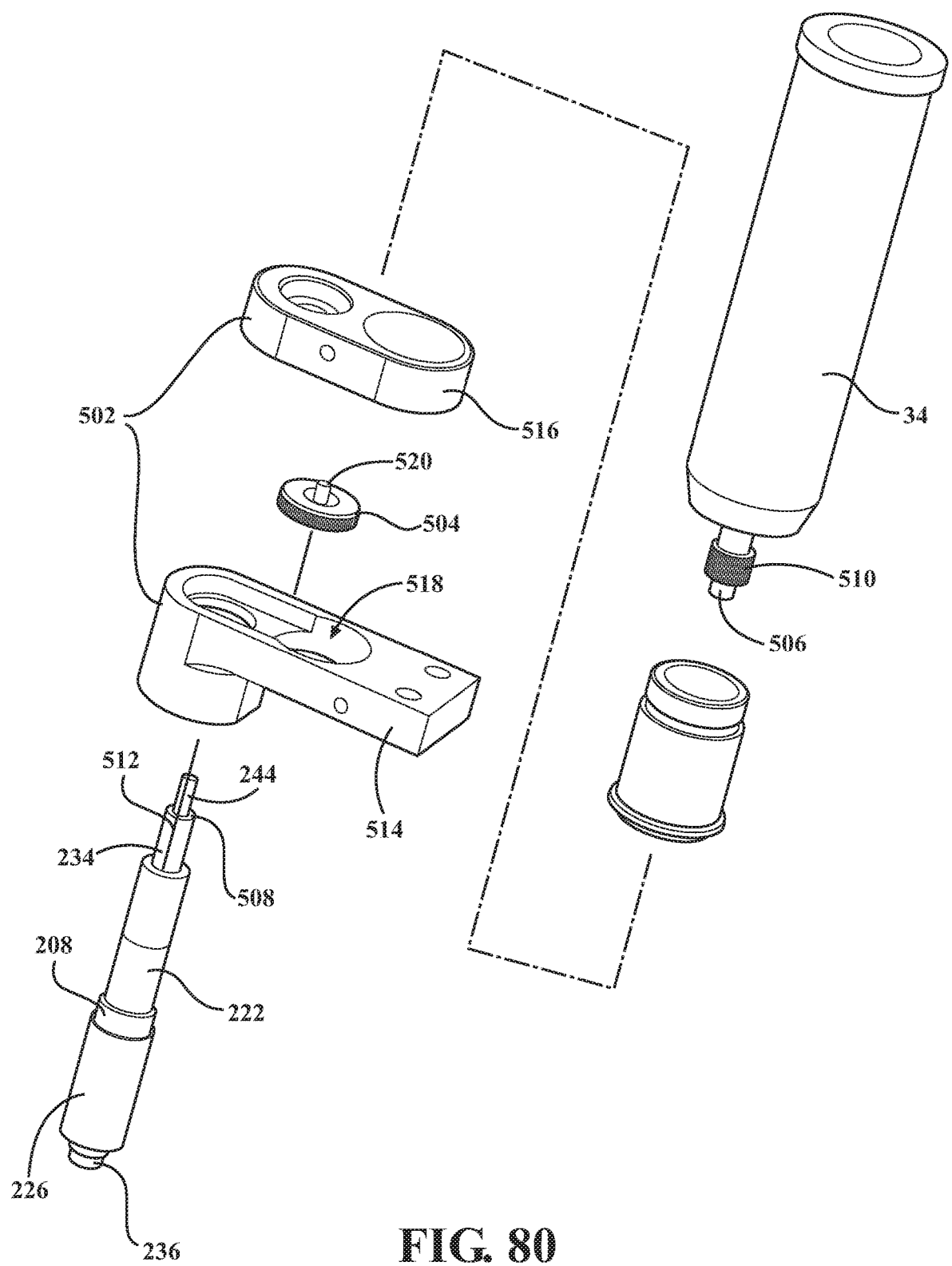
FIG. 80 is an exploded view of the gear box.

With reference to FIGS. 80, 82, and 83, the housing 502 includes a base 514 and a cover 516 mounted to the base 514. The base 514 defines a cavity 518 receiving the gear 504 and receiving the input portion 508 of the drive shaft 42 and the output shaft 506 of the actuator 34. With reference to FIGS. 79-81, an idle shaft 520 supports the gear 504 in the housing 502. In other words, the gear 504 is idle in the housing 502 and is driven by the output shaft 506 of the actuator 34.

The actuator 34 is typically a motor. For example, the motor can be an electric, brushless, Hall-less, DC permanent magnet motor. Alternatively, for example, the actuator 34 can be a brushed motor, and AC motor, a pneumatic motor, a hydraulic motor, etc.

IV. Cutting Accessory Identification

With reference to FIGS. 84-89, the cutting accessory 32 and/or guard 68 include a first circuit 600, e.g., an identification element 600, and the nose tube 100 includes a second circuit 606. The first circuit 600 and the second circuit 606 are configured to communicate with each other.

Figure 84:
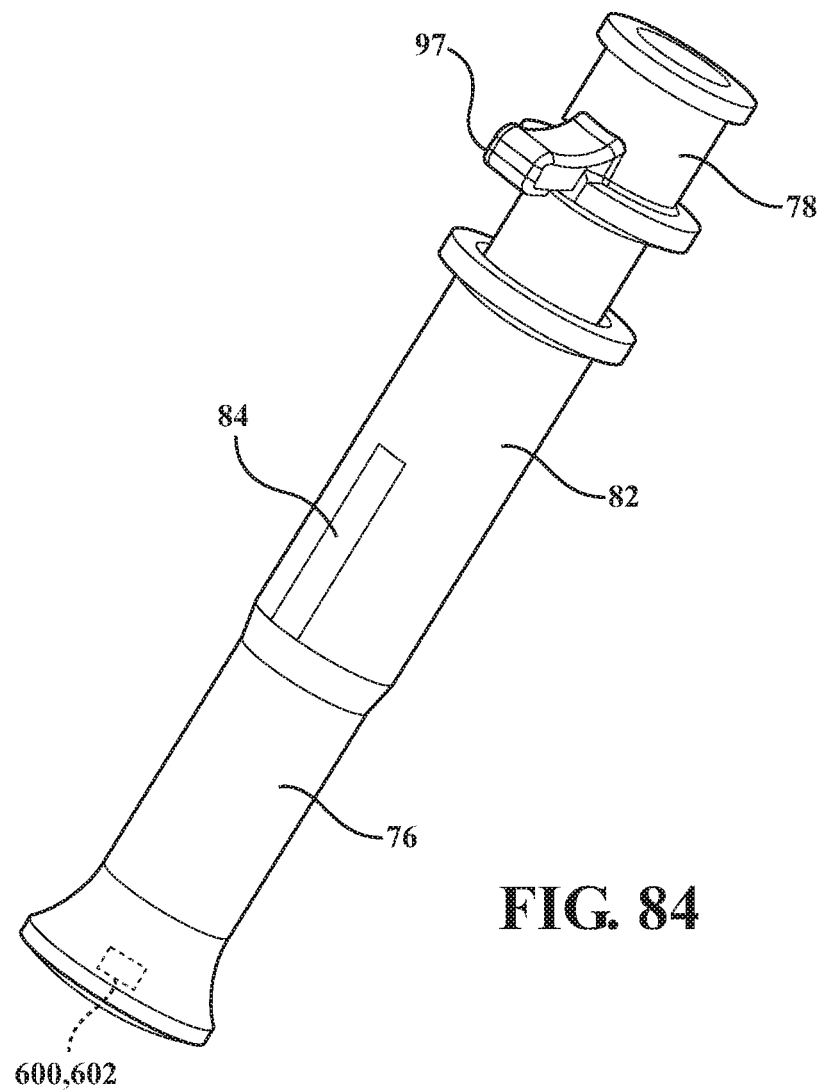
FIG. 84 is a cross-sectional view of the guard with a wireless communication element.
Figure 85:
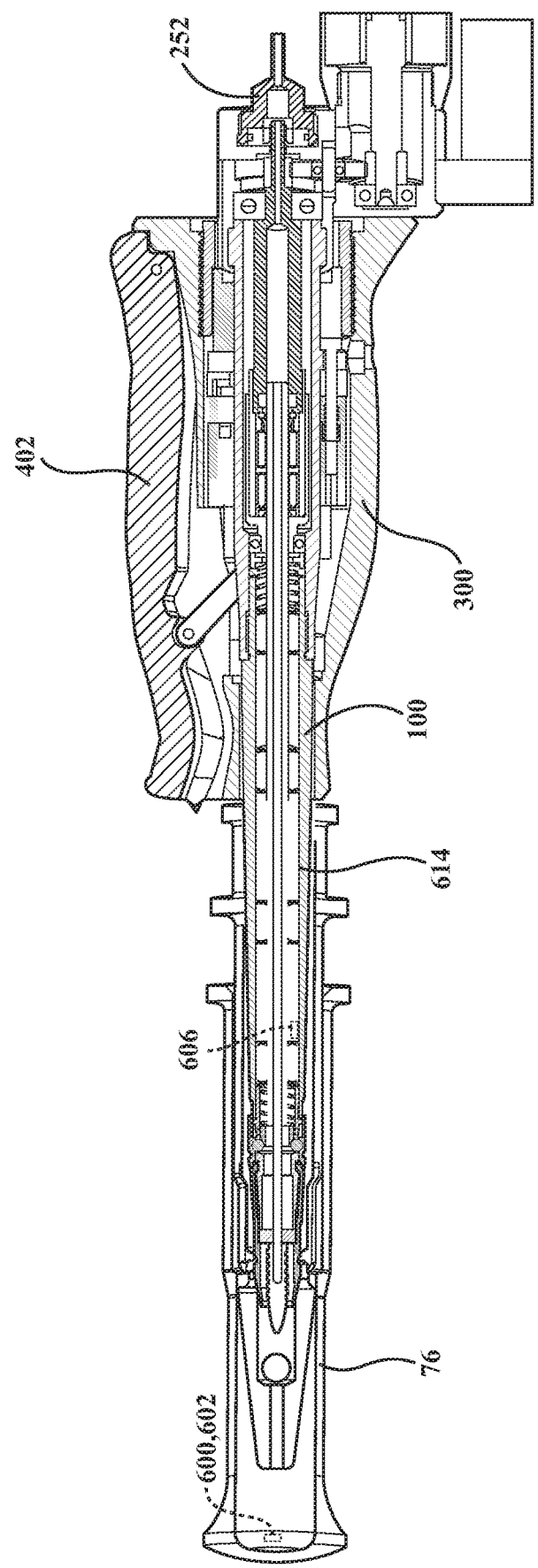
FIG. 85 is a cross-sectional view of the guard of FIG. 76 disposed on the nose tube.

The identification element 600 is, for example, a wireless data element 602, as shown in FIGS. 84-85, or wired data element 604, as shown in FIGS. 86-89. The identification element 600 communicates with the end effector 12 to identify the cutting accessory 32. For example, the identification element 600 can identify to the end effector 12 the type, size, manufacturer, life use data, and/or other parameters of the cutting accessory.

With reference to FIGS. 84-85, the wireless data element 602 is, for example, a radiofrequency identification (RFID) element, e.g., chip, tag, etc. The wireless data element 602 of FIGS. 84-85 is mounted to the guard 68. Alternatively, the wireless data element 602 can be supported by the cutting accessory 32, e.g., in the shroud. For example, the wireless data element 602 can be connected to the inside surface 160 of the shroud 140 of FIGS. 24 and 25.

With reference to FIG. 85, the second circuit 606, e.g., a wireless reader 606 such as an RFID reader, is mounted to the nose tube 100. The wireless reader 606 can, for example, be a wire coil that acts as an antenna. This coil can be wound with thermocouple wire to additionally act as a temperature sensor for the bearings in the nose tube.

The wireless reader 606 receives a signal from the wireless data element 602. The wireless reader 606 is connected to the manipulator controller 30 to transfer the signal/data from the wireless data element 602 to the manipulator controller 30 so that the manipulator controller 30 can use the signal/data to operate the end effector 12 according to the parameters of the cutting accessory 32. As shown in FIG. 85, the signal/data can be communicated to the manipulator controller 30. For example, a flex circuit 614 or wire, etc. connects to the wireless reader 606 to deliver the signal/data.

Figure 86:
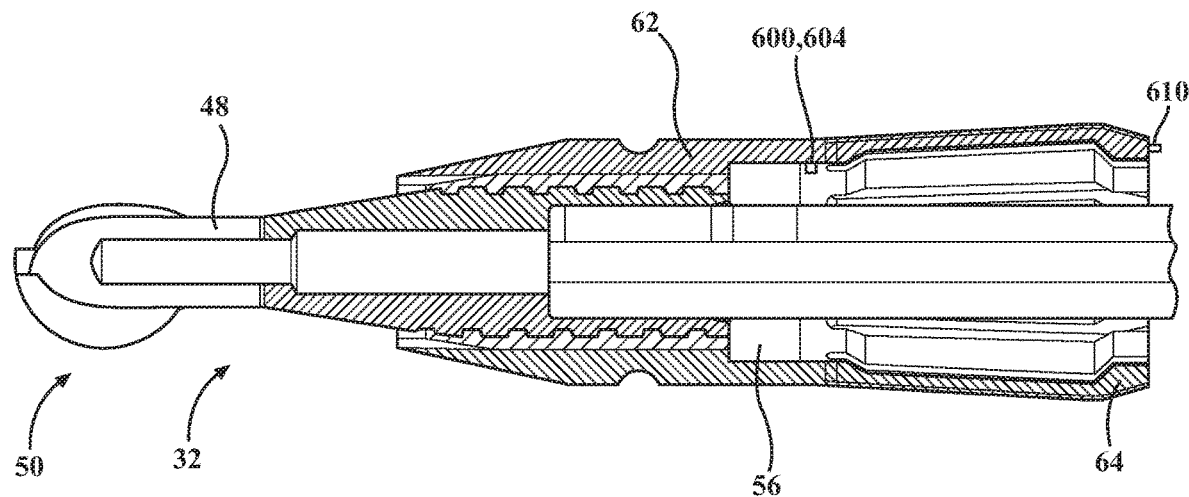
FIG. 86 is a cross-section of the cutting accessory including a wired communication element.

With reference to FIG. 86, the wired data element 604 is memory such as, for example, non-volatile random access memory (NVRAM). The memory is supported in the shroud 40 of the cutting accessory 32.

Figure 87:
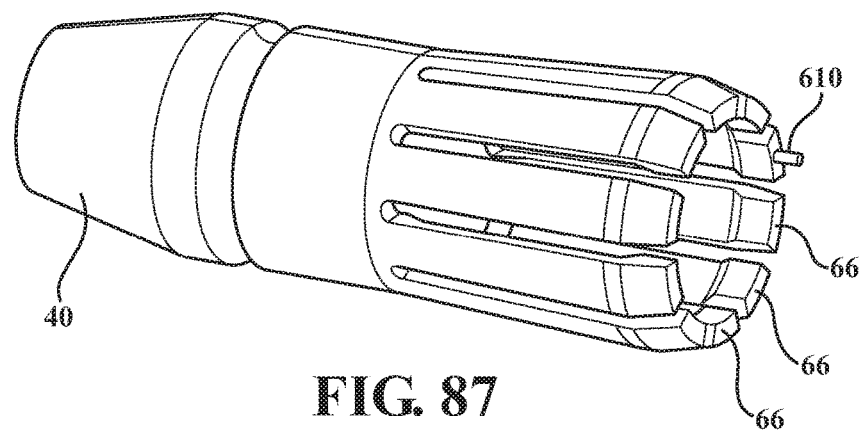
FIG. 87 is a perspective view of the shroud including a connector.
Figure 88:
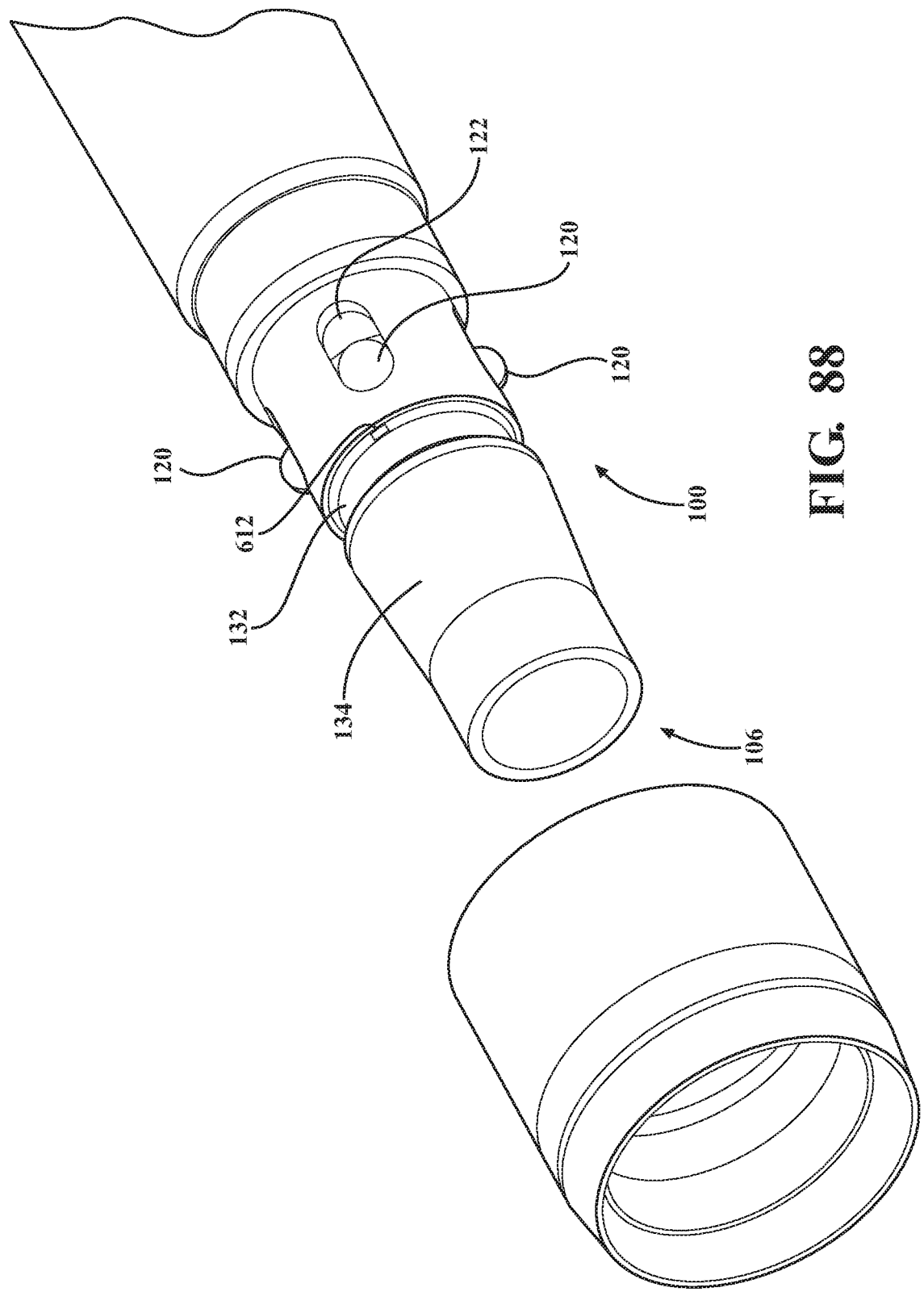
FIG. 88 is a perspective view of an end of the nose tube including a connector.

With reference to FIGS. 86 and 87, one of the fingers 64 of the shroud 40 supports a connection 610 that is connected to the wired data element 604 with, for example, a flex circuit, wire, etc., which is not shown. With reference to FIG. 87, the nose tube 100 supports a corresponding connection 612 configured to connect to connection 610 when the cutting accessory 32 is connected to the nose tube 100. The cutting accessory 32 and/or the nose tube 100 can include alignment features (not shown) configured to align the shroud 40 with the nose tube 100 such that the connector 610 is aligned with the connector 612 when the cutting accessory 32 is engaged with the nose tube 100.

Figure 89:
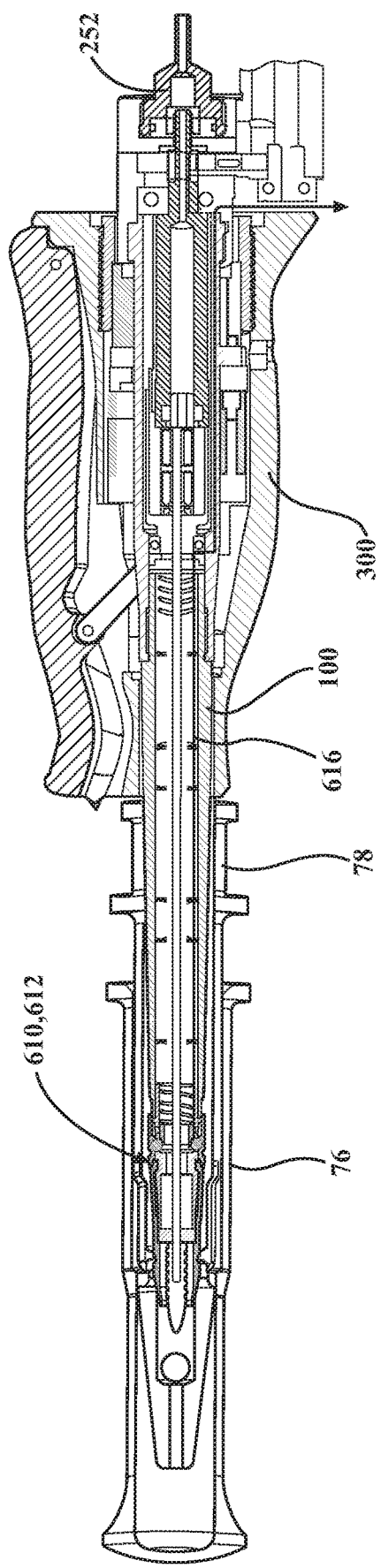
FIG. 89 is a cross-sectional view of the shroud of FIG. 86 connected to the nose tube of FIG. 88.

With reference to FIG. 89, the connector 612 is connected to the manipulator controller 30 to transfer the signal/data from the wireless communicating element 602 to the manipulator controller 30 so that the manipulator controller 30 can use the signal/data to operate the end effector 12 according to the parameters of the cutting accessory 32. As shown in FIG. 89, the signal/data can be communicated to the manipulator controller 30. For example, a flex circuit 616 or wire, etc., connects to the connector 612 to deliver the signal/data.

A method of assembling the cutting accessory 32 to the nose tube 100 is followed to identify the cutting accessory 32 to the manipulator controller 30. For example, in the embodiment of FIGS. 84-85 with the first circuit mounted to the guard 68, the method includes first providing the cutting accessory 32 with the guard 68 covering a portion of the cutting accessory 32. Specifically, the guard 68 covers the cutting tip 50 of the cutting accessory 32.

The method includes inserting the cutting accessory 32 into the nose tube 100 along the nose tube axis N to couple the cutting accessory 32 with the nose tube 100, as described above. The method includes introducing the first circuit 600 into communication with the second circuit 606. Specifically, as the cutting accessory 32 is inserted into the nose tube 100, the first circuit 600 comes within sufficient proximity to the second circuit 606 to enable wireless communication.

After the cutting accessory 32 is connected to the nose tube 100, the guard 68 is removed and set aside. At this time, the communication between the first circuit 600 and the second circuit 606 is complete and proximity of the first circuit 600 near the second circuit 606 is no longer necessary.

The invention has been described in an illustrative manner, and it is to be understood that the terminology which has been used is intended to be in the nature of words of description rather than of limitation. Many modifications and variations of the present invention are possible in light of the above teachings, and the invention may be practiced otherwise than as specifically described.

What is claimed is:

1. An end effector comprising:
    a housing;
    a nose tube coupled to said housing;
    a cutting accessory defining a bore;
    a drive system including an actuator, a rotational drive member having a distal end and an opposing proximal end, said rotational drive member disposed within said nose tube and configured to be rotated relative to said nose tube by said actuator, and a drive connector coupled to said distal end of said rotational drive member, said drive connector configured to releasably engage said cutting accessory and to rotate the cutting accessory, said rotational drive member defining a lumen for receiving liquid from a liquid source, wherein said lumen is configured to be in communication with said bore of said cutting accessory so that said bore is capable of delivering the liquid from said lumen to a surgical site;
    a first seal configured to seal between said drive system and said cutting accessory; and
    a cartridge releasably coupled to said proximal end of said rotational drive member to deliver the liquid from the liquid source to said lumen of said rotational drive member, said cartridge including a second seal configured to seal against said rotational drive member during rotation of said rotational drive member relative to said cartridge, wherein said housing defines a cavity that releasably receives said cartridge.

2. The end effector as set forth in claim 1, wherein said rotational drive member extends along an axis and wherein said first seal and said second seal extend about said axis and are spaced from each other along said axis.

3. The end effector as set forth in claim 2, wherein said first seal is arranged to slideably receive said cutting accessory along said axis.

4. The end effector as set forth in claim 1, wherein said rotational drive member presents a nipple configured to be releasably received by said cartridge such that said second seal is disposed around said nipple.

5. The end effector as set forth in claim 1, wherein said second seal comprises a dynamic seal.

6. The end effector as set forth in claim 5, wherein said rotational drive member is configured to rotate within said dynamic seal.

7. An end effector for actuating a cutting accessory, said end effector comprising:
    a housing;
    a nose tube coupled to said housing;
    a drive system including an actuator, a rotational drive member disposed within said nose tube and configured to be rotated relative to said nose tube by said actuator, and a drive connector coupled to said rotational drive member, said drive connector configured to releasably engage the cutting accessory to rotate the cutting accessory, said rotational drive member defining a lumen for receiving liquid from a liquid source, wherein said lumen is configured to be in communication with a bore of the cutting accessory so that the bore is capable of delivering the liquid from said lumen to a surgical site;
    a first seal configured to seal between said drive system and the cutting accessory; and
    a cartridge releasably coupled to a proximal end of said rotational drive member to deliver the liquid from the liquid source to said lumen of said rotational drive member, said cartridge including a second seal configured to seal against said rotational drive member during rotation of said rotational drive member relative to said cartridge, wherein said housing defines a cavity that releasably receives said cartridge.

8. The end effector as set forth in claim 7, wherein said rotational drive member extends along an axis and wherein said first seal and said second seal extend about said axis and are spaced from each other along said axis.

9. The end effector as set forth in claim 8, wherein said first seal is arranged to slideably receive the cutting accessory along said axis.

10. The end effector as set forth in claim 7, wherein said rotational drive member presents a nipple configured to be releasably received by said cartridge such that said second seal is disposed around said nipple.

11. The end effector as set forth in claim 7, wherein said second seal comprises a dynamic seal.

12. The end effector as set forth in claim 11, wherein said rotational drive member is configured to rotate within said dynamic seal.

* * * * *